(12) United States Patent
Kim et al.

(10) Patent No.: US 11,759,137 B2
(45) Date of Patent: Sep. 19, 2023

(54) ELECTRONIC DEVICE FOR PROVIDING GUIDE INFORMATION

(71) Applicant: Samsung Electronics Co., Ltd., Gyeonggi-do (KR)

(72) Inventors: Doyoon Kim, Gyeonggi-do (KR); Areum Ko, Gyeonggi-do (KR); Moorim Kim, Gyeonggi-do (KR); Minhyoung Lee, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 404 days.

(21) Appl. No.: 17/111,902

(22) Filed: Dec. 4, 2020

(65) Prior Publication Data

US 2021/0169390 A1    Jun. 10, 2021

(30) Foreign Application Priority Data

Dec. 6, 2019    (KR) .................. 10-2019-0161960

(51) Int. Cl.
*A61B 5/257*    (2021.01)
*A61B 5/00*    (2006.01)
(Continued)

(52) U.S. Cl.
CPC ............ *A61B 5/257* (2021.01); *A61B 5/0059* (2013.01); *A61B 5/053* (2013.01); *A61B 5/273* (2021.01);
(Continued)

(58) Field of Classification Search
CPC ......... A61B 5/257; A61B 5/358; A61B 5/273; A61B 5/36; A61B 5/28; A61B 5/366; A61B 5/0059; A61B 5/053
See application file for complete search history.

(56) References Cited

U.S. PATENT DOCUMENTS

| 6,282,440 | B1 * | 8/2001 | Brodnick | A61B 5/341 |
| | | | | 600/512 |
| 2007/0038078 | A1 * | 2/2007 | Osadchy | A61B 5/6885 |
| | | | | 600/424 |

(Continued)

FOREIGN PATENT DOCUMENTS

| KR | 10-2015-0050005 A | 5/2015 |
| KR | 10-2015-0095439 A | 8/2015 |

(Continued)

OTHER PUBLICATIONS

International Search Report dated Mar. 25, 2021.

*Primary Examiner* — Catherine M Voorhees
*Assistant Examiner* — Roland Dinga
(74) *Attorney, Agent, or Firm* — Cha & Reiter, LLC

(57) ABSTRACT

An electronic device and method are disclosed herein. The electronic device includes a housing, a first, second, third and fourth electrode coupled to the housing, a communication module, and a processor. The processor implements the method, including: detect a first signal using the first electrode and the fourth electrode, detect a second signal using the second electrode and the fourth electrode, detect a third signal using the third electrode and the fourth electrode, transmit the first signal, the second signal, and the third signal to an external electronic device via the communication module, and receive, from the external electronic device, via the communication module, data for generating guidance information to correct an attachment position of the electronic device, wherein the guidance information is generated based on: a first biological signal generated based on the first signal and the second signal, a second biological signal generated based on the second signal and the third signal, and a third biological signal generated based on the third signal and the first signal.

17 Claims, 28 Drawing Sheets

(51) Int. Cl.
*A61B 5/053* (2021.01)
*A61B 5/358* (2021.01)
*A61B 5/273* (2021.01)
*A61B 5/28* (2021.01)
*A61B 5/36* (2021.01)
*A61B 5/366* (2021.01)

(52) U.S. Cl.
CPC ............... *A61B 5/28* (2021.01); *A61B 5/358* (2021.01); *A61B 5/36* (2021.01); *A61B 5/366* (2021.01)

(56) References Cited

U.S. PATENT DOCUMENTS

| | | | |
|---|---|---|---|
| 2014/0296682 | A1 | 10/2014 | Wada et al. |
| 2014/0296686 | A1* | 10/2014 | Konchitsky .............. A61B 5/25 600/393 |
| 2015/0173670 | A1 | 6/2015 | Simon |
| 2016/0199000 | A1* | 7/2016 | Gimenez ............... G01J 1/4204 250/208.6 |
| 2019/0059732 | A1 | 2/2019 | Kim et al. |
| 2019/0239769 | A1* | 8/2019 | Lee ........................ A61B 5/282 |

FOREIGN PATENT DOCUMENTS

| | | |
|---|---|---|
| KR | 10-2016-0147516 A | 12/2016 |
| KR | 10-1950815 B1 | 2/2019 |
| KR | 10-2019-0096098 A | 8/2019 |
| WO | 2015/073588 A1 | 5/2015 |

* cited by examiner

ELECTRONIC DEVICE FOR PROVIDING GUIDE INFORMATION

CROSS-REFERENCE TO RELATED APPLICATION(S)

This application is based on and claims priority under 35 U.S.C. 119 to Korean Patent Application No. 10-2019-0161960, filed on Dec. 6, 2019, in the Korean Intellectual Property Office, the disclosure of which is herein incorporated by reference in its entirety.

TECHNICAL FIELD

Certain embodiments relate to an electronic device for providing guide information.

BACKGROUND

Biological signals, such as a heart rate, a heart rhythm, an electrocardiogram (ECG), a photoplethysmography (PPG), a blood pressure, a blood-oxygen saturation level, a respiratory rate, a blood sugar level, and a body temperature, may be used as indicators for predicting a user or patient condition. Information based on biological signals may be variously used not only for medical treatment of a patient, but also for general; health care. A user may detect biological signals, such as a heart rate, a heart rhythm, an electrocardiogram (ECG), and a photoplethysmography (PPG), by using an electronic device attached to the body of the user.

SUMMARY

A biological signal measurement device may have a plurality of pads, each of which may be provided with one or more measuring electrodes, and each of the pads may be connected to a circuit device via one or more conducting wires. In such a the measurement device, each pad may be attached to a user's body, in which the number and placement of the attached measurement electrodes may be determined somewhat freely, which may allow the measurement device to have an increased degree of accuracy in measurement. However, when a patient attaches an electrocardiogram patch by himself/herself at home, the electrocardiogram patch may not be attached at an optimal position, compared to attachment by a trained medical specialist, and thus there may be an resultant increase in digital noise of an electrocardiogram signal.

An electronic device according to certain embodiments may generate guide information based on a biological signal to guide a user to a position at which an electrocardiogram patch is to be attached.

An electronic device according to certain embodiments may generate guide information based on angle information of an electrocardiogram patch to guide a user to a position at which the electrocardiogram patch is to be attached.

The problem to be solved of the disclosure is not limited to the above-mentioned problem, and may be variously expanded without departing from the disclosure.

An electronic device according to certain embodiments may include: a housing, a first, second, third and fourth electrode coupled to the housing, a communication module, and a processor, configured to: detect a first signal using the first electrode and the fourth electrode, detect a second signal using the second electrode and the fourth electrode, detect a third signal using the third electrode and the fourth electrode, transmit the first signal, the second signal, and the third signal to an external electronic device via the communication module, and receive, from the external electronic device, via the communication module, data for generating guidance information to correct an attachment position of the electronic device, wherein the guidance information is generated based on: a first biological signal generated based on the first signal and the second signal, a second biological signal generated based on the second signal and the third signal, and a third biological signal generated based on the third signal and the first signal.

An electronic device according to certain embodiments may include: a housing, a communication module, and a processor disposed in the housing, wherein the processor is configured to: receive, via the communication module, a plurality of signals generated from a first, second, third and fourth electrode of an external electronic device, including: a first signal generated using the first electrode and the fourth electrode, a second signal generated using the second electrode and the fourth electrode, and a third signal generated using the third electrode and the fourth electrode, determine a first biological signal based on the first signal and the second signal, determine a second biological signal based on the second signal and the third signal, determine a third biological signal based on the third signal and the first signal, generate correction data indicating a correction to an attachment position of the external electronic device, based on the first biological signal, the second biological signal, and the third biological signal, and transmit the correction data to the external electronic device via the communication module.

An electronic device according to certain embodiments may include: a housing, a first, second, third, and fourth electrode coupled to the housing, a processor, configured to: detect a first signal using the first electrode and the fourth electrode, detect a second signal using the second electrode and the fourth electrode, detect a third signal using the third electrode and the fourth electrode, generate a first biological signal based on the first signal and the second signal, generate a second biological signal based on the second signal and the third signal, generate a third biological signal based on the third signal and the first signal, and generate correction data indicating a correction to an attachment position of the external electronic device, based on the first biological signal, the second biological signal, and the third biological signal.

According to certain embodiments, an electronic device or a biological signal measurement device can increase accuracy in biological signal measurement by providing, to a user, guide information regarding a position to which the biological signal measurement device is to be moved, based on a biological signal.

BRIEF DESCRIPTION OF THE DRAWINGS

The above and other aspects, features, and advantages of the disclosure will be more apparent from the following detailed description taken in conjunction with the accompanying drawings, in which.

DETAILED DESCRIPTION

Figure 1:
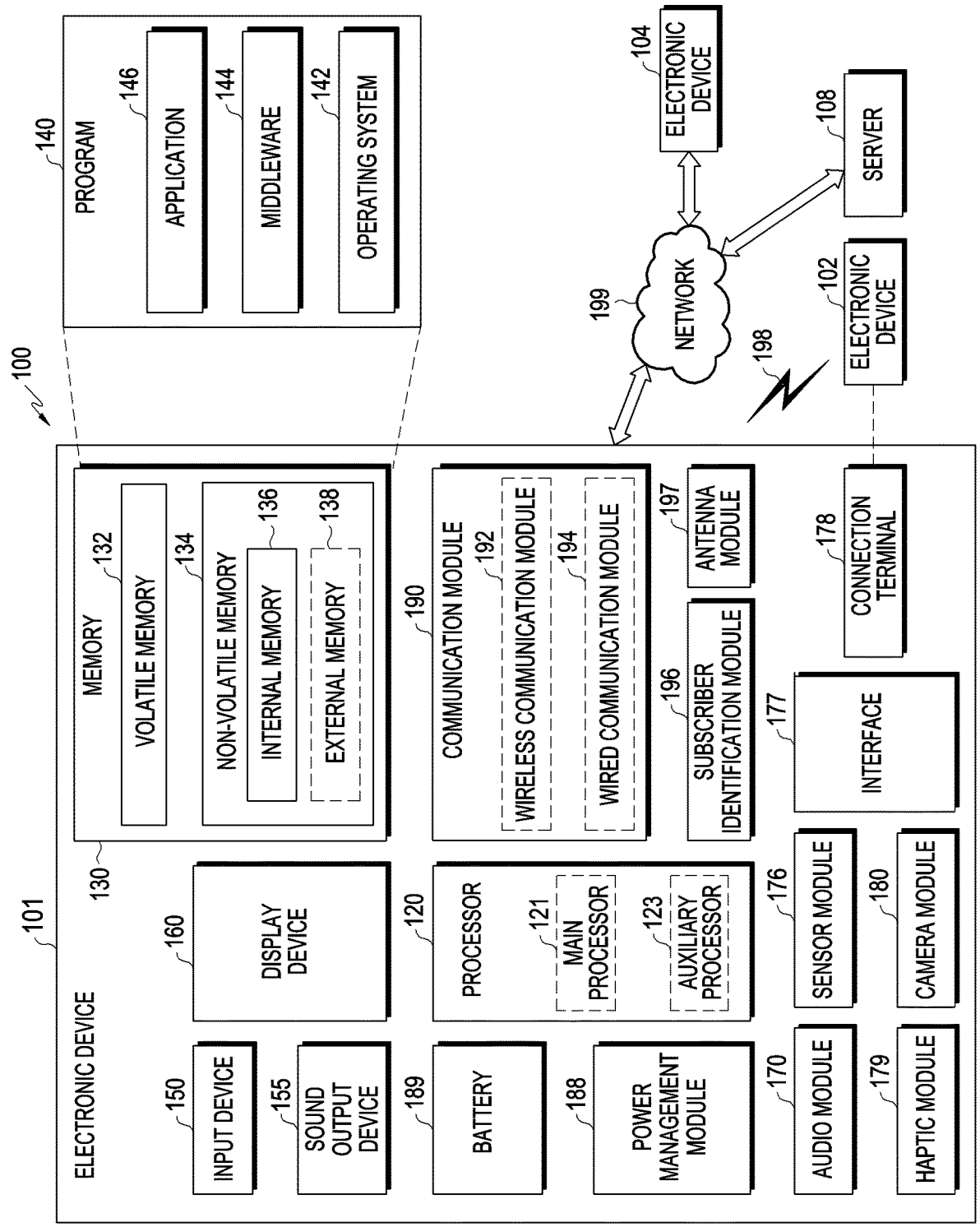
FIG. 1 is a block diagram an electronic device in a network environment according to certain embodiments.

FIG. 1 is a block diagram illustrating an electronic device 101 in a network environment 100 according to certain embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output unit 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control, for example, at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active (e.g., executing an application) state. According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by a component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output unit 155 may output sound signals to the outside of the electronic device 101. The sound output unit 155 may include, for example, a speaker or a receiver. The speaker may be used for general purposes, such as playing multimedia or playing record, and the receiver may be used for incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output unit 155 or an external electronic device (e.g., an electronic device 102 (e.g., a speaker or a headphone)) directly or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image and moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element implemented using a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 from the plurality of antennas. The signal or the power may then be transmitted or received between the communication module 190 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102 or 104, or a server 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

The electronic device according to certain embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that certain embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms such as "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Certain embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it. This allows the machine to be operated to perform at least one function according to the at least one instruction invoked. The one or more instructions may include a code generated by a complier or a code executable by an interpreter. The machine-readable storage medium may be provided in the form of a non-transitory storage medium. The term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server. According to certain embodiments, each component (e.g., a module or a program) of the above-described components may include a single entity or multiple entities. According to certain embodiments, one or more of the above-described components or operations may be omitted, or one or more other components or operations may be added. Alternatively or additionally, a plurality of components (e.g., modules or programs) may be integrated into a single component. In such a case, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

According to certain embodiments, the term "acquisition" is not limited to one of the term "generation" or "reception", and may be construed as including at least one of the term "generation" or "reception".

Figure 2:
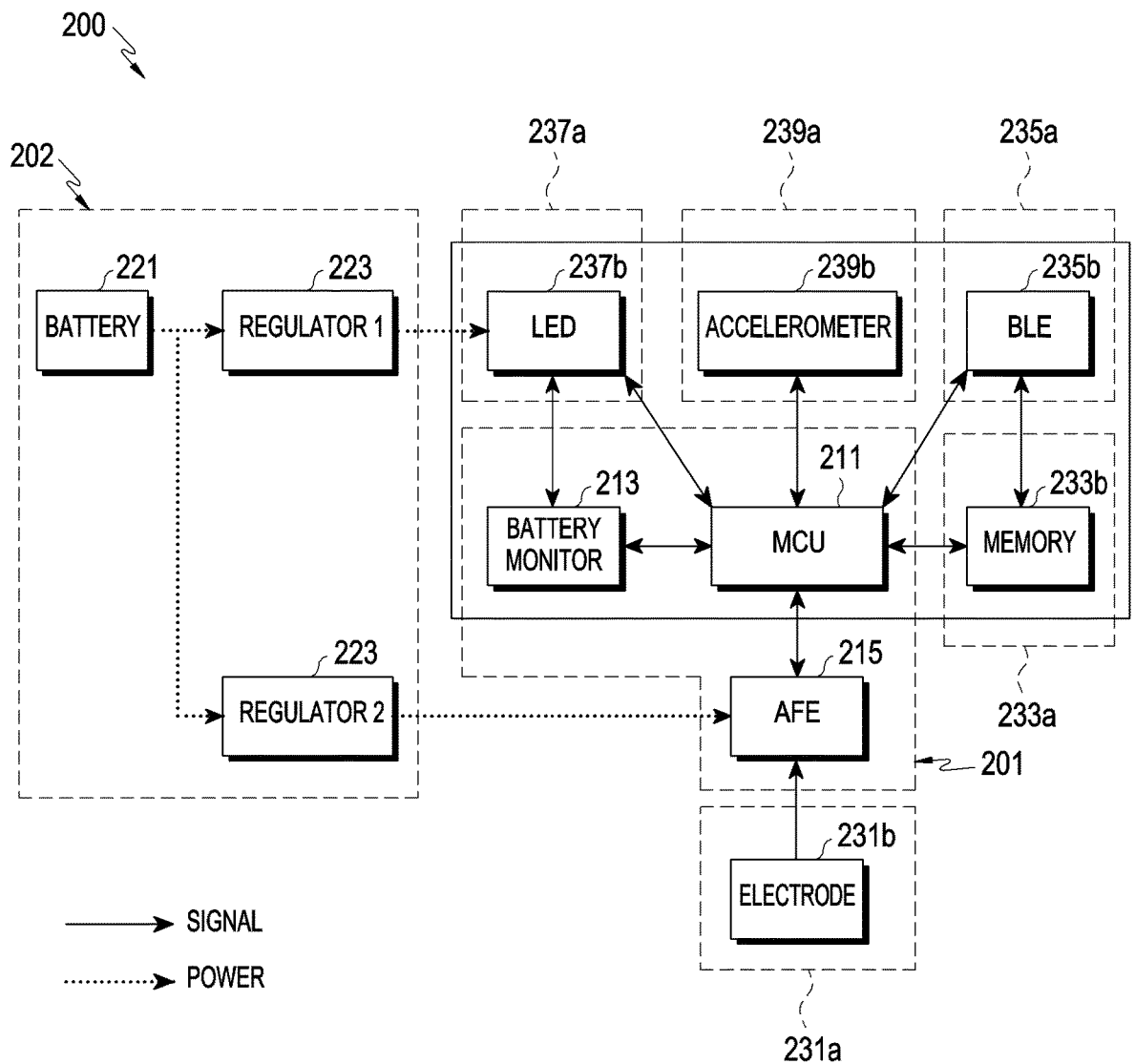
FIG. 2 is a block diagram illustrating a biological signal measurement device according to certain embodiments.

FIG. 2 is a block diagram illustrating a biological signal measurement device 200 according to certain embodiments.

The biological signal measurement device 200 may include some or all of the components including, for example, the electronic device 101 of FIG. 1. Referring to FIG. 2, the biological signal measurement device 200 may include a control unit 201, a power supply unit 202, and a mounting unit 231a, and may further include a storage unit 233a, a communication unit 235a, a display unit 237a, and a measurement unit 239a in some embodiments.

According to certain embodiments, the control unit 201 may include a Main Control Unit (MCU) 211, a battery monitor 213, and an Analog Front End (AFE) 215. The control unit 211 may include, for example, the processor 120 of FIG. 1, and may perform control of the entire biological signal measurement device 200. In an embodiment, the battery monitor 213 may measure the remaining capacity of a battery 221 included in the power supply unit 202, or the like. In another embodiment, the AFE 215 may digitize a biological signal such as an analog voltage signal detected through the mounting unit 231a, and may transmit the digitized biological signal to the control unit 211.

According to certain embodiments, the power supply unit 202 may include a battery 221 and at least one regulator 223, and in some embodiments, may include the power management module 188 and the battery 189 of FIG. 1. In an embodiment, the battery 221 may supply power for driving the biological signal measurement device 200, and may include a non-rechargeable primary battery, a rechargeable secondary battery, or a fuel cell. In another embodiment, the regulator 223 may convert the power of the battery 221 into a voltage suitable for driving the biological signal measurement device 200 (e.g., the control unit 211), and may supply the voltage.

According to certain embodiments, the control unit 211 and the power supply unit 202 may be embedded in substantially one housing (e.g., the module housing 301 illustrated in FIG. 3, which will be described later). In some embodiments, the housing, in which the power supply unit 202 and the like are embedded, may include a switch device (e.g., an operation unit 311a in FIG. 3) for turning power on/off or initiating/terminating measurement. The switch device may be a part of the power supply unit 202 or the control unit 211.

According to certain embodiments, the mounting unit 231a may provide a method of attaching the biological signal measurement device 200 to a body of a user or a patient, and may be in direct contact with the user's body so as to transmit a current or voltage signal to the control unit 211 (e.g., the AFE 215). For example, the mounting unit 231a may include an electrode(s) 231b in contact with the user's body, and the electrode 231b (e.g., a measurement electrode or a third wiring electrode 831c in FIG. 12) may be electrically connected to the AFE 215.

According to certain embodiments, the control unit 211 may generate information on the electrocardiogram, the heartbeat, and the like of the user to whom the biological signal measurement device 200 is attached on the basis of the digital signal received through the AFE 215. In some embodiments, information (e.g., first measurement information) generated by the control unit 211 may be stored in the storage unit 233a. For example, the storage unit 233a may store information generated by the control unit 211 by including a memory 233b (e.g., the memory 130 in FIG. 1).

According to certain embodiments, the information generated by the control unit 211 or the information stored in the storage unit 233a may be transmitted to another electronic device (e.g., the electronic device 102 in FIG. 1) via the communication unit 235a. In another embodiment, the information generated by the control unit 211 or the information stored in the storage unit 233a may be transmitted to still another electronic device (e.g., the electronic device 104 in FIG. 1) or a server (e.g., the server 108 in FIG. 1) via the communication unit 235a and via a network (e.g., the network 199 in FIG. 1). For example, the communication unit 235a is capable of transmitting generated information or stored information to another electronic device directly or via a network by including a Bluetooth Low Energy (BLE) 235b. In another embodiment, when the communication unit 235a maintains a state of being connected with another electronic device, either directly or via a network, the control unit 211 may transmit the generated information to the other electronic device without storing it in the storage unit 233a. It is noted the another electronic device 102 may include some or all of the same components of the electronic device illustrated in FIG. 1 or FIG. 2.

According to certain embodiments, the display unit 237a may output information on the state of the biological signal measurement device 200 under the control of the control unit 211, for example. According to an embodiment, the display unit 237a is capable of visually displaying the remaining charge of the battery, the state of attachment to the user's body (e.g., whether or not a biological signal is detectable), whether or not communication with another electronic device or the like is possible, and the like by including a light source (e.g., a Light-Emitting Diode (LED) 237b). For example, the LED 237b may provide various kinds of information to the user through the color, the blinking period, and the like of the output light. Although not illustrated, the display unit 237a may output various kinds of information through a speaker (e.g., the sound output unit 155 in FIG. 1), a vibration device (e.g., the haptic module 179 in FIG. 1), a display (e.g., the display device 160 in FIG. 1), and the like, in addition to the above-mentioned light source. The configuration of the display unit 237a as described above may be appropriately selected in consideration of the size and usage of the biological signal measurement device 200, the attachment position of the biological signal measurement device 200 in the user's body, and the like.

According to certain embodiments, the measurement unit 239a is capable of measuring a motion (e.g., an amount of motion) of a user who wears or attaches an electronic device (e.g., the biological signal measurement device 200). For example, the measurement unit 239a may include at least an accelerometer 239b, and in some embodiments, the measurement unit 239a may include a gyro sensor, an atmospheric pressure sensor, a temperature sensor, or a humidity sensor (e.g., the sensor module 176 in FIG. 1) so as to detect the user's momentum, the environment at the time of measuring a biological signal, and the like. The control unit 211 may generate second measurement information on the user's momentum, temperature, humidity, etc., detected by the measurement unit 239a, and may store the second measurement information in the recording unit 233a. The first measurement information and the second measurement information stored in the biological signal measurement device 200 (e.g., the storage unit 233a) are used as basic data capable of analyzing a health condition such as the user's physical strength.

Figure 3:
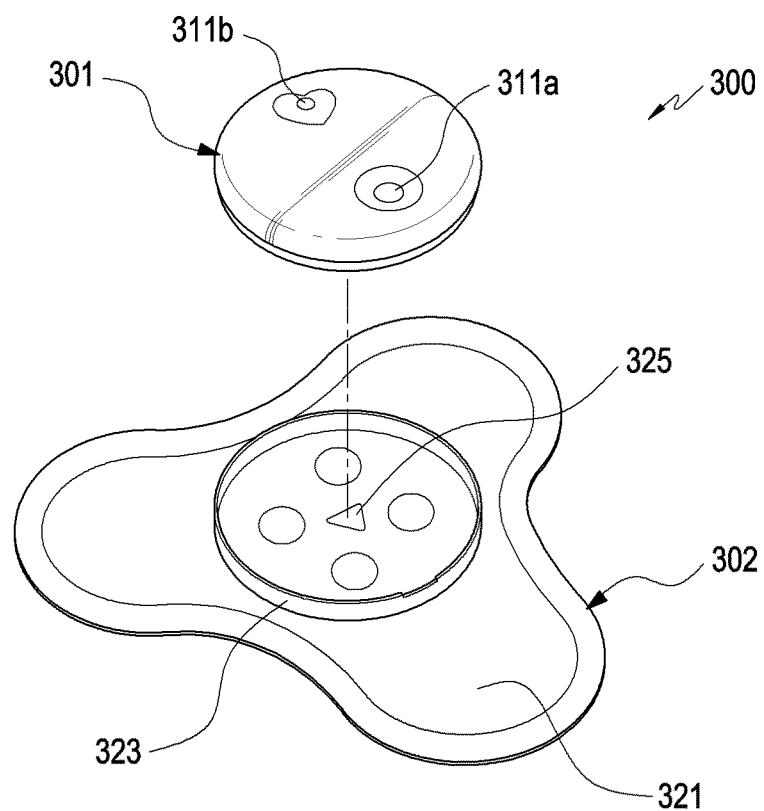
FIG. 3 is an exploded perspective view illustrating a biological signal measurement device according to certain embodiments.
Figure 4:
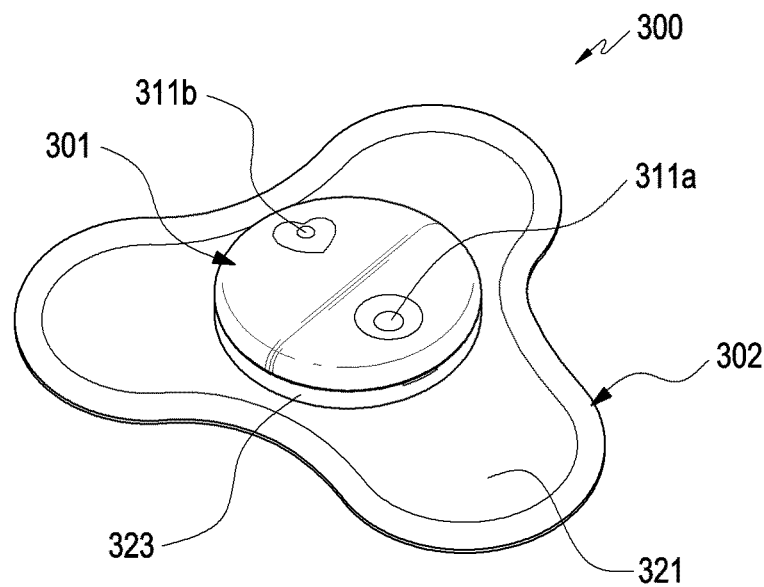
FIG. 4 is a perspective view illustrating a biological signal measurement device according to certain embodiments in the assembled state.

FIG. 3 is an exploded perspective view illustrating a biological signal measurement device 300 according to certain embodiments. FIG. 4 is a perspective view illustrating the biological signal measurement device 300 according to certain embodiments in the assembled state.

Referring to FIGS. 3 and 4, an electronic device (e.g., the electronic device 101 in FIG. 1) such as the biological signal measurement device 300 (e.g., the biological signal measurement device 200 in FIG. 2) may include a detachable housing (e.g., a module housing 301) and an attachment pad 302. According to an embodiment, the attachment pad 302 may provide a method for attaching the biological signal measurement device 300 to the user's body. In some embodiments, the attachment pad 302 may be limited as to the number of times it is capable of being attached to the user's body in consideration of attachment force or hygiene problems such as contamination and infection, and a medical institution may prescribe single use thereof in principle. The module housing 301 may include therein circuit devices for performing biological signal measurement, such as a control unit 201 and a power supply unit 202 in FIG. 2, and may be coupled to the attachment pad 302 by magnetic force. For example, when the attachment pad 302 is to be replaced due to a limit on the number of times of attachment, the measurement module (e.g., the module housing 301) may be used by being coupled to a new attachment pad.

According to certain embodiments, the bottom surface of the module housing 301 (e.g., the surface facing the attachment pad 302) is generally flat and the upper surface is formed in a domed shape. For example, the module housing 301 is capable of accommodating the above-described control unit, power supply unit, and the like therein by forming a dome-shaped internal space. According to an embodiment, the module housing 301 may include an operation unit 311a configured to operate a switch device or the like of a power supply unit (e.g., the power supply unit 202 in FIG. 2), and an output unit 311b configured to output light, an image, sound, or the like provided via a display unit (e.g., the display unit 237a in FIG. 2) to the outside. Since the operation unit 311a and the output unit 311b are disposed on the upper surface of the module housing 301, the module housing 301 may be exposed to the outside even when the module housing 301 is coupled to the attachment pad 302.

According to certain embodiments, the attachment pad 302 may include a pad body 321 made of a flexible sheet or the like and a coupling member 323 provided on one surface of the pad body 321. The coupling member 323 may be provided to enclose a part of the module housing 301, for example, the bottom surface of the module housing 301. For example, the coupling member 323 has a substantially circular fence shape protruding from the one surface of the pad body 321, so that the module housing 301 is capable of providing a certain degree of fixing force while guiding coupling.

According to certain embodiments, the biological signal measurement device 300 may include an alignment key structure to set the direction in which the module housing 301 is coupled to the attachment pad 302. For example, in the state of being aligned in a predetermined direction with respect to the attachment pad 302, the module housing 301 is capable of being stably coupled to the attachment pad 302 (e.g., the coupling member 323). In some embodiments, such an alignment key structure may be configured with a combination of a first alignment key (e.g., a first alignment key 633 of FIG. 7 to be described below) protruding from the bottom surface of the module housing 301 and a second alignment key (e.g., an alignment recess denoted by reference numeral "325") in a depressed shape in the coupling member 323. The alignment key structure described above may be designed in various shapes and positions, and may guide the module housing 301 in an intended direction for coupling to the attachment pad 302.

According to certain embodiments, an adhesive may be applied to the other surface of the pad body 321 (e.g., the surface opposite the surface on which the coupling member 323 is disposed). For example, the other surface of the pad body 321 (e.g., the bottom surface of the pad body 321, which is not visible in FIG. 3) may be attached to the user's body. For attachment to the user's body, the pad body 321 may be formed of a flexible sheet or the like, and may have various shapes to conform to the bending of the user's body. For example, the pad body 321 may be manufactured to be easily attached to the user's body in terms of the material and shape thereof. In some embodiments, the region of the pad body 321 to which the module housing 301 is coupled, for example, the coupling member 323, may have a certain degree of rigidity. For example, the pad body 321 may stably maintain the coupling state with the module housing 301 while being flexibly deformed to substantially correspond to the bending of the body.

According to certain embodiments, the module housing 301 or at least the bottom surface of the module housing 301 may have a regular polygonal or circular shape. The shape of the module housing is capable of providing an environment in which a larger number of electrodes (e.g., electrodes for biological signal detection or electric signal transmission) is capable of being disposed in a limited area (e.g., the area of the bottom surface of the module housing 301). In biological signal detection, as the number of electrodes is increased, the accuracy of measurement can be increased. For example, when at least a pair of electrodes among the plurality of electrodes is in contact with the user's body, it is possible to detect biological signals through the corresponding electrodes. In some embodiments, when a plurality of respective electrodes are in contact with the user's body, two arbitrarily selected electrodes may be set as leads. For example, when three electrodes are used for biological signal measurement, three pairs of electrode combinations (e.g., leads) are possible, and the detected information is capable of being diversified or improved in accuracy by detecting biological signals through each electrode combination.

According to certain embodiments, the electrodes disposed in the module housing 301 are capable of providing a path for transmitting a voltage or current signal or the like substantially corresponding to a detected biological signal, and a measurement electrode(s) to be in contact with the user's body may be provided on the attachment pad (e.g., on the other surface of the pad body 321). For example, the measurement electrodes may be electrically connected to the module housing 301 through wires provided inside the pad body 321 or the coupling member 323. Since the pad body 321 is capable of being flexibly deformed corresponding to the bending of the body, it is possible to provide an environment in which a sufficient interval can be secured between the measurement electrodes. The arrangement of the measurement electrodes, the electrical connection structure to the module housing 301, and the like will be described in more detail with reference to FIG. 12 or the like.

Figure 5:
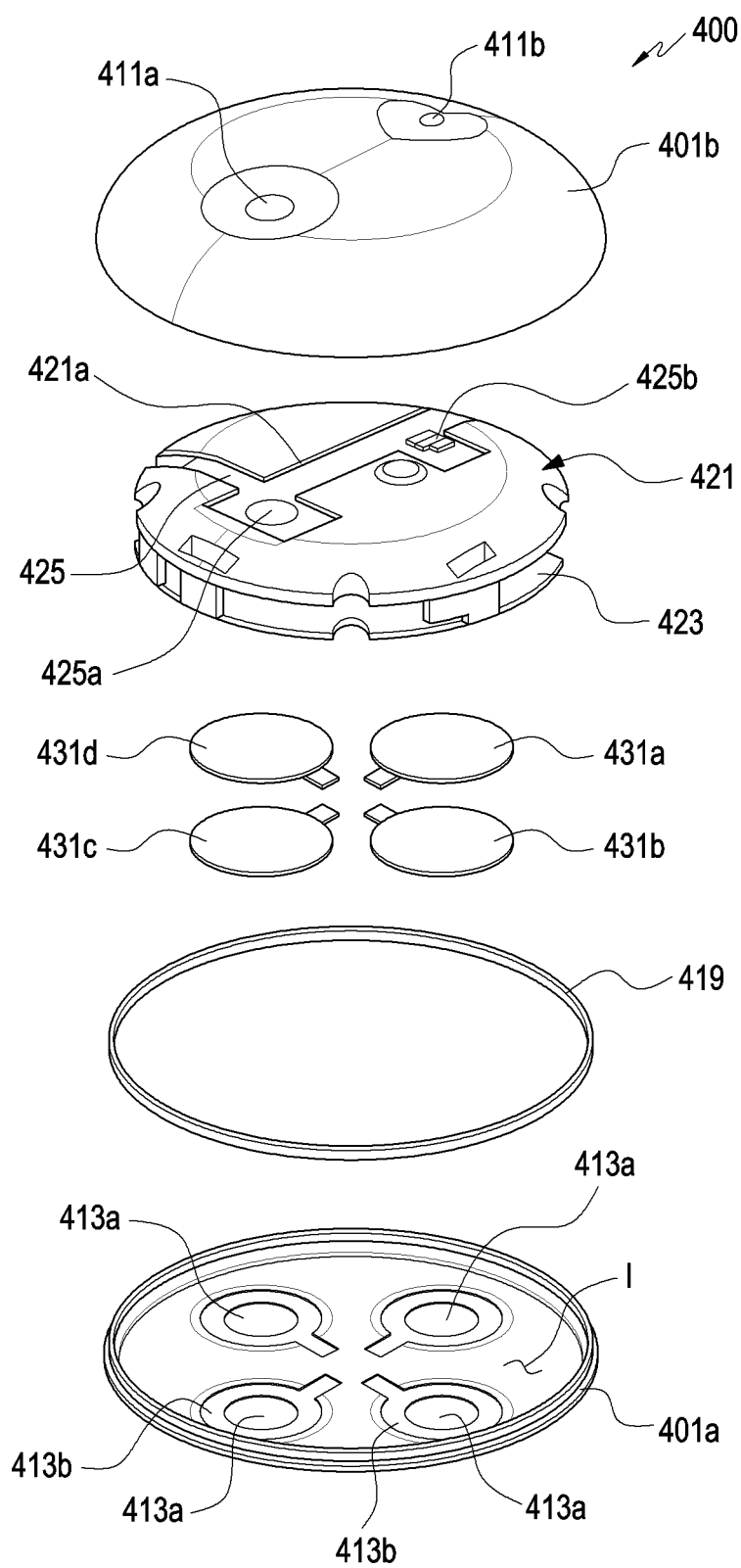
FIG. 5 is an exploded perspective view illustrating a measurement module of a biological signal measurement device according to certain embodiments.

FIG. 5 is an exploded perspective view illustrating a measurement module 400 of a biological signal measurement device according to certain embodiments.

Referring to FIG. 5, the measurement module 400 of the biological signal measurement device (e.g., the biological signal measurement device 300 in FIG. 3) according to certain embodiments may accommodate various circuit devices or the like in a space (e.g., the inner space of the module housing 301 in FIG. 3) formed by a combination of a first case member 401a and a second case member 401b, and may include a first electrode 431a, a second electrode 431b, a third electrode 431c, or a fourth electrode 431d exposed to the outer surface of the first case member 401a (e.g., the bottom surface of the module housing 301 of FIG. 3). In some embodiments, the fourth electrode 431d may be provided as a reference electrode for measuring a biological signal (e.g., electrocardiogram).

According to certain embodiments, the outer surface of the first case member 401a may form the bottom surface of the measurement module 400, and the first case member 401a may include a plurality of first openings 413a in order to dispose the first electrode 431a, the second electrode 431b, the third electrode 431c, and the fourth electrode 431d therein. Stepped surface 413b formed around the first openings 413a may be disposed in the inner surface I of the first case member 401a, and the edges of the first electrode 431a, the second electrode 431b, the third electrode 431c, and the fourth electrode 431d may be fixed to the stepped surfaces 413b. For example, the first electrode 431a, the second electrode 431b, the third electrode 431c, and the fourth electrode 431d may be mounted on or fixed to the inner surface I of the first case member 401a, and may be exposed to the outside of the measurement module 400 through the first openings 413a. In some embodiments, the first electrode 431a, the second electrode 431b, the third electrode 431c, and the fourth electrode 431d may be partially positioned to be substantially coplanar with the outer surface of the first case member 401a, and in other embodiments, the first electrode 431a, the second electrode 431b, the third electrode 431c, and the fourth electrode 431d may partially protrude from the outer surface of the first case member 401a by a predetermined height.

According to certain embodiments, the second case member 401b may include an operation unit 411a (e.g., the operation unit 311a in FIG. 3) configured to operate a switch device or the like, and an output unit 411b (e.g., the output unit 311b in FIG. 3) configured to output light or sound. According to an embodiment, the second case member 401b may provide a space that accommodates various circuit devices (e.g., the control unit 201 and the power source unit 202 in FIG. 2). For example, the second case member 401b may have a substantially polyhedral or domed shape, and the inner space may be closed when the first case member 401a is coupled to the second case member 401b.

According to certain embodiments, the measurement module 400 may include a support member 421 and a circuit board 423 disposed inside the second case member 401b. In an embodiment, the circuit board 423 is fixed on or above the inner surface of the second case member 401b via the support member 421. The circuit device (s) of the measurement module 400 may be mounted or disposed on the circuit board 423. According to an embodiment, the support member 421 may include a support structure on which the circuit board 423 is supported or fixed, and although not illustrated in the drawings, a battery (e.g., the battery 189 or 221 in FIG. 1 or FIG. 2) may be disposed between the circuit board 423 and the support member 421. For example, the circuit board 423 may be coupled to the support member 421 and may be disposed so as to partially surround the space in which the battery is mounted.

According to certain embodiments, the biological signal measurement device (e.g., the biological signal measurement device 300 in FIG. 3), for example, the measurement module 400, may include a flexible printed circuit board 425 extending from the circuit board 423. A switch member 425a or a light-emitting element 425b may be mounted on the flexible printed circuit board 425, and may be electrically connected to the circuit board 423 (e.g., the control unit 201 in FIG. 2). According to an embodiment, the flexible printed circuit board 425 may be mounted on the other surface of the support member 421 (e.g., the surface facing the second case member 401b in FIG. 5) and may be disposed such that the switch member 425a corresponds to the operation unit 411a or such that the light-emitting element 425b corresponds to the output unit 411b. For example, when viewed with reference to the support member 421, the flexible printed circuit board 425 may be disposed so as to be directed away from the bottom surface of the measurement module 400 (e.g., the outer surface of the first case member 401a) and to face the inner surface of the second case member 401b. According to an embodiment, in the other surface of the support member 421 (e.g., the surface facing the first case member 401a), a wiring recess 421a having a depth corresponding to the thickness of the flexible printed circuit board 425 (or deeper than the thickness of the flexible printed circuit board 425) may be provided. For example, in the state of being mounted on or fixed to the support member 421, the flexible printed circuit board 425 is capable of being protected from interference with other structures by being located in the wiring recess 421a.

According to certain embodiments, the switch member 425a may include a dome switch, a tact switch, or a touch sensor, and may be disposed to correspond to the operation unit 411a. For example, when the user operates the operation unit 411a, the switch member 425a may generate an on/off signal of the measurement module 400. According to the setting of the control unit or the memory (e.g., the control unit 201 or the storage unit 233a in FIG. 2) of the measurement module 400, the switch member 425a may generate a signal for changing the operation mode of the measurement module 400 or changing the output method of the display unit. In another embodiment, when the measurement module 400 includes a communication module (e.g., the communication unit 235a in FIG. 2), the measurement module 400 may transmit data relating to measured or stored biological information, or may reset the operation mode or the communication mode according to the presetting of a processor or the operation of the switch member 425a.

According to certain embodiments, the light-emitting device 425b is an example of an output unit that substantially forms the display unit 237a in FIG. 2, and may visually output the status information of the measurement module 400 or the results of biological signal detection by a combination of a color of light, a blinking signal, and the like. In some embodiments, the light-emitting element 425b may be replaced by a display or a sound output unit, or may be installed together with a display or a sound output unit. For example, the measurement module 400 may output operation state information or information on the results of biological signal detection or the like, not only through the color of light or a blinking signal, but also in the form of an image, a character, sound or the like.

According to certain embodiments, the second case member 401b may be coupled to face the first case member 401a in the state in which the support member 421 or the circuit board 423 is accommodated therein. For example, the space in which the circuit board 423 is accommodated may be substantially sealed by the first case member 401a and the second case member 401b. According to an embodiment, when coupling the first case member 401a and the second case member 401b, a fastening member such as a screw is fastened from the first case member 401a to sequentially penetrate the circuit board 423 and the support member 421 so as to be bound to the inner surface of the second case member 401b. According to another embodiment, in the state in which the first case member 401a and the second case member 401b are coupled to each other, the first electrode 431a, the second electrode 431b, the third electrode 431c, and the fourth electrode 431d may be positioned to face at least a part of the circuit board 423. Although not illustrated, the first electrode 431a, the second electrode 431b, the third electrode 431c, and the fourth electrode 431d may be electrically connected to a circuit device (e.g., the AFE 215 in FIG. 2) provided on the circuit board 423 via elastic bodies such as pogo pins and C-clips.

According to certain embodiments, the measurement module 400 is capable of blocking the introduction of foreign matter, moisture, or the like into the inner space (e.g., the inner space of the module housing 301 in FIG. 3) by including a first waterproofing member 419. For example, the first waterproofing member 419 may have a shape corresponding to the edge of the first case member 401a (e.g., an O-ring), and may be interposed between the first case member 401a and the second case member 401b. When the first case member 401a and the second case member 401b are bound together by the fastening member or the like, the first waterproofing member 419 may form a sealing structure or a waterproofing structure by being pressed to a certain degree between the first case member 401a and the second case member 401b.

According to an embodiment, the measurement module 400 may include a permanent magnet (e.g., a permanent magnet 535 in FIG. 6) so as to be coupled to an attachment pad (e.g., the attachment pad 302 in FIG. 3). The arrangement structure, such as a permanent magnet or the like, will be described with reference to FIG. 6.

Figure 6:
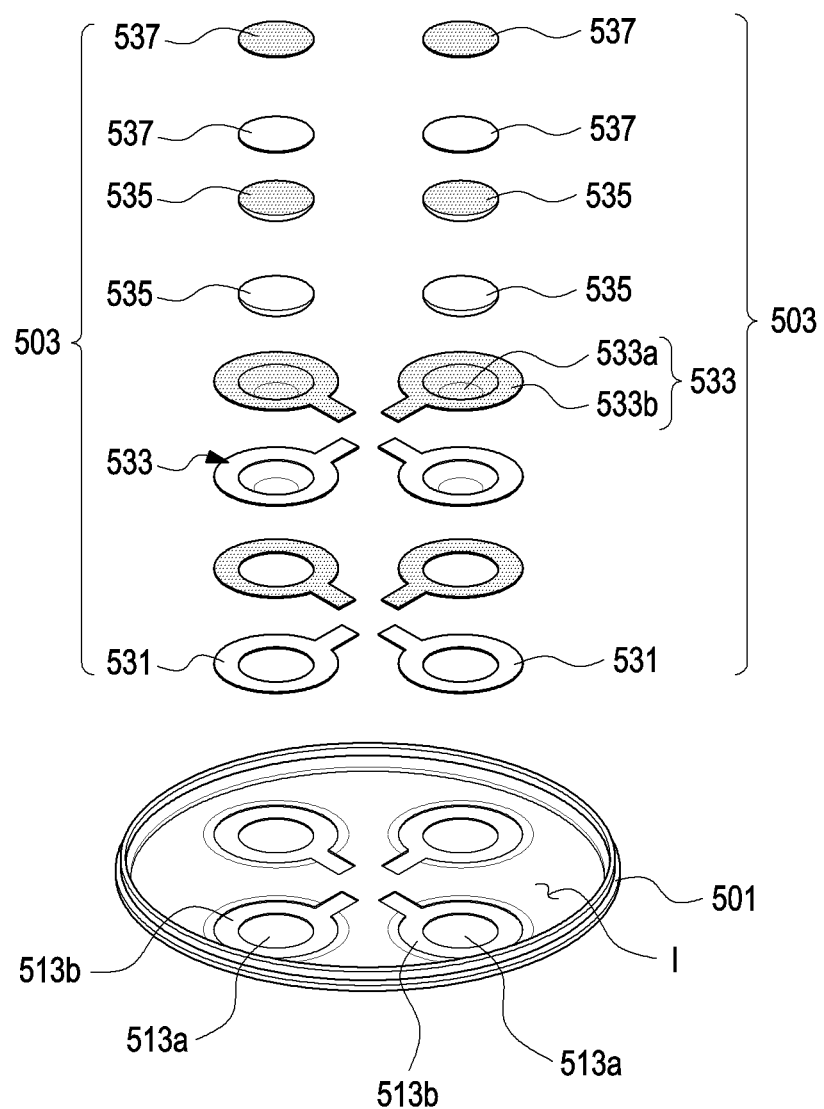
FIG. 6 is an exploded perspective view illustrating the arrangement of a first electrode in a measurement module of a biological signal measurement device according to certain embodiments.

FIG. 6 is an exploded perspective view illustrating the arrangement of electrodes 503 in a measurement module of a biological signal measurement device according to certain embodiments.

Referring to FIG. 6, the measurement module (e.g., the measurement module 400 in FIG. 6) of the biological signal measurement device described above may include a permanent magnet 535 disposed in at least one of the electrodes 503 (e.g., the first electrode 431a, the second electrode 431b, the third electrode 431c, and the fourth electrode 431d in FIG. 5). In some embodiments, the permanent magnets 535 may be disposed on respective ones of the electrodes 503 (e.g., the first electrode 431a, the second electrode 431b, the third electrode 431c, and the fourth electrode 431d in FIG. 5). For example, each of the electrodes 503 may include a first electrode plate 533 made of an electrically conductive material and a permanent magnet 535 accommodated in the first electrode plate 533. In an embodiment, the first electrode plate 533 may include an accommodation recess 533a formed in the inner surface thereof and a flange 533b provided around the accommodation recess 533a. For example, the permanent magnet 535 may be received in the accommodation recess 533a in the inner surface of the first electrode plate 533.

According to certain embodiments, the first electrode plate 533 may be made of a magnetic substance (e.g., stainless steel), and the permanent magnet 535 may be fixed in the accommodation recess 533a even if no separate fixing means is provided. For example, the permanent magnet 535 may be attached or fixed to the first electrode plate 533 or the accommodation recess 533a by magnetic force. In another embodiment, the electrode 503 is capable of more stably fixing the permanent magnet 535 in the accommodation recess 533a by further including a second electrode plate 537 coupled to the inner surface of the first electrode plate 533. The second electrode plate 537 may be made of a magnetic substance so as to be coupled to the first electrode plate 533 through the permanent magnet 535. In some embodiments, the second electrode plate 537 may be substantially directly coupled to the inner surface of the first electrode plate 533 so as to close the accommodation recess 533a and to fix the permanent magnet 535.

According to certain embodiments, the electrode(s) 503 may be mounted on the inner surface I of the case member 501 (e.g., the first case member 401a in FIG. 5). The case member 501 may include a plurality of first openings 513a, and stepped surfaces 513b, which are formed around respective ones of the first openings 513a, may be formed in the inner surface I thereof. The stepped surfaces 513b may be formed to substantially correspond to the flanges 533b. For example, the electrode(s) 503 may be fixed to the inner surface I of the case member 501 by coupling the flange(s) 533b to the stepped surface(s) 513b. When the electrodes 503, for example, the first electrode plates 533, are mounted on or fixed to the stepped surfaces 513b, the outer surfaces of the first electrode plates 533, which correspond to the accommodation recesses 533a, may be exposed to the outer surface of the case member 501 through the first openings 513a. The region exposed through each first opening 513a (e.g., a part of the outer surface of each first electrode plate 533) may be substantially coplanar with the outer surface of the case member 501, or may partially protrude from the outer surface of the case member 501.

According to certain embodiments, a biological signal measurement device (e.g., the biological signal measurement device 300 in FIG. 4 or the measurement module 400 in FIG. 5) may include first adhesive members 531 that attach the flanges 533b to the module housing (e.g., the module housing 301), for example, the case member 501. The first adhesive members 531 may include, for example, a piece of double-sided tape, and may attach the electrodes 503 (e.g., the first electrode plates 533) to the first openings 513a so as to seal the first openings 513a and form waterproofing structures. In an embodiment, the first adhesive members 531 may have a shape corresponding to the flanges 533b or the stepped surfaces 513b, and may substantially attach the flanges 533b to the stepped surfaces 513b.

According to certain embodiments, since the permanent magnets 535 are disposed in the electrodes 503, the structure of the measurement module (e.g., the module housing 301 in FIG. 3 or the measurement module 400 in FIG. 5) can be simplified or miniaturized. For example, since a separate structure to be coupled with an attachment pad (e.g., the attachment pad 302 of FIG. 3) is substantially unnecessary (e.g., since binding force is provided using the permanent magnet 535), it is possible to increase the utilization efficiency of the space inside the measurement module. When the utilization efficiency of the space inside the measurement module increases, it is easy to miniaturize at least the measurement module, and it is possible to dispose a larger-capacity battery in a measurement module of the same size.

In a specific embodiment, a structure using magnetic force (e.g., the permanent magnet 535) as a method for coupling the measurement module to the attachment pad is disclosed, but the disclosure is not limited thereto. The measurement module may be combined with the attachment pad through, for example, a snap-fit structure using a combination of a hook (or an elastic body) and a recess, a structure in which a lock-releasing button is combined with the snap-fit structure, and a rotational coupling structure (e.g., screw-coupling). As described above, the coupling structure between a measurement module and an attachment pad (e.g., the module housing 301 and the attachment pad 302 in FIG. 3) may be appropriately selected in consideration of the size (e.g., the utilization efficiency of the inner space), shape, or structural stability of a biological signal measurement device (e.g., the biological signal measurement device 300 in FIG. 3), the alignment direction of a measurement module, and the like.

Figure 7:
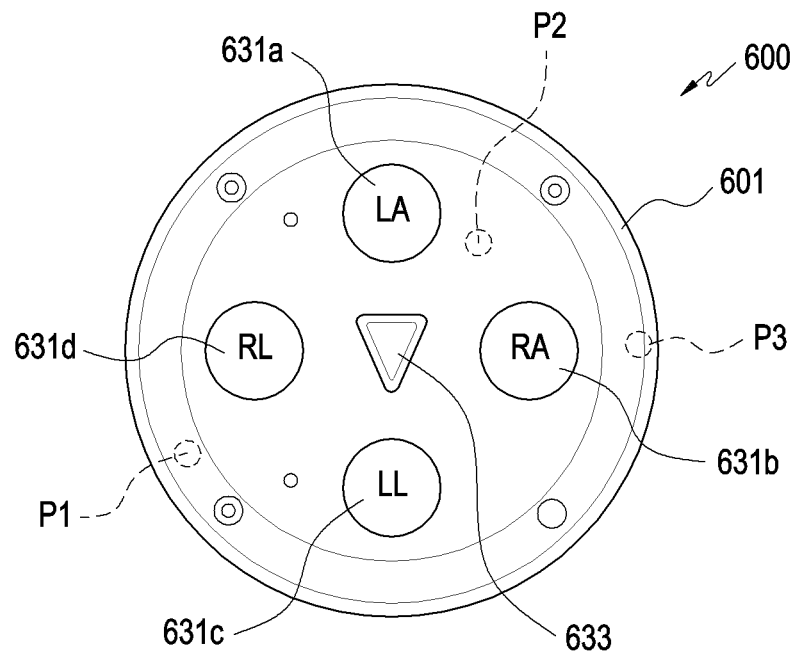
FIG. 7 is a bottom view illustrating a measurement module of a biological signal measurement device according to certain embodiments.
Figure 8:
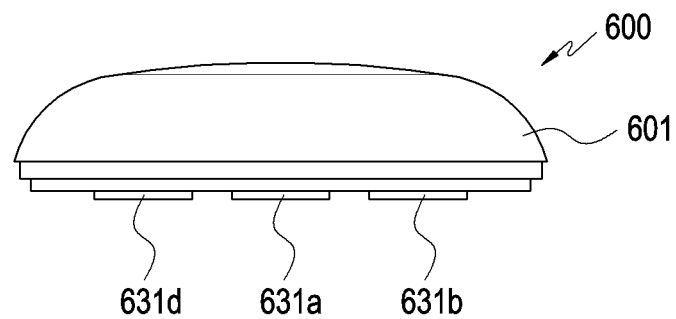
FIG. 8 is a side view illustrating a measurement module of the biological signal measurement device according to certain embodiments.

FIG. 7 is a bottom view illustrating a measurement module 600 of a biological signal measurement device according to certain embodiments. FIG. 8 is a side view illustrating the measurement module 600 of the biological signal measurement device according to certain embodiments.

Referring to FIGS. 7 and 8, the measurement module 600 (e.g., the module housing 301 in FIG. 3) of the biological signal measurement device according to certain embodiments may include a first electrode 631a, a second electrode 631b, a third electrode 631c, and a fourth electrode 631d (e.g., the first electrode 431a, the second electrode 431b, the third electrode 431c, and the fourth electrode 431d in FIG. 5) exposed to a first surface of the housing 601 (e.g., the outer surface of the first case member illustrated in FIG. 4 (e.g., the surface directed away from the inner surface I in the first case member 401a in FIG. 4), and a first alignment key 633 disposed on the first surface of the housing 601.

According to certain embodiments, a polygon may be formed by combining straight lines drawn to connect two adjacent electrodes among the first electrode 631a, the second electrode 631b, the third electrode 631c, and the fourth electrode 631d. For example, each of the first electrode 631a, the second electrode 631b, the third electrode 631c, and the fourth electrode 631d illustrated in FIG. 7 may be arranged to form one of vertices substantially in the shape of a square. In another embodiment, the first surface of the measurement module 600 is substantially in the shape of a circle and the first electrode 631a, the second electrode 631b, the third electrode 631c, and the fourth electrode 631d are arranged at equal angular intervals in the circumferential direction of the first surface of the measurement module 600.

As mentioned above, the number and arrangement of the first electrode 631a, the second electrode 631b, the third electrode 631c, and the fourth electrode 631d may vary. However, considering that the measurement module 600 has a rigid structure and is attached to the user's body, the area of the measurement module 600 (e.g., the area of the surface on which the first electrode 631a, the second electrode 631b, the third electrode 631c, and the fourth electrode 631d are disposed) may be limited. Therefore, the number and arrangement of the first electrode 631a, the second electrode 631b, the third electrode 631c, and the fourth electrode 631d may be appropriately selected in consideration of the area of the portion of the measurement module 600 (or the biological signal measurement device including the measurement module 600) that can be stably attached to the user's body.

According to certain embodiments, four electrodes (e.g., the first electrode 631a, the second electrode 631b, the third electrode 631c, and the fourth electrode 631d) are disposed, and a pair of arbitrarily selected electrodes may be combined to detect a biological signal. For example, the first electrode 631a, the second electrode 631b, the third electrode 631c, and the fourth electrode 631d are defined as an RL (Right Leg) electrode (e.g., the fourth electrode 631d), an LA (Left Arm) electrode (e.g., the first electrode 631a), an RA (Right Arm) electrode (e.g., the second electrode 631b), and an LL (Left Leg) electrode (e.g., the third angle corresponding to the third electrode 631c), the RL electrode may be utilized as a reference electrode, and each of an LL-RA electrode pair, an RA-LA electrode pair, and an LA-LL electrode pair may form a lead that detects a biological signal. In some embodiments, at least one of the electrode pairs listed above may detect a biological signal.

According to certain embodiments, an electronic device (e.g., a processor (e.g., processor 120 of FIG. 1) of the measurement module 600) may identify an input or request associated with an electrocardiogram measurement of a living body, may sense a signal using the first electrode 631a, the second electrode 631b, the third electrode 631c, and the fourth electrode 631d on the basis of the input or request, and may determine the sensed signal as a biological signal associated with the electrocardiogram. The processor of the electronic device may store at least a part or one of determined biological signal(s) in a memory (e.g., the memory 130 of FIG. 1) as at least a piece of measurement information on an electrocardiogram measurement. In some embodiments, at least a piece of the measurement information on an electrocardiogram measurement may be transmitted to another electronic device (e.g., the electronic device 102 or 104 in FIG. 1) or stored in a server (the server 108 in FIG. 1) through, for example, a communication module (e.g., the communication module 190 in FIG. 1 or the communication unit 235a in FIG. 2).

According to certain embodiments, some of the electrode pairs listed above may detect a biological signal, and the remaining electrode pairs may output a current signal or the like that stimulates the body. The "current signal that stimulates the body" may be provided for a treatment purpose. In another embodiment, when the "current signal that stimulates the body" may interfere with biological signal detection, current signals for biological signal detection and body stimulation may be alternatively or periodically alternately output.

In the embodiment, although it is described that "the first electrode, the second electrode, the third electrode, and the fourth electrode of the measurement module detect a biological signal", it is noted that the first electrode 631a, the second electrode 631b, the third electrode 631c, and the fourth electrode 631d are substantially a part of a path for transmitting a voltage or current signal corresponding to a detected biological signal. For example, a measurement electrode(s) (e.g., a third wiring electrode 831c in FIG. 12) of an attachment pad, which will be described later, actually comes into contact with the user's body to detect a biological signal, and the measurement electrode may be electrically connected to one of the first electrode 631a, the second electrode 631b, the third electrode 631c, and the fourth electrode 631d. In another embodiment, the "measurement electrodes" may be interpreted to mean including the first electrode, the second electrode, the third electrode, and the fourth electrode or the third wiring electrode 831c of FIG. 12, or to mean including a wiring path (e.g., the second wiring electrode 831b in FIG. 12) connecting the first electrode, the second electrode, the third electrode, and the fourth electrode and the third wiring electrode 831c. In the following description, "the electrodes that detect a biological signal" will be described again. However, as described above, an electrode in direct contact with the user's body and an electrode not in contact with the user's body may be easily distinguished through the entire description of embodiments, reference drawings, respective embodiments, and the like.

According to certain embodiments, the first alignment key 633 may establish a direction for coupling the measurement module 600 to an attachment pad (e.g., the attachment pad 302 in FIG. 3). The first alignment key 633 may have a polygonal shape (e.g., that of an isosceles triangle) that protrudes from a first surface (e.g., the bottom surface) of the measurement module 600 and is directional. The first alignment key 633 may be engaged with a second alignment key (e.g., the alignment recess 325 in FIG. 3) formed on a coupling member. For example, the second alignment key formed on the coupling member may have a shape corresponding to the first alignment key 633, and the measurement module 600 may be coupled with the coupling member in the direction in which the first alignment key 633 and the second alignment key of the coupling member are engaged with each other.

According to certain embodiments, the first alignment key 633 and the corresponding second alignment key may be provided in various shapes and positions. For example, the first alignment key 633 of the measurement module 600 may be formed in a recess shape, and the second alignment key formed on the coupling member may be formed in a protrusion shape. In another embodiment, the first alignment key 633 or the second alignment key may have a right-triangular shape. In another embodiment, when the first surface of the measurement module 600 is a regular polygonal or circular shape, the first alignment key 633 may be positioned at any location other than the center (e.g., a position indicated by "P1", "P2", or "P3" on the first surface of the measurement module 600). In another embodiment, when each of the first electrode 631a, the second electrode 631b, the third electrode 631c, and the fourth electrode 631d is connected to any of the third wiring electrodes 831c of FIG. 12, the first alignment key 633 may have a regular polygonal shape corresponding to the number of the electrodes 631a, 631b, 631c, 631d. For example, when four electrodes, i.e., the first electrode 631a, the second electrode 631b, the third electrode 631c, and the fourth electrode 631d are disposed in the measurement module 600 and an electrode (e.g., the fourth electrode 631d) is connected to any of the third wiring electrodes among the third wiring electrodes 831c, the first alignment key 633 may have a square shape.

Figure 9:
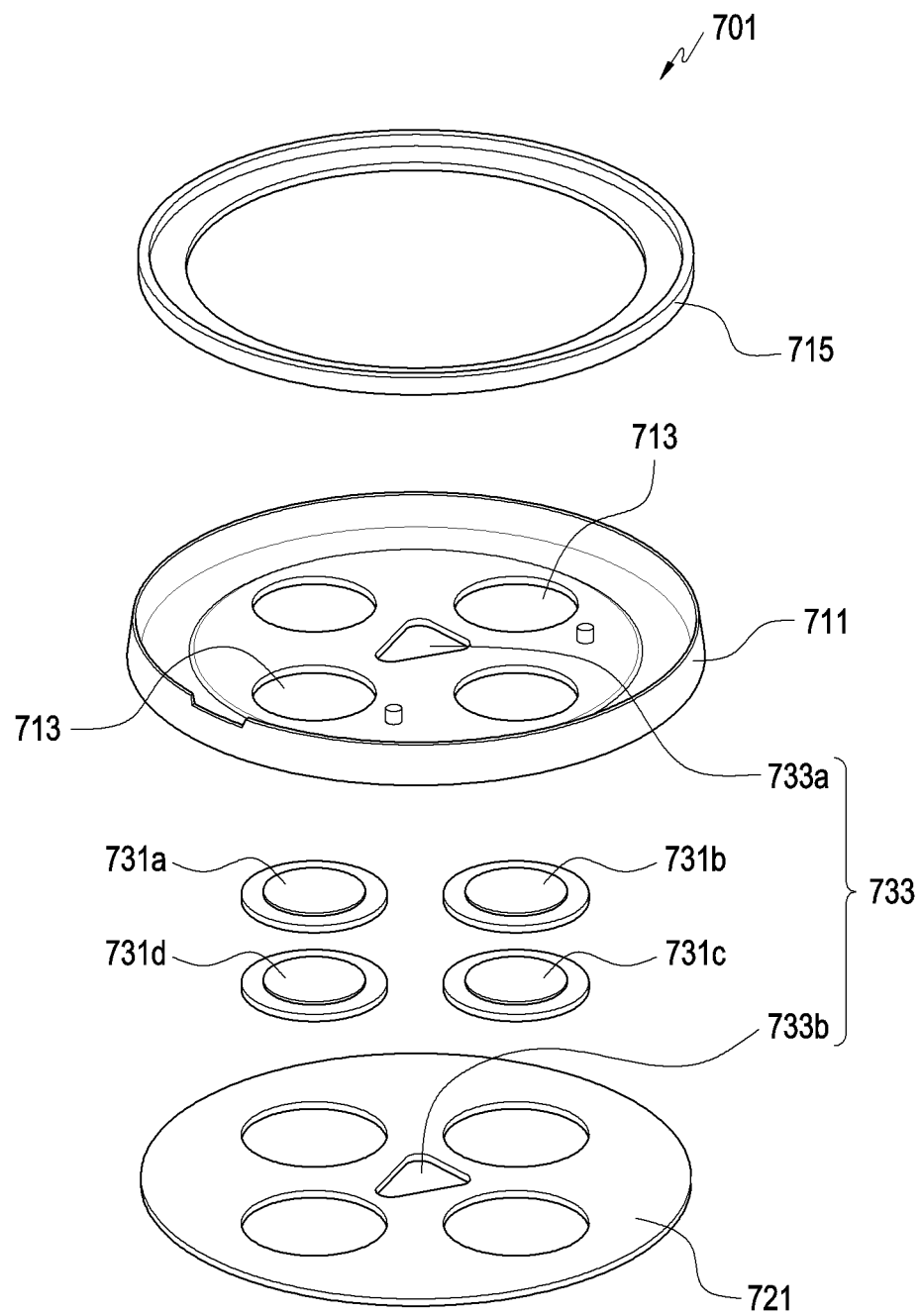
FIG. 9 is an exploded perspective view illustrating a coupling member in an attachment pad of a biological signal measurement device according to certain embodiments.
Figure 10:
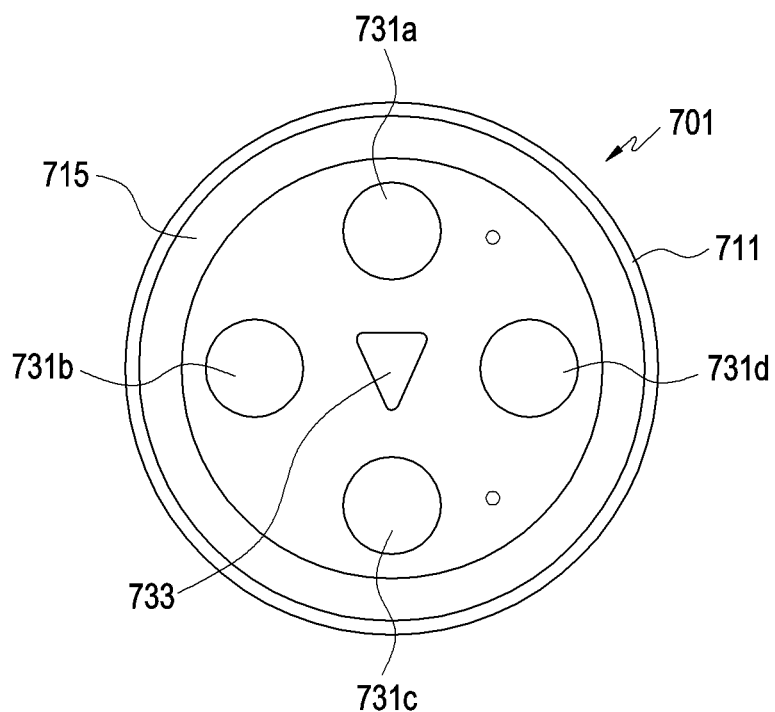
FIG. 10 is a plan view illustrating a coupling member in an attachment pad of a biological signal measurement device according to certain embodiments.
Figure 11:
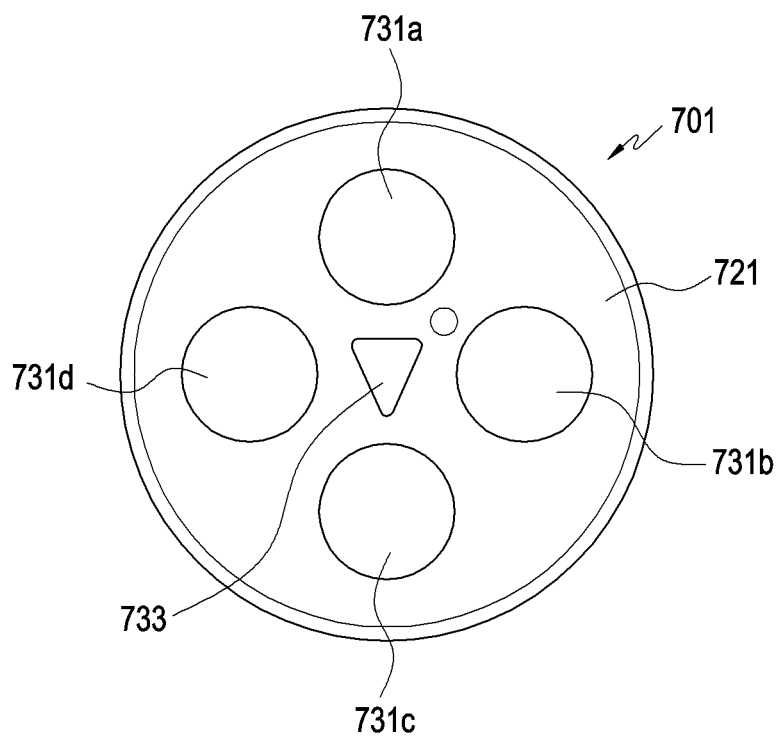
FIG. 11 is a bottom view illustrating a coupling member in an attachment pad of a biological signal measurement device according to certain embodiments.

FIG. 9 is an exploded perspective view illustrating a coupling member 701 in an attachment pad of a biological signal measurement device according to certain embodiments. FIG. 10 is a plan view illustrating the coupling member 701 in the attachment pad of the biological signal measurement device according to certain embodiments. FIG. 11 is a bottom view illustrating the coupling member 701 in the attachment pad of the biological signal measurement device according to certain embodiments.

As described with reference to FIG. 3, the coupling member (e.g., the coupling member 323 of FIG. 3) of the biological signal measurement device according to certain embodiments is a part of the attachment pad (e.g., the attachment pad 302 in FIG. 3), and may be mounted on the first surface (e.g., a first surface F1 in FIG. 13) of the pad body (e.g., the pad body 321 in FIG. 3). Referring to FIG. 9, the coupling member 701 (e.g., the coupling member 323 in FIG. 3) may be provided in a shape that encloses a portion of the measurement module (e.g., the module housing 301 in FIG. 3 or the measurement module 400 in FIG. 5). In an embodiment, the coupling member 701 may include a seating plate 711 and a second waterproofing member 715.

According to certain embodiments, the coupling member 701 may further include first to fourth terminals 731a to 731d, which correspond to respective ones of the first electrode, the second electrode, the third electrode, and the fourth electrode (e.g., the first electrode 431a, the second electrode 431b, the third electrode 431c, and the fourth electrode 431d in FIG. 5) of the measurement module, and a second adhesive member 721 that attaches the seating plate 711 to the pad body. As will be described later, the first to fourth terminals 731a to 731d may be electrically connected to a first wiring electrode (e.g., the first wiring electrode 831a in FIG. 12) disposed substantially in the pad body, or may be a part of the first wiring electrode. The second adhesive member 721 may include a piece of double-sided tape disposed or attached to a first surface (e.g., the first surface F1 in FIG. 13) of the pad body.

According to certain embodiments, the seating plate 711 has a shape corresponding to at least a portion (e.g., the bottom surface) of the measurement module (e.g., the measurement module 400 in FIG. 5), and may surround at least a part of the side surface of the measurement module by including a fence structure formed at the edge thereof. For example, the seating plate 711 may have a shape that encloses or receives a portion of the measurement module. According to an embodiment, the second waterproofing member 715 is generally in the shape of a closed curve corresponding to the edge of the seating plate 711, and may be mounted inside a space in which the measurement module is accommodated (e.g., a space formed by a fence structure). For example, when the measurement module is accommodated in the seating plate 711 (or when the measurement module is coupled with the seating plate), the second waterproofing member 715 is capable of blocking the introduction of foreign matter, moisture, or the like between the seating plate 711 and the measurement module (e.g., between the module housing 301 and the coupling member 323 in FIG. 3).

According to certain embodiments, second openings 713 may be formed through the seating plate 711 in the space in which the measurement module is accommodated. The second openings 713 may be formed substantially at positions corresponding to the first to fourth electrodes (e.g., the first electrode 431a, the second electrode 431b, the third electrode 431c, and the fourth electrode 431d in FIG. 5) of the measurement module. In another embodiment, a first alignment hole 733a may be formed through the seating plate 711 in the space in which the measurement module is accommodated. The first alignment hole 733a may include at least a portion of a second alignment key 733 (e.g., the alignment recess 325 in FIG. 3) corresponding to the first alignment key of the measurement module (e.g., the first alignment key 633 in FIG. 7).

According to certain embodiments, the first to fourth terminals 731a-731d may be disposed in respective ones of the second openings 713. For example, a plurality of the first to fourth terminals 731a to 731d may be mounted on the bottom surface of the seating plate 711 to be exposed to the space in which the measurement module is accommodated through the second openings 713. In an embodiment, the first to fourth terminals 731a to 731d may be mounted on the seating plate 711 via other adhesive members to close the second openings 713. For example, the first to fourth terminals 731a to 731d may be mounted on the seating plate 711 via other adhesive members to form waterproofing structures on the second openings 713. In another embodiment, when the measurement module (e.g., the measurement module 400 in FIG. 5) is coupled to the coupling member 701, each of the first to fourth terminals 731a to 731d may be in electrical contact with one of the electrodes of the measurement module (e.g., the first electrode 431a, the second electrode 431b, the third electrode 431c, and the fourth electrode 431d in FIG. 5).

According to certain embodiments, the first to fourth terminals 731a to 731d may include a conductive material or a magnetic substance. As described above, each of the first to fourth terminals 731a to 731d may be made of a conductive material, and may be in electrical contact with one of the electrodes of the measurement module (e.g., the first electrode 431a, the second electrode 431b, the third electrode 431c, and the fourth electrode 431d in FIG. 5). According to an embodiment, the first to fourth terminals 731a to 731d may be made of a magnetic material, and may generate an attractive force with the first electrode, the second electrode, the third electrode, and the fourth electrode of the measurement module using the magnetic force of a permanent magnet (e.g., the permanent magnet 535 in FIG. 6). For example, the first to fourth terminals 731a-731d may couple and fix the measurement module (e.g., the module housing 301 in FIG. 3 or the measurement module 400 in FIG. 5) to the seating plate 711 using the magnetic force while providing an electrical connection.

According to certain embodiments, the second adhesive member 721 may be formed of a piece of double-sided tape or the adhesive applied to the bottom surface of the seating plate 711. The second adhesive member 721 may attach the seating plate 711 to a pad body (e.g., the pad body 321 in FIG. 3). In an embodiment, the second adhesive member 721 may include a second alignment hole 733b aligned with the first alignment hole 733a. For example, the first alignment hole 733a and the second alignment hole 733b may be combined to form a second alignment key (e.g., the alignment recess 325 in FIG. 3) corresponding to a first alignment key (e.g., the first alignment key 633 in FIG. 7). In another embodiment, the second adhesive member 721 may be provided on a first surface of the pad body (e.g., the first surface F1 in FIG. 13) rather than on the seating plate 711, and in some embodiments, the second adhesive member 721 may be provided on each of the seating plate 711 and the pad body. A pad body in a biological signal measurement device according to certain embodiments will be described with reference to FIG. 12 and the like.

Figure 12:
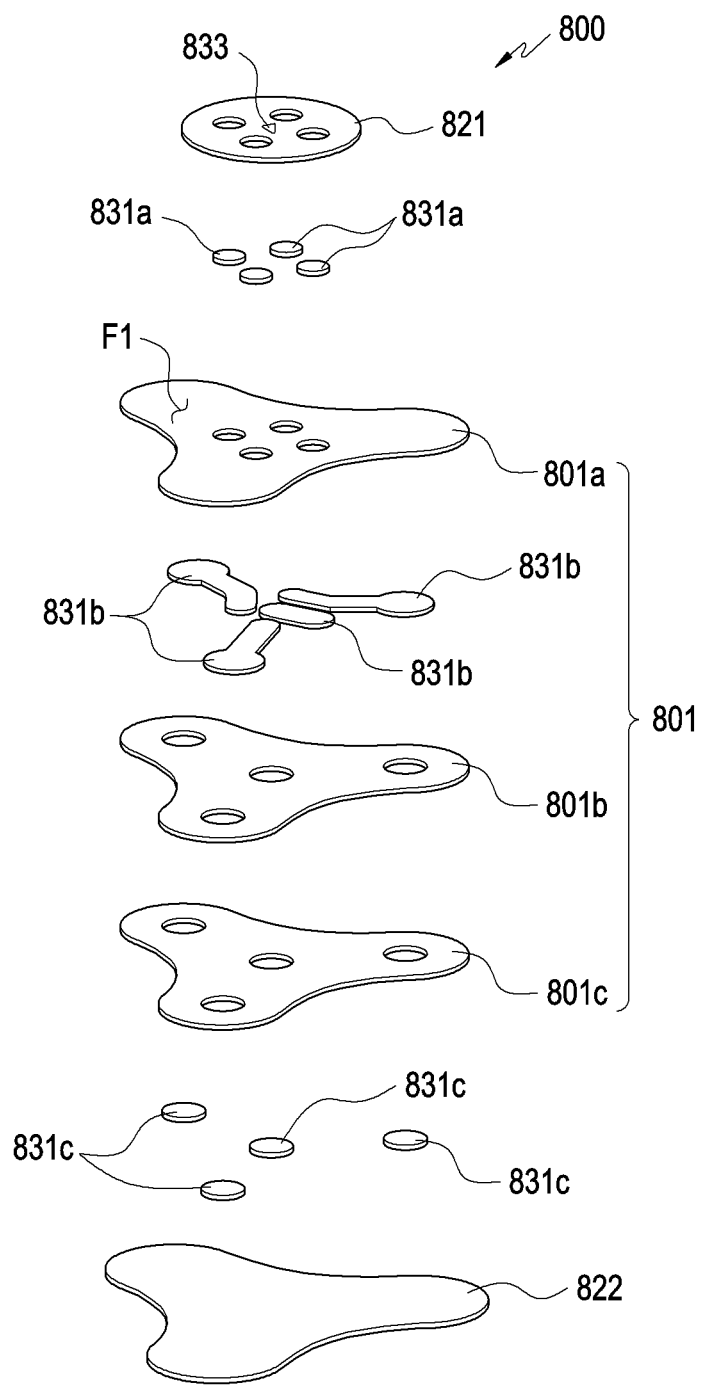
FIG. 12 is an exploded perspective view illustrating a pad body in an attachment pad of a biological signal measurement device according to certain embodiments.
Figure 13:
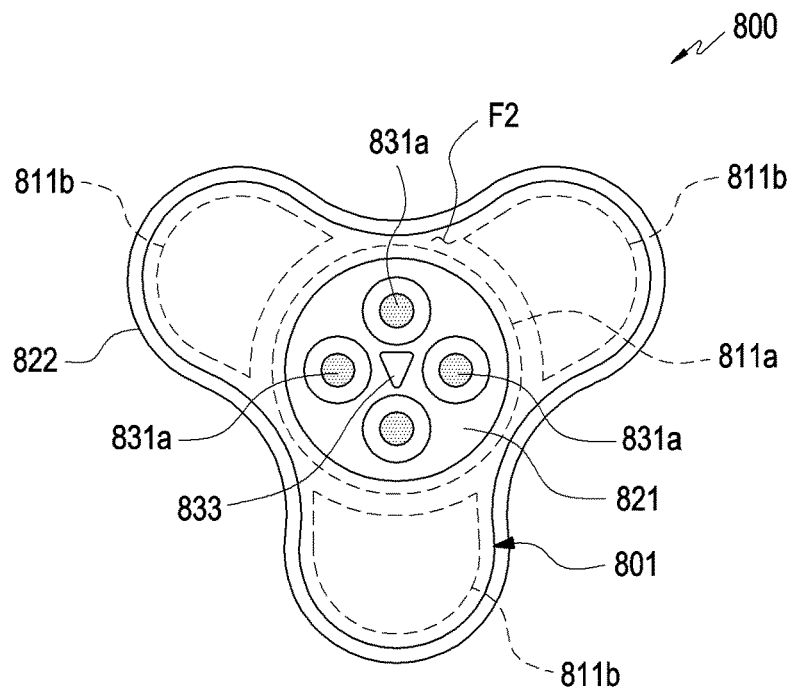
FIG. 13 is a plan view illustrating a pad body in an attachment pad of a biological signal measurement device according to certain embodiments.

FIG. 12 is an exploded perspective view illustrating a pad body 801 in an attachment pad of a biological signal measurement device according to certain embodiments. FIG. 13 is a plan view illustrating the pad body 801 in the attachment pad of the biological signal measurement device according to certain embodiments.

Referring to FIGS. 12 and 13, the pad body 801 of the attachment pad 800 (e.g., the pad body 321 in FIG. 3) may be made of a sheet or the like that can be flexibly deformed to correspond to the bending of the body, and is capable of completing the attachment pad 800 (e.g., attachment pad 302 in FIG. 3) with the coupling member 701 illustrated in FIG. 9 and the like. In an embodiment, the attachment pad 800 may include an elastic material. It is noted that FIGS. 12 and 13 illustrate the attachment pad 800 in the state in which the coupling member is omitted. The pad body 801 may include a base sheet 801a, a plurality of adhesive layers 801b and 801c, a measurement electrode(s), a wiring structure, and the like.

According to certain embodiments, the base sheet 801a is a flexible sheet that substantially forms the outer shape of the pad body 801, and is capable of concealing the measurement electrode(s) or the wiring structure so as to prevent the same from being exposed to the outside. In some embodiments, a second adhesive member 821 (e.g., the second adhesive member 721 in FIG. 9) may be provided on the upper surface of the base sheet 801a (e.g., the first surface F1 of the pad body). It has been described that the second adhesive member 821 may be provided on one or each of the coupling member 701 and the pad body 801 of FIG. 9. In some embodiments, when the second adhesive member 821 includes a second alignment hole 833 (e.g., the second alignment hole 733b in FIG. 9), the second alignment hole 833 may have a recessed shape closed in the direction in which it is attached to the base sheet 801a. According to an embodiment, the base sheet 801a may be made of a single-sided sticker. For example, an adhesive for fixing the wiring structure or the like may be applied to the bottom surface of the base sheet 801a.

According to certain embodiments, the plurality of adhesive layers may include a first adhesive layer 801b and a second adhesive layer 801c. In an embodiment, the first adhesive layer 801b may include a piece of double-sided tape directly attached to the bottom surface of the base sheet 801a. The above-mentioned wiring structure (e.g., a second wiring electrode 831b to be described later) and the like may be at least partially fixed between the base sheet 801a and the first adhesive layer 801b. In another embodiment, the second adhesive layer 801c may include a pressure-sensitive adhesive applied to the first adhesive layer 801b, and may directly attach the pad body 801 or a biological signal measurement device (e.g., the biological signal measurement device 300) to the user's body. For example, the second adhesive layer 801c may be an adhesive layer to be in direct contact with the user's body.

According to certain embodiments, the pad body 801 may further include a low-adhesion protective film 822. The low-adhesion protective film 822 is a film attached to the second adhesive layer 801c and is capable of preventing pollution of the second adhesive layer 801c in the course of manufacturing, circulating or storing the pad body 801 or the attachment pad 800. For example, when the attachment pad 800 is actually used, the low-adhesion protective film 822 may be removed from the pad body.

According to certain embodiments, the pad body 801 may include a coupling portion 811a and extension portions 811b. According to an embodiment, the coupling portion 811a means the region in which a coupling member (e.g., the coupling member 701 in FIG. 9) is disposed, and the second adhesive member 821 may be disposed on the coupling portion 811a. The extension portions 811b may extend from the coupling portion 811a in different directions, respectively. Each of the extension portions 811b may be provided as a region in which one of measurement electrodes (e.g., the third wiring electrodes 831c to be described later) is disposed. For example, the extension portions 811b are capable of improving accuracy or the like in biological signal detection by securing an interval between the measurement electrodes.

According to certain embodiments, the wiring structure may include first wiring electrodes 831a and second wiring electrodes 831b, and is capable of electrically connecting the measurement electrode(s) (e.g., a third wiring electrode 831c to be described later) to a measurement module (e.g., the measurement module 400 in FIG. 5). According to an embodiment, the first wiring electrodes 831a may be disposed in the through holes formed in the base sheet 801a or the second adhesive member 821, and may be in electrical contact with or may be attached to terminals (e.g., the first to fourth terminals 731a to 731d in FIG. 9). For example, the second electrodes 831c may have a double-sided tape structure (e.g., adhesiveness) and may be conductive. For example, the first wiring electrodes 831a may be disposed in the coupling portion 811a. As described above, each of the first wiring electrodes 831a may be a portion of one of the above-mentioned first to fourth terminals (e.g., the first to fourth terminals 731a to 731d in FIG. 9), or each of the first to fourth wiring terminals may be provided on a portion of one of the first wiring electrodes 831a. According to another embodiment, the second wiring electrodes 831b may be made of silver or silver chloride and may have conductivity and a certain degree of flexibility. The second wiring electrodes 831b may extend from respective ones of the first wiring electrodes 831a. In some embodiments, one end of some of plurality of the second wiring electrodes 831b may be positioned on one of the extension portions 811b, and one end of the other of the plurality of the second wiring electrodes 831b may be positioned on the coupling portion 811a. According to an embodiment, at least a part of the wiring structure, for example, the third wiring electrodes 831c, may be disposed between the base sheet 801a and the first adhesive layer 801b.

According to certain embodiments, when the measurement module (e.g., the measurement module 400 in FIG. 5) includes four electrodes, such as the first electrode 431a, the second electrode 431b, the third electrode 431c, and the fourth electrode 431d, three extension portions 811b may be provided. The number of first wiring electrodes 831a or third wiring electrodes 831c may correspond to the number of first to fourth electrodes of the measurement module (e.g., the first electrode 431a, the second electrode 431b, the third electrode 431c, and the fourth electrode 431d in FIG. 5). According to an embodiment, some of the second wiring electrodes 831b may extend from any one of the first wiring electrodes 831a in the coupling portion 811a, and the end of each of the second wiring electrodes 831b may be positioned on one of the extension portions 811b. The third wiring electrodes 831c, each having an end positioned on one of the extension portions 811b, may be connected to the LL (Left Leg) electrode, the RA (Right Arm) electrode, and the LA (Left Arm) electrode, which form a measurement lead, among the first electrode, the second electrode, the third electrode, and the fourth electrode of the measurement module (e.g., the first electrode 631a, the second electrode 631b, the third electrode 631c, and the fourth electrode 631d in FIG. 7). For example, the second wiring electrodes 831b (e.g., the measurement electrodes), each having an end positioned on one of the extension portions 811b, is capable of transmitting a substantially detected biological signal or a voltage or current signal corresponding to the detected biological signal. According to another embodiment, any one of the second wiring electrodes 831b may extend from one of the first wiring electrodes 831a, and an end of the second wiring electrode 831b may be positioned in the coupling portion 811a. For example, any one of the third wiring electrodes 831c may be positioned in the coupling portion 811a, and may be connected to the reference electrode (e.g., the fourth electrode 631d or the RL electrode in FIG. 7) among the first electrode, the second electrode, the third electrode, and the fourth electrode of the measurement module. In an embodiment, the end of the second wiring electrode 831b connected to the reference electrode or the third wiring electrode 831c connected to the reference electrode may be positioned in the center of the coupling portion 811a.

According to certain embodiments, the measurement electrode(s) provided in the pad body 801 may include the third wiring electrodes 831c, which are respectively provided at the ends of the second wiring electrodes 831b. The third wiring electrodes 831c may be exposed to the outside on a second surface directed away from the first surface F1 of the pad body 801 (e.g., on the second adhesive layer 801c). For example, the third wiring electrodes 831c may be exposed to the outside of the attachment pad 800 or the pad body 801 in a direction different from that of the first terminal 731a, the second terminal 731b, the third terminal 731c, or the fourth terminal 731d (e.g., the opposite direction) in FIG. 10.

According to certain embodiments, when the second adhesive layer 801c is attached to the user's body (skin), the third wiring electrode(s) 831c may be in direct contact with the user's body. The third wiring electrode(s) 831c may be made of a conductive hydrogel and may stably maintain contact with the user's body. In an embodiment, a biological signal may be detected by the third wiring electrode(s) 831c and may be transmitted to a measurement module (e.g., the first electrode 431a, the second electrode 431b, the third electrode 431c, and the fourth electrode 431d in FIG. 5) via the second wiring electrode(s) 831b and the first wiring electrode(s) 831a (or the first to fourth terminals 731a to 731d in FIG. 9).

According to certain embodiments, since the third wiring electrodes 831c are disposed on respective ones of the extension portions 811b, the third wiring electrodes 831c may be arranged with a larger interval therebetween than the first wiring electrodes 831a located in the coupling portion 811a or the first electrode 631a, the second electrode 631b, the third electrode 631c, and the fourth electrode 631d of FIG. 7. For example, the attachment pad 800 is capable of securing sufficient space between the measurement electrodes (e.g., the third wiring electrodes 831c) so as to create an environment capable of stably detecting a biological signal. In an embodiment, any one of the third wiring electrodes 831c may be located in the center of the coupling portion 811a. For example, any one of the third wiring electrodes 831c may be disposed on an end of the second wiring electrode located in the coupling portion 811a among the second wiring electrodes 831b and may be electrically connected to the reference electrode of the measurement module (e.g., the RL electrode in FIG. 7). In contact with the body of a user or a patient, a measurement electrode (e.g., one of the third wiring electrodes 831c) connected to the reference electrode (e.g., the fourth electrode 631d in FIG. 7) may be disposed at the same interval with respect to the remaining third wiring electrodes.

Figure 14:
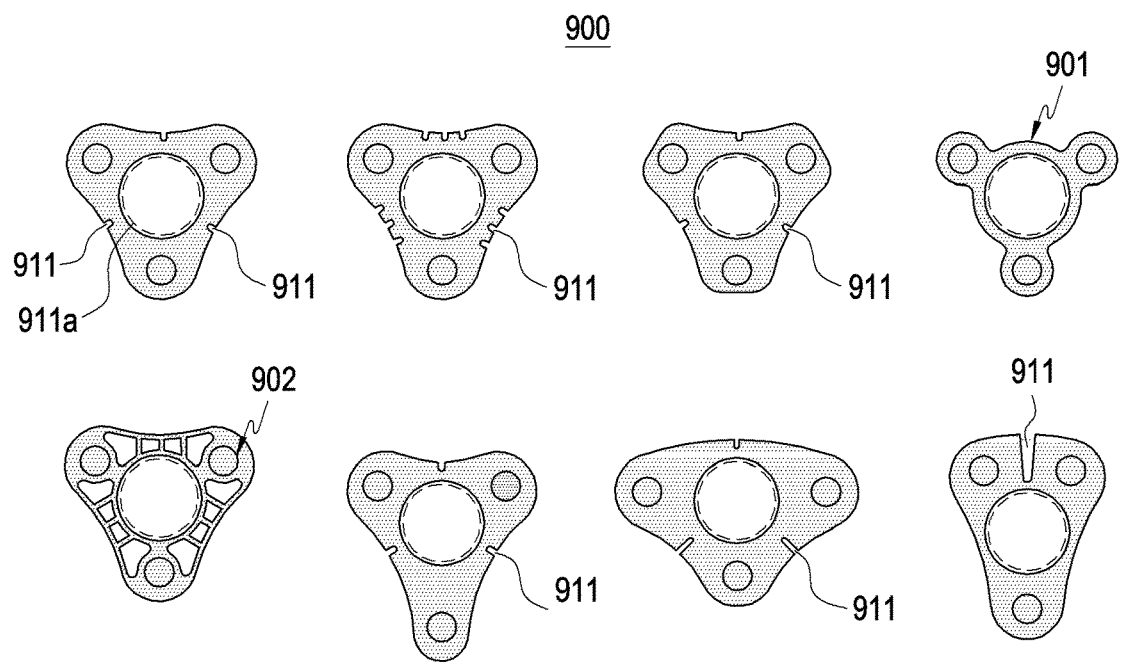
FIG. 14 illustrates various shapes of an attachment pad of a biological signal measurement device according to certain embodiments.

FIG. 14 illustrates various shapes of an attachment pad 900 of a biological signal measurement device according to certain embodiments.

Referring to FIG. 14, the shapes of the attachment pad(s) 900 (e.g., the attachment pad 800 in FIG. 13), for example, the extension directions or lengths of the extension portions (e.g., the extension portions 811b in FIG. 13), may be various. In an embodiment, an attachment pad(s) having a shape substantially based on a regular triangle may be attached to a portion in which the bending of the body is slight. In another embodiment, in a portion to which the attachment pad(s) having a shape based on a regular triangle is difficult to stably attach (e.g., in a valley portion between the breasts or a portion below a rib), an attachment pad having a shape generally based on the letter "T" or "Y" may be easily attached. In the attachment pads having various shapes as described above, the structure of the coupling portion 911a may be substantially the same as the coupling member 701 in FIG. 9 or the coupling portion 811a in FIG. 13. For example, even if the shapes of the attachment pads 900 are different, the attachment pads may be coupled to a measurement device (e.g., the measurement module 400 in FIG. 5) so as to implement a biological signal measurement device (e.g., the biological signal measurement device 300 in FIG. 3).

According to certain embodiments, the attachment pad(s) may include at least one slit 911 so as to be stably attached to a bending portion of a body. For example, the slit(s) 911 may improve the flexibility of the attachment pad(s) 900. In some embodiments, the area of the attachment pad 900 (e.g., the pad body 801 in FIG. 13) may be reduced so as to improve the flexibility of the attachment pad. For example, as in the attachment pad indicated by reference numeral "901", extension portions (e.g., the extension portion 811b in FIG. 13) may be formed to have a minimum area or a shape in which a third electrode or a fourth electrode (e.g., the second wiring electrode 831b or the third wiring electrode 831c in FIG. 12) may be disposed. In another embodiment, it is possible to improve the flexibility of the attachment pad by partially removing unnecessary portions of the pad body (e.g., the pad body 801 in FIG. 13). For example, as in the attachment pad indicated by reference numeral "902", a flexible attachment pad having a regular triangle shape in appearance may be formed by partially removing the pad body in a region in which the wiring structure (e.g., the second wiring electrode 831b or the third wiring electrode 831c in FIG. 12) is not disposed.

Figure 15:
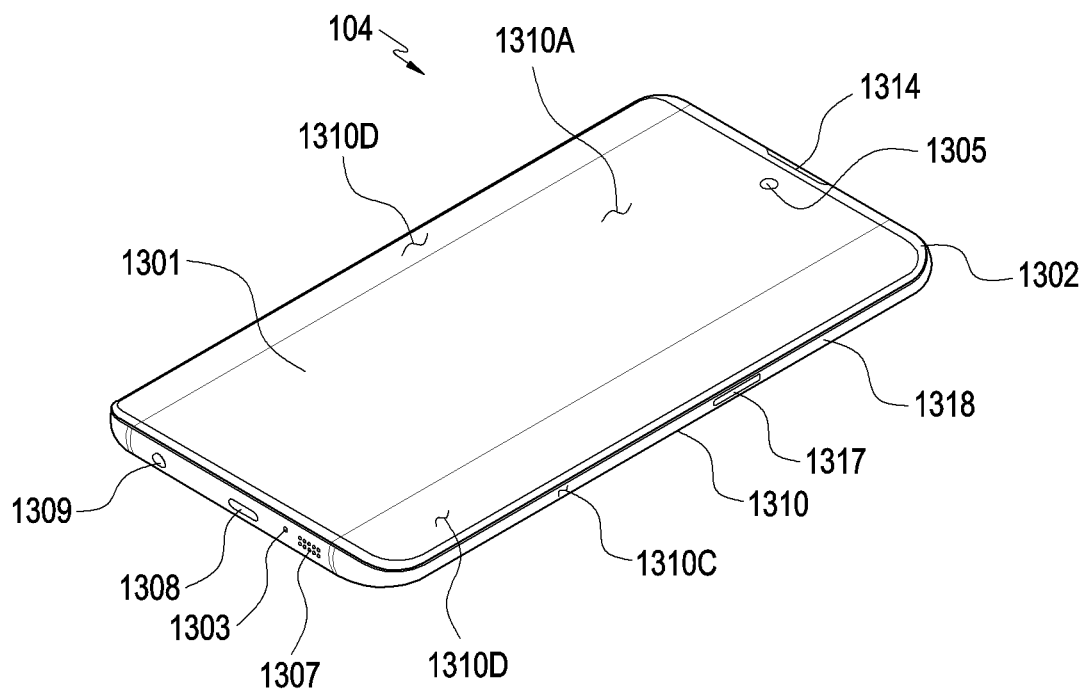
FIG. 15 is a perspective view of the front surface of an electronic device according to certain embodiments.
Figure 16:
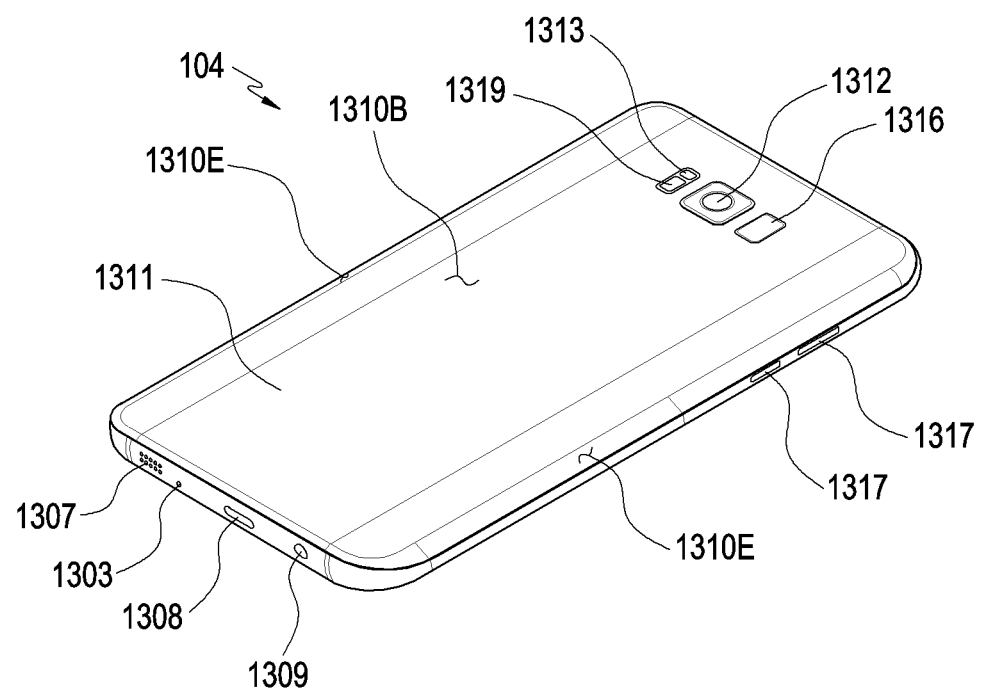
FIG. 16 is a perspective view of the rear surface of an electronic device according to certain embodiments.

As described above, according to certain embodiments, in the biological signal measurement device (e.g., the biological signal measurement device 300 in FIG. 3), it is possible to miniaturize a rigid module housing or measurement module (e.g., the measurement module 400 in FIG. 5) and to dispose measurement electrodes (the third wiring electrodes 831c in FIG. 12) on an attachment pad, which is flexible (or easily attachable to the user's body) (e.g., the attachment pad 800 in FIG. 12). For example, due to the flexibility of the attachment pad, it is easy to attach the attachment pad to a bent body part, and it is possible to secure a sufficient gap between the measurement electrodes. A module housing or a measurement module having a circuit device or the like therein may be electrically connected to the measurement electrodes via a wiring structure embedded in the attachment pad. According to an embodiment, the module housing or measurement module is capable of maintaining a stable coupling state with the attachment pad by magnetic force, and replacement of the attachment pad may be facilitated. This magnetic force is generated by an electrode (e.g., the electrode 503 in FIG. 6) provided in the module housing or measurement module and an electrode (e.g., the first to fourth terminals 731a to 731d in FIG. 9) provided in the attachment pad. According to another embodiment, the number of measurement electrodes may be four. For example, a biological signal measurement device (e.g., the biological signal measurement device 300 in FIG. 3) may include one reference electrode and at least three measurement electrodes, in which two arbitrarily selected electrodes among three measurement electrodes may be paired (or may form a lead) so as to detect a biological signal. When the number of measurement electrodes is three, three electrode pairs, each including two arbitrarily selected electrodes, may be formed. For example, one biological signal measurement device is capable of measuring a biological signal through three leads, and as the number of leads (e.g., electrode pairs) capable of measuring a biological signal is increased, accuracy in measurement can be improved FIG. 15 is a perspective view of the front surface of the electronic device 104 according to certain embodiments. FIG. 16 is a perspective view of the rear surface of the electronic device 104 according to certain embodiments.

Referring to FIGS. 15 and 16, the electronic device 104 according to an embodiment may include a housing 1310 including: a first surface (or a front surface) 1310A; a second surface (or a rear surface) 1310B; and a side surface (e.g. the side surface 1310C in FIG. 15 or 16) surrounding the space between the first surface 1310A and the second surface 1310B. In another embodiment (not shown), the housing 1310 may refer to a structure forming some of the first surface (e.g. the first surface 1310A in FIG. 15), the second surface (e.g. the second surface 1310B in FIG. 16), and the side surface 1310C in FIG. 15. According to an embodiment, the first surface 1310A may be formed of a front plate 1302 (e.g. a glass plate including various coating layers, or a polymer plate), at least a part of which is substantially transparent. The second surface 1310B may be formed of a substantially opaque rear plate 1311. The rear plate 1311 may be formed of, for example, coated or colored glass, ceramic, polymer, metal (e.g. aluminum, stainless steel (STS), or magnesium), or a combination of at least two of the above-described materials. The side surface 1310C is coupled to the front plate 1302 and the rear plate 1311, and may be formed of a side bezel structure (or "a side member") 1318 which contains metal and/or polymer. In an embodiment, the rear plate 1311 and the side bezel structure 1318 may be integrally formed and may contain the same material (e.g. a metal material such as aluminum).

In an illustrated embodiment, the front plate 1302 may include two first regions 1310D which are provided at both ends of the long edge of the front plate 1302 and are bent or seamlessly extend from the first surface 1310A to the rear plate 1311. In an illustrated embodiment (see FIG. 16), the rear plate 1311 may include two second regions 1310E which are provided at both ends of the long edge thereof and are bent or seamlessly extend from the second surface 1310B to the front plate 1302. In an embodiment, the front plate 1302 (or the rear plate 1311) may include one of the first regions 1310D (or the second regions 1310E) (e.g., to the exclusion of the other). In another embodiment, some of the first regions 1310D or second regions 1310E may not be included. The above-described embodiments, when the electronic device 104 is seen from the side thereof, the side bezel structure 1318 may have a first thickness (width) at a side surface which does not include the first regions 1310D or second regions 1310E, and may have a second thickness, which is smaller than the first thickness, at a side surface including the first regions 1310D or the second regions 1310E.

According to an embodiment, the electronic device 104 may include at least one among: a display 1301; audio modules 1303, 1307, and 1314; sensor modules 1316 and 1319; camera modules 1305, 1312, and 1313; a key input device 1317; and connector holes 1308 and 1309. In an embodiment, in the electronic device 104, at least one (e.g. the key input device 1317) of the elements may be omitted or another element may be additionally included.

The display 1301 may be exposed through, for example, a considerable portion of the front plate 1302. In an embodiment, the display 1301 may be at least partially exposed through the front plate 1302 which the first surface 1310A and a first region 1310D of the side surface 1310C. In an embodiment, the edge of the display 1301 may be formed to have a shape identical to the shape of an outer edge of the front plate 1302 adjacent thereto. In another embodiment (not shown), in order to increase an exposed area of the display 1301, the gaps between the outer edges of the display 1301 and the outer edges of the front plate 1302 may be formed to be approximately equal to each other.

In another embodiment, a recess or an opening is formed in a part of the screen display region of the display 1301, and the electronic device may include at least one of the camera module 1305 and a sensor module (not shown) aligned with the recess or the opening. In another embodiment (not shown), at least one of the audio module 1314, the sensor module (not shown), the camera module 1305, the fingerprint sensor 1316, and the light-emitting diode (not shown) may be included on the rear surface of the screen display region of the display 1301. In another embodiment (not shown), the display 1301 may be coupled to or disposed adjacent to a touch sensing circuit, a pressure sensor capable of measuring the strength (pressure) of touch, and/or a digitizer for detecting a stylus pens using a magnetic field. In an embodiment, at least a part of the sensor modules 1319 and/or at least a part of the key input device 1317 may be disposed in the first regions 1310D, and/or the second regions 1310E.

The audio modules 1303, 1307, and 1314 may include a microphone hole and speaker holes. A microphone for acquiring external sound may be disposed in the microphone hole, and, in an embodiment, multiple microphones may be disposed so as to sense the direction of sound. The speaker holes may include an outer speaker hole and a calling receiver hole. In an embodiment, the speaker holes and the microphone hole may be implemented as one hole, or a speaker (e.g. a Piezo speaker) may be included without the speaker holes.

The sensor modules 1316 and 1319 may generate an electrical signal or a data value, which corresponds to an operation state inside the electronic device 104 or an environment state outside the electronic device 104. The sensor modules 1316 and 1319 may include, for example, a first sensor module (e.g. a proximity sensor) and/or a second sensor module (not shown) (e.g. a fingerprint sensor), disposed on the first surface 1310A of the housing 1310, and/or a third sensor module 1319 (e.g. an HRM sensor) and/or a fourth sensor module 1316 (e.g., a fingerprint sensor), disposed on the second surface 1310B of the housing 1310. The fingerprint sensor may be disposed not only on the first surface 1310A (e.g. the display 1301) of the housing 1310 but also on the second surface 1310B thereof. The electronic device 104 may further include at least one of an unillustrated sensor module, for example, a gesture sensor, a gyro sensor, an air pressure sensor, a magnetic sensor, an acceleration sensor, a grip sensor, a color sensor, an infrared (IR) sensor, a biometric sensor, a temperature sensor, a humidity sensor, or an illuminance sensor.

The camera modules 1305, 1312, and 1313 may include: a first camera module 1305 disposed on the first surface 1310A of the electronic device 104; and a second camera module 1312 and/or a flash 1313, disposed on the second surface 1310B. Each of the camera modules 1305 and 1312 may include one or multiple lenses, an image sensor, and/or an image signal processor. The flash 1313 may include, for example, a light-emitting diode or a xenon lamp. In an embodiment, two or more lenses (an infrared camera, wide-angle and telephoto lenses) and image sensors may be disposed on one surface of the electronic device 104.

The connector holes 1308 and 1309 may include: a first connector hole 1308 capable of receiving a connector (e.g. a USB connector) for transmitting or receiving power and/or data to or from an external electronic device; and/or a second connector hole (e.g. an earphone jack) 1309 capable of receiving a connector for transmitting or receiving an audio signal to or from an external electronic device.

Figure 17:
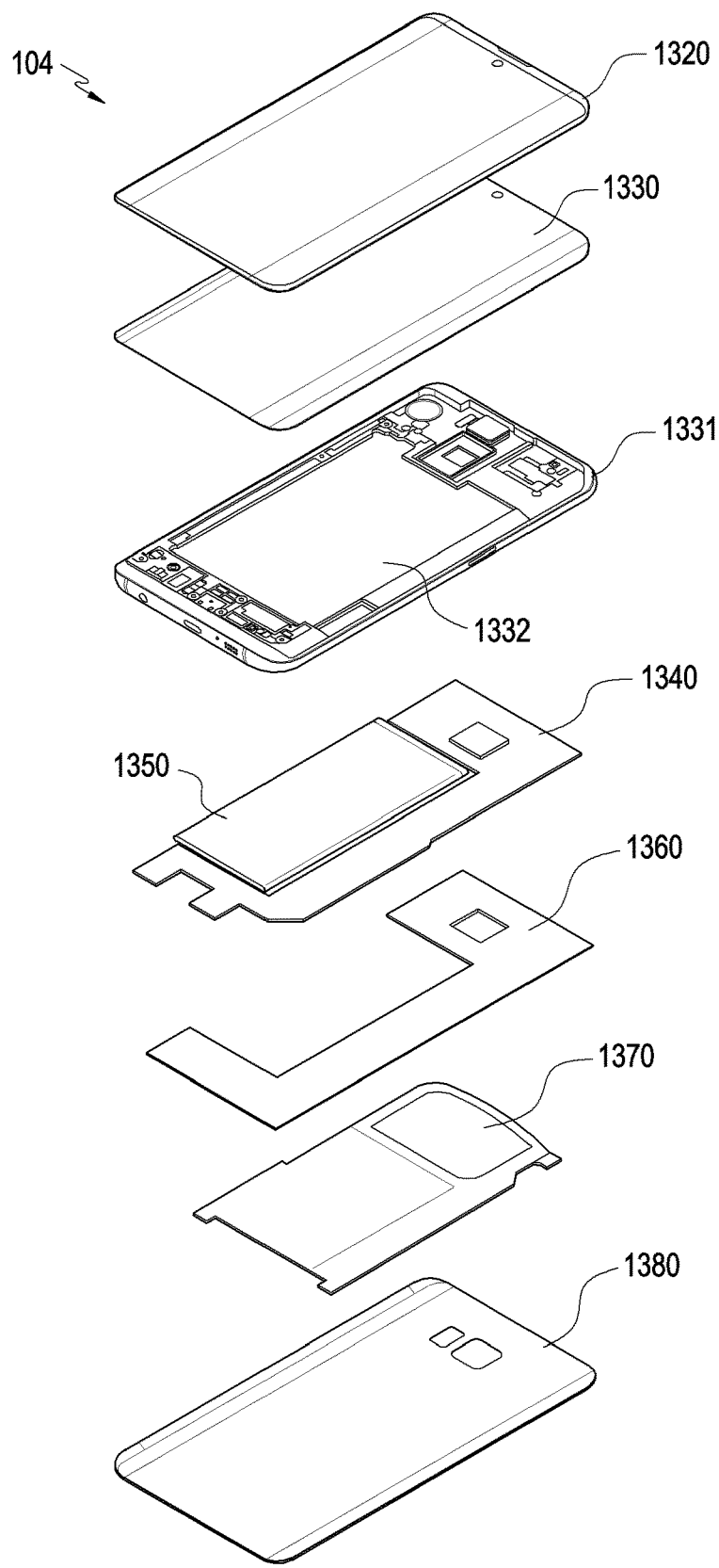
FIG. 17 is an exploded perspective view of an electronic device according to certain embodiments.

FIG. 17 is an exploded perspective view of an electronic device 104 according to certain embodiments.

Referring to FIG. 17, the electronic device 104 (e.g., the electronic device 104 in FIG. 15 or 16) may include: a side bezel structure 1331; a first support member 1332 (e.g., a bracket); a front plate 1320; a display 1330; a printed circuit board 1340; a battery 1350; a second support member 1360 (e.g., rear case); an antenna 1370; and rear plate 1380. In an embodiment, in the electronic device 104, at least one (e.g., the first support member 1332 or the second support member 1360) of the elements may be omitted, or another element may be additionally included. At least one of the elements of the electronic device 104 may be the same as or similar to at least one of the elements of the electronic device 104 in FIG. 15 or 16. Thus, hereinafter, a redundant description will be omitted.

The first support member 1332 may be disposed inside the electronic device 104 and connected to the side bezel structure 1331, or may be formed integrally with the side bezel structure 1331. The first support member 1332 may be formed of, for example, a metal material and/or non-metal (e.g. polymer) material. The first support member 1332 may have one surface to which the display 1330 is coupled, and another surface to which the printed circuit board 1340 is coupled. A processor, a memory, and/or an interface may be mounted on printed circuit board 1340. The processor may include at least one of, for example, a central processing unit, an application processor, a graphics-processing unit, an image signal processor, a sensor hub processor, or a communication processor.

The memory may include, for example, volatile memory or nonvolatile memory.

The interface may include, for example, a high definition multimedia interface (HDMI), a universal serial bus (USB) interface, an SD card interface, and/or an audio interface.

The interface may electrically or physically connect the electronic device 104 to an external electronic device, and may include a USB connector, an SD card/MMC connector, or an audio connector.

The battery 1350 is a device for supplying power to at least one element of the electronic device 104, and may include, for example, an non-rechargeable primary battery a rechargeable secondary battery, or a fuel cell. At least a part of the battery 1350 may be disposed, for example, on substantially the same plane together with the printed circuit board 1340. The battery 1350 may be integrally disposed inside the electronic device 104 and may be detachably disposed in the electronic device 104.

The antenna 1370 may be disposed between the rear plate 1380 and the battery 1350. The antenna 1370 may include, for example, a near field communication (NFC) antenna, a wireless charging antenna, and/or a magnetic secure transmission (MST) antenna. For example, the antenna 1370 may perform short-range communication with an external device, or may transmit or receiving power utilized for charging to or from the external device in a wireless manner. In another embodiment, an antenna structure may be formed by a part of the side bezel structure 1331 and/or the first support member 1332 or a combination thereof.

According to certain embodiments, the electronic device may include multiple communication devices (not shown). For example, some of the multiple communication devices (not shown) may be implemented to transmit or receive radio waves having different characteristics (tentatively referred to as electric waves of A and B frequency bands) in order to implement MIMO. As another example, some of the multiple communication devices (not shown) may be configured to simultaneously transmit or receive radio waves having the same characteristics (tentatively referred to as radio waves of A1 and A2 frequencies in the A frequency band) in order to implement diversity. As another example, others of the multiple communication devices (not shown) may be configured to simultaneously transmit or receive radio waves having the same characteristics (tentatively referred to as radio waves of B1 and B2 frequencies in the B frequency band) in order to implement diversity. In an embodiment, two communication devices may be included, but, in another embodiment, the electronic device 104 may include four communication devices to simultaneously implement MIMO and diversity. In another embodiment, the electronic device 104 may include one communication device (not shown) (e.g., to the exclusion of another).

According to an embodiment, when one communication device is disposed at a first position of the printed circuit board 1340 in consideration of transmission and reception characteristics of radio waves, another communication device may be disposed at a second position separated from the first position of the printed circuit board 1340. As another example, one communication device and another communication device may be disposed in consideration of the separation distance between each other according to diversity characteristics.

According to an embodiment, at least one communication device (not shown) may include a wireless communication circuit that processes radio waves transmitted and received in an ultra-high frequency band (e.g., 6 GHz to 300 GHz). Radiating conductor(s) of the at least one communication device (not shown) may include, for example, a patch-type radiating conductor or a dipole-shaped radiating conductor extending in one direction. The multiple radiating conductors may be arrayed to form an antenna array. A chip (e.g., an integrated circuit chip) on which a part of the wireless communication circuit is implemented may be disposed on one side of a region where the radiation conductor is disposed or on a surface facing a direction opposite to that of the surface on which the radiation conductor is disposed. For example, the chip may be electrically connected to the radiation conductor (s) through a wiring formed as a printed circuit pattern.

Figure 18:
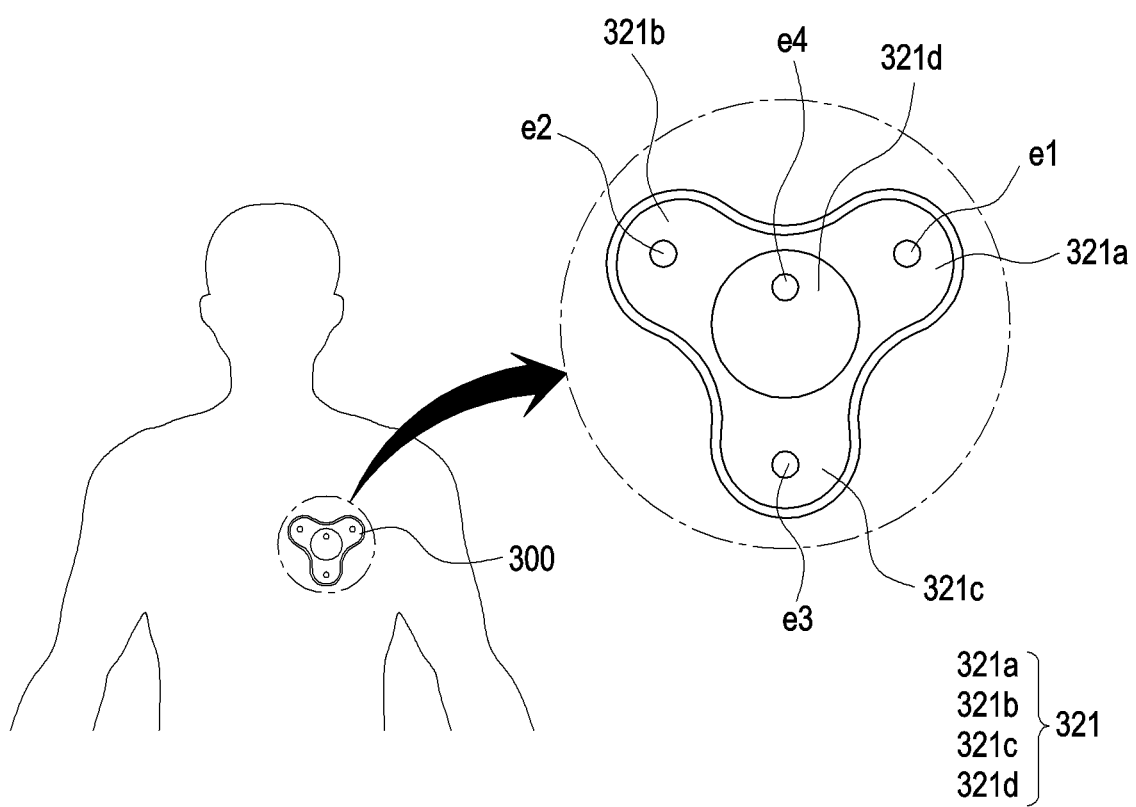
FIG. 18 illustrates a biological signal measurement device attached to a user according to certain embodiments.
Figure 19A:
FIG. 19A illustrates a biological signal generated based on a signal sensed using an electronic device according to certain embodiments.
Figure 19A:
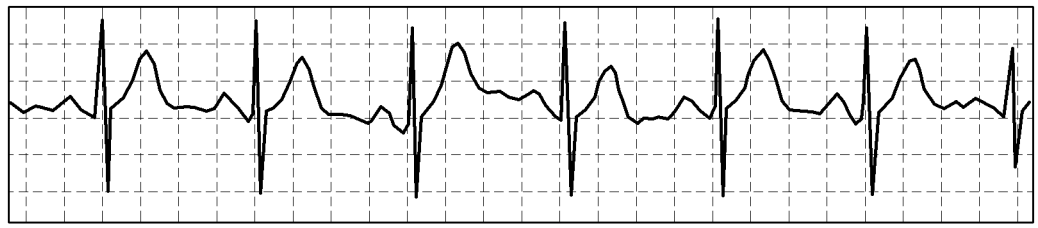
Figure 19B:
FIG. 19B illustrates a biological signal generated based on a signal sensed using an electronic device according to certain embodiments.
Figure 19B:
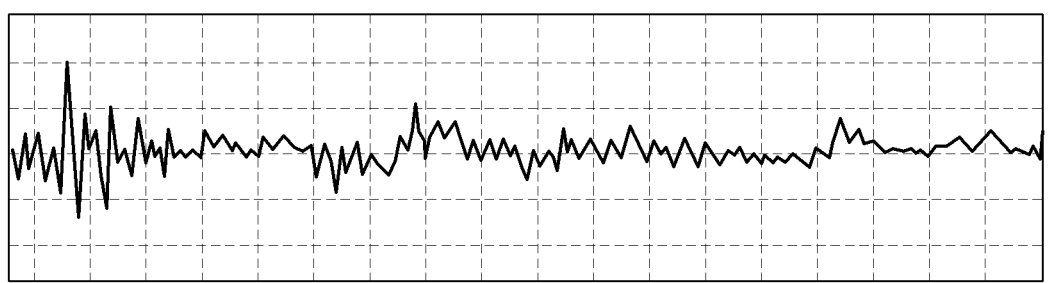
Figure 20:
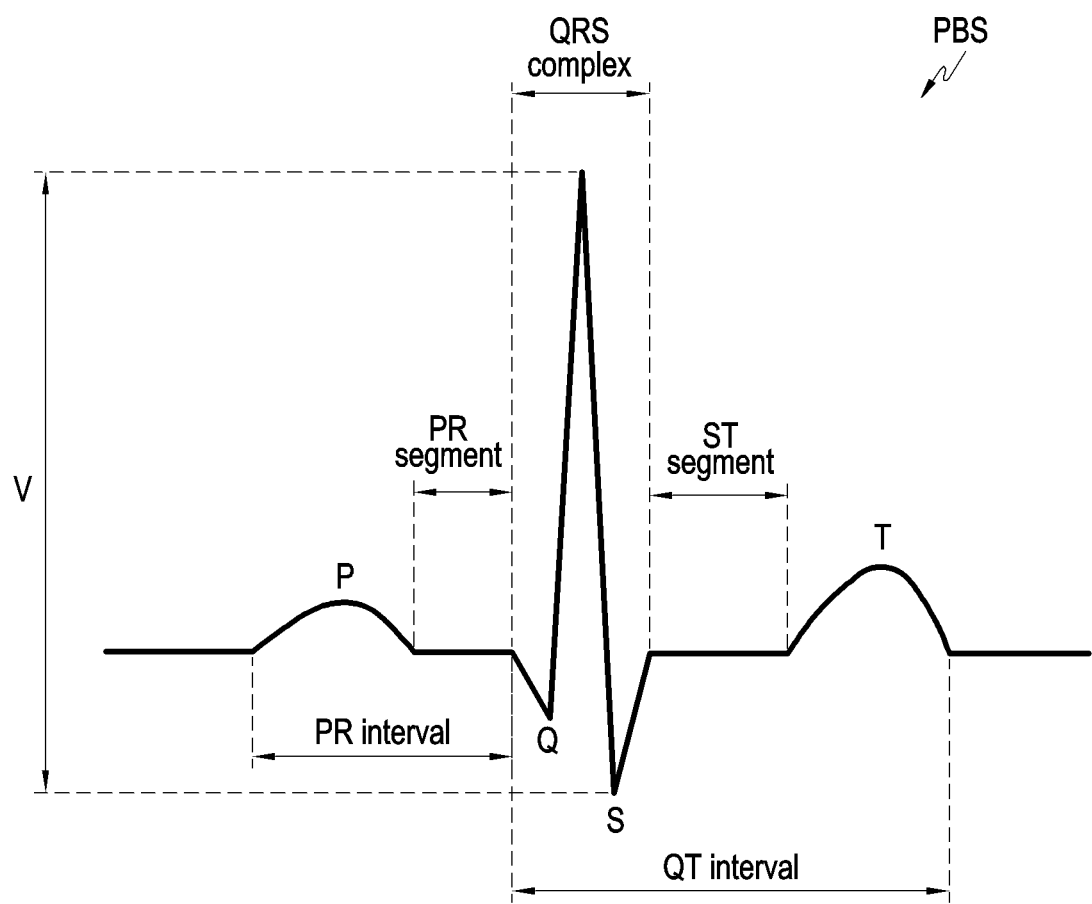
FIG. 20 is a view for describing a preconfigured biological signal according to certain embodiments.

FIG. 18 illustrates a biological signal measurement device attached to a user according to certain embodiments. FIG. 19A illustrates a biological signal generated based on a signal sensed using an electronic device according to certain embodiments, and FIG. 19B illustrates a biological signal generated based on a signal sensed using an electronic device according to certain embodiments. FIG. 20 is a view for describing a preconfigured biological signal according to certain embodiments.

According to FIGS. 18, 19A, 19B, and 20, the biological signal measurement device 300 may include a (3-1)th wiring electrode e1, a (3-2)th wiring electrode e2, a (3-3)th wiring electrode e3, and a (3-4)th wiring electrode e4. The configuration of the (3-1)th wiring electrode e1, the (3-2)th wiring electrode e2, the (3-3)th wiring electrode e3, and the (3-4)th wiring electrode e4 may be partially or totally identical to the configuration of the third wiring electrodes 831C in FIG. 12. The (3-1)th wiring electrode e1 may be electrically connected to the first electrode 631a in FIG. 8, the (3-2)th wiring electrode e2 may be electrically connected to the second electrode 631b in FIG. 8, the (3-3)th wiring electrode e3 may be electrically connected to the third electrode 631c in, and the (3-4)th wiring electrode e4 may be electrically connected to the fourth electrode 631d.

According to FIG. 18, the biological signal measurement device 300 may include a first pad body 321a, a second pad body 321b, and a third pad body 321c. The first pad body 321a, the second pad body 321b, and the third pad body 321c in FIG. 18 are parts of the pad body 321 in FIG. 3, and may be at least partially identical or similar to the pad body 801 of FIG. 12.

According to certain embodiments, the biological signal measurement device 300 attached to the body of a user may sense a first signal, a second signal, and a third signal. According to an embodiment, a processor (e.g., the processor 120 in FIG. 1) may sense an electrical signal generated from the electrical activity of the user's heart by using the (3-1)th wiring electrode e1, the (3-2)th wiring electrode e2, the (3-3)th wiring electrode e3, and the (3-4)th wiring electrode e4. For example, the processor 120 may sense the first signal by using the (3-1)th wiring electrode e1 and the (3-4)th wiring electrode e4 (e.g., a reference electrode), may sense the second signal by using the (3-2)th wiring electrode e2 and the (3-4)th wiring electrode e4, and may sense the third signal by using the (3-3)th wiring electrode e3 and the (3-4)th wiring electrode e4.

According to certain embodiments, the processor 120 may measure impedance for at least one of a first electrical path, a second electrical path, a third electrical path, or a fourth electrical path. The first electrical path may be formed by the first electrode 631a, the first terminal 731a, the first wiring electrode 831a, the second wiring electrode 831b, and the third wiring electrode 831c. The second electrical path may be formed by the second electrode 631b, the second terminal 731b, the first wiring electrode 831a, the second wiring electrode 831b, and the third wiring electrode 831c. The third electrical path may be formed by the third electrode 631c, the third terminal 731c, the first wiring electrode 831a, the second wiring electrode 831b, and the third wiring electrode 831c. The fourth electrical path may be formed by the fourth electrode 631d, the fourth terminal 731d, the first wiring electrode 831a, the second wiring electrode 831b, and the third wiring electrode 831c. According to an embodiment, the processor 120 may measure impedance for at least one of the (3-1)th wiring electrode e1, the (3-2)th wiring electrode e2, the (3-3)th wiring electrode e3, or the (3-4)th wiring electrode e4. According to another embodiment, the processor 120 may measure impedance for at least one of the first electrode 631a, the second electrode 631b, the third electrode 631c, and the fourth electrode 631d. The processor 120 may determine, based on the measured impedance, whether the biological signal measurement device 300 has been attached to the user's body.

According to certain embodiments, an attachment pad 321 may include a first attachment pad region 321a, a second attachment pad region 321b, a third attachment pad region 321c, and a fourth attachment pad region 321d. The first attachment pad region 321a, the second attachment pad region 321b, and the third attachment pad region 321c may be formed in shapes which extend in different directions from the fourth attachment pad region 321d of the attachment pad 321, respectively.

According to certain embodiments, the (3-1)th wiring electrode e1, the (3-2)th wiring electrode e2, the (3-3)th wiring electrode e3, and the (3-4)th wiring electrode e4 may be disposed in consideration of the separation distance between each other. For example, the (3-1)th wiring electrode e1 may be disposed in the first attachment pad region 321a, the (3-2)th wiring electrode e2 may be disposed in the second attachment pad region 321b, the (3-3)th wiring electrode e3 may be disposed in the third attachment pad region 321c, and the (3-4)th wiring electrode e4 may be disposed in the fourth attachment pad region 321d.

According to certain embodiments, at least one of the first attachment pad region 321a, the second attachment pad region 321b, or the third attachment pad region 321c may be formed in various structures in order to induce a user to attach the biological signal measurement device 300 at an accurate position. According to an embodiment, each of the first attachment pad region 321a, the second attachment pad region 321b, and the third attachment pad region 321c may include a light source (e.g., a light-emitting diode (LED)). A first light source disposed in the first attachment pad region 321a, a second light source disposed in the second attachment pad region 321b, and a third light source disposed in the third attachment pad region 321c may provide a user with different colors of light, different shapes of light, or different blinking periods of light in order to provide the user with a position at which the biological signal measurement device 300 is to be disposed. According to another embodiment, the first attachment pad region 321a, the second attachment pad region 321b, and the third attachment pad region 321c may be formed in different colors so as to provide the user with the position at which the biological signal measurement device 300 is to be disposed. According to another embodiment, at least one of the first attachment pad region 321a, the second attachment pad region 321b, or the third attachment pad region 321c may include letters for providing the user with the position at which the biological signal measurement device 300 is to be disposed. For example, letters (e.g., LA) indicating a left arm may be positioned in the first attachment pad region 321a, and letters (e.g., RA) indicating a right arm may be positioned in the second attachment pad region 321b.

According to certain embodiments, biological signals may be acquired using the biological signal measurement device 300. According to an embodiment, the biological signal measurement device 300 may generate a first biological signal, a second biological signal, and a third biological signal, based on the first signal, the second signal, and the third signal, which have been sensed. According to another embodiment, another electronic device (e.g., the electronic device 102 or 104 in FIG. 1), connected to the biological signal measurement device 300 via a direct (e.g., wired) communication channel or a wireless communication channel, may receive the first signal, the second signal, and the third signal, which have been sensed by the biological signal measurement device 300, from the biological signal measurement device 300, and may generate the first biological signal, the second biological signal, and the third biological signal, based on the first signal, the second signal, and the third signal which have been received. Multiple biological signals are acquired using one biological signal measurement device 300, and thus the accuracy of the biological signals may be increased. Further, according to another embodiment, the electronic device 104 may receive a biological signal from the biological signal measurement device 300.

According to certain embodiments, biological signals including the first biological signal, the second biological signal, and the third biological signal may be generated based on the first signal, the second signal, and the third signal. For example, the first biological signal may be generated based on the first signal and the second signal, the second biological signal may be generated based on the second signal and the third signal, and the third biological signal may be generated based on the third signal and the first signal.

According to certain embodiments, the (3-4)th wiring electrode e4 may be provided as a reference electrode for the (3-1)th wiring electrode e1, the (3-2)th wiring electrode e2, or the (3-3)th wiring electrode e3, and the first biological signal may be substantially determined by the comparison between or a combination of signals sensed using the (3-1)th wiring electrode e1 and the (3-2)th wiring electrode e2, based on the electric potential of the (3-4)th wiring electrode e4. According to an embodiment, the first biological signal may be determined based on a signal (signals) sensed using a lead or an electrode pair including the (3-1)th wiring electrode e1 and the (3-2)th wiring electrode e2. According to another embodiment, the second biological signal may be determined based on a signal (signals) sensed using a lead or an electrode pair including the (3-2)th wiring electrode e2 and the (3-3)th wiring electrode e3. Further, according to another embodiment, the third biological signal may be determined based on a signal (signals) sensed using a lead or an electrode including the (3-3)th wiring electrode e3 and the (3-1)th wiring electrode e1.

According to certain embodiments, a biological signal may include information on a user's condition. For example, a biological signal may include at least one of a heart rate, a heart rhythm, an electrocardiogram (ECG), a photoplethysmography (PPG), a blood pressure, a blood-oxygen saturation level, a respiratory rate, a blood sugar level, or a body temperature. According to an embodiment, the biological signal may be defined as a signal including information related to an electrocardiogram. For example, the biological signal may include information on at least one of QRS waves (QRS-complex), PR segment, ST segment, P-R interval, QT interval, and voltage amplitude.

According to certain embodiments, whether the biological signal measurement device 300 is normally attached to a user's body may be determined based on a biological signal. For example, a biological signal may be compared with a preconfigured biological signal (PBS), and whether the biological signal measurement device 300 has been normally attached to the user's body may be determined. According to an embodiment, when the first biological signal is determined to be a noise biological signal, which is not a normal biological signal, through the comparison between the first biological signal and the preconfigured biological signal (PBS), it may be determined that at least one of the (3-1)th wiring electrode e1, the (3-2)th wiring electrode e2, or the (3-4)th wiring electrode e4, used to generate the first biological signal, is not normally attached to the body. According to another embodiment, when the second biological signal is determined to be a noise biological signal, which is not a normal biological signal, through the comparison between the second biological signal and the preconfigured biological signal (PBS), it may be determined that at least one of the (3-2)th wiring electrode e2, the third electrode e2, or the (3-4)th wiring electrode e4, used to generate the second biological signal, is not normally attached to the body. Further, according to another embodiment, when the third biological signal is determined to be a noise biological signal, which is not a normal biological signal, through the comparison between the third biological signal and the preconfigured biological signal (PBS), it may be determined that at least one of the (3-3)th wiring electrode e3, the (3-1)th wiring electrode e1, or the (3-4)th wiring electrode e4, used to generate the third biological signal, is not normally attached to the body. The normal biological signal may be defined as a biological signal generated when an electrode is normally attached to the body (e.g., FIG. 19A). For example, the normal biological signal may be defined as a biological signal having a range in which an acquired biological signal corresponds to the preconfigured biological signal (PBS). The noise biological signal may be a biological signal generated when an electrode is not normally attached to the body (e.g., FIG. 19B). For example, the noise biological signal may be a biological signal having a range in which an acquired biological signal does not correspond to the preconfigured biological signal (PBS).

According to an embodiment, the processor (e.g., the processor 120 in FIG. 1) of the biological signal measurement device 300 may determine whether the biological signal measurement device 300 has been normally attached to a user's body. According to another embodiment, another electronic device (e.g., the electronic device 102 or 104 in FIG. 1), connected to the biological signal measurement device 300 via a direct (e.g., wired) communication channel or a wireless communication channel, may determine whether the biological signal measurement device 300 is attached to the user's body, based on the first signal, the second signal, and the third signal which have been received from the biological signal measurement device 300.

According to certain embodiments, whether the biological signal measurement device 300 is normally attached to the user's body may be determined using various methods. According to an embodiment, whether at least one of the (3-1)th wiring electrode e1, the (3-2)th wiring electrode e2, or the (3-4)th wiring electrode e4, used to generate the first biological signal, is normally attached to the user's body may be determined by comparing at least one of the QRS waves (QRS-complex), PR segment, ST segment, P-R interval, QT interval, and voltage (V) of the first biological signal with at least one of the QRS waves (QRS-complex), PR segment, ST segment, P-R interval, QT interval, and voltage (V) of the preconfigured biological signal (PBS). According to another embodiment, whether at least one of the (3-2)th wiring electrode e2, the (3-3)th wiring electrode e3, or the (3-4)th wiring electrode e4, used to generate the second biological signal, is normally attached to the user's body may be determined by comparing at least one of the QRS waves (QRS-complex), PR segment, ST segment, P-R interval, QT interval, and voltage (V) of the second biological signal with at least one of the QRS waves (QRS-complex), PR segment, ST segment, P-R interval, QT interval, and voltage (V) of the preconfigured biological signal (PBS). Further, according to another embodiment, whether at least one of the (3-3)th wiring electrode e3, the (3-1)th wiring electrode e1, or the (3-4)th wiring electrode e4, used to generate the second biological signal, is normally attached to the user's body may be determined by comparing at least one of the QRS waves (QRS-complex), PR segment, ST segment, P-R interval, QT interval, and voltage (V) of the third biological signal with at least one of the QRS waves (QRS-complex), PR segment, ST segment, P-R interval, QT interval, and voltage (V) of the preconfigured biological signal (PBS).

Figure 21A:
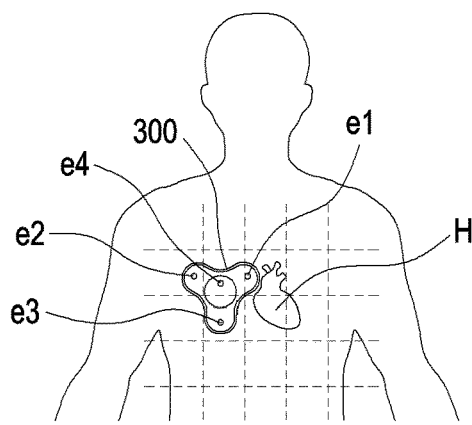
FIG. 21A illustrates a biological signal changed based on the position of an electronic device according to certain embodiments.
Figure 21A:
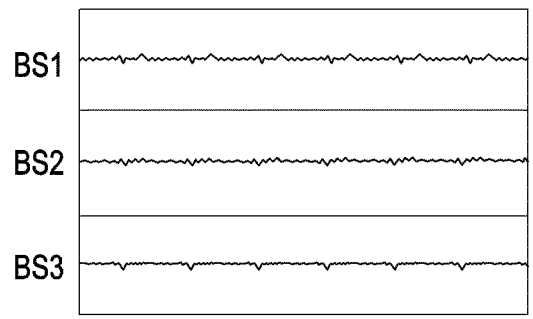
Figure 21B:
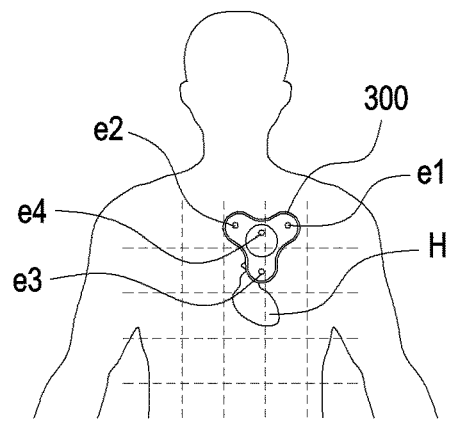
FIG. 21B illustrates a biological signal changed based on the position of an electronic device according to certain embodiments.
Figure 21B:
Figure 21C:
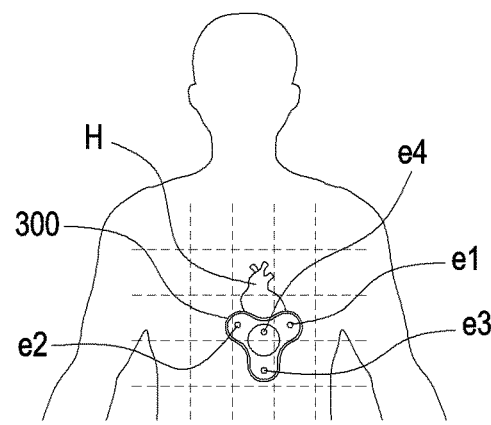
FIG. 21C illustrates a biological signal changed based on the position of an electronic device according to certain embodiments.
Figure 21C:
Figure 21D:
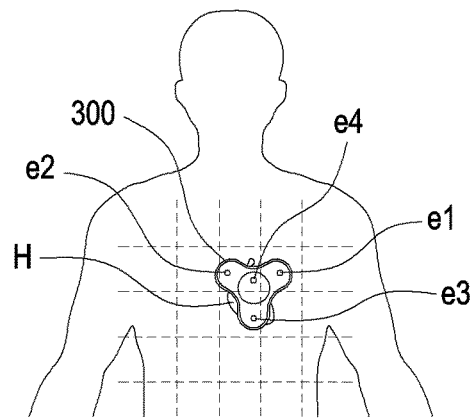
FIG. 21D illustrates a biological signal changed based on the position of an electronic device according to certain embodiments.
Figure 21D:
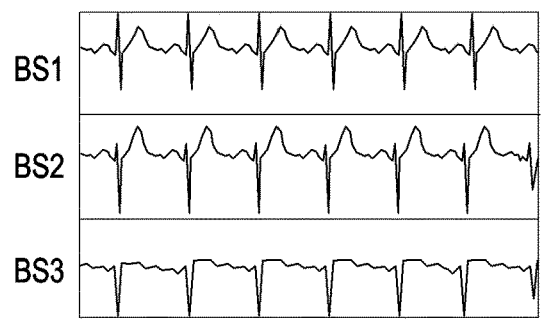

FIG. 21A illustrates a biological signal changed based on the position of an electronic device according to certain embodiments. FIG. 21B illustrates a biological signal changed based on the position of an electronic device according to certain embodiments. FIG. 21C illustrates a biological signal changed based on the position of an electronic device according to certain embodiments. FIG. 21D illustrates a biological signal changed based on the position of an electronic device according to certain embodiments.

According to FIGS. 21A, 21B, 21C, and 21D, guide information for guiding the position of the biological signal measurement device 300 may be generated based on the first biological signal, the second biological signal, and the third biological signal. The guide information is defined as information including the position to which the biological signal measurement device 300 is to be moved in order to acquire a normal biological signal by using the biological signal measurement device 300. For example, the guide information may be information for moving the biological signal measurement device 300 to a position adjacent to the user's heart.

According to certain embodiments, the guide information may be generated based on the first biological signal, a second biological signal, and the third biological signal. For example, the guide information may be generated based on whether at least one of the first biological signal, the second biological signal, or the third biological signal is within the range of the preconfigured biological signal (PBS).

According to an embodiment, the processor (e.g., the processor 120 in FIG. 1) of the biological signal measurement device 300 may generate the guide information based on the first biological signal, the second biological signal, and the third biological signal. According to another embodiment, another electronic device (e.g., the electronic device 102 or 104 in FIG. 1), connected to the biological signal measurement device 300 via a direct (e.g., wired) communication channel or a wireless communication channel, may generate the guide information based on the first biological signal, the second biological signal, and the third biological signal.

According to certain embodiments, the guide information may be generated by a combination of the first biological signal, the second biological signal, and the third biological signal.

According to FIG. 21A, when the first biological signal, the second biological signal, and the third biological signal are all noise biological signals, the biological signal measurement device 300 or the electronic device 104 may generate guide information including information for attaching the biological signal measurement device 300 to another position.

According to FIG. 21B, when two biological signals among the first biological signal, the second biological signal, and the third biological signal are normal biological signals and one biological signal is a noise biological signal, guide information for changing the noise biological signal to a normal biological signal may be generated by changing the position of the biological signal measurement device 300. For example, when the second biological signal and the third biological signal are normal biological signals and the first biological signal is a noise biological signal, the biological signal measurement device 300 or the electronic device 104 may determine that the (3-3)th wiring electrode e3 used to generate the second biological signal and the third biological signal has been disposed at a position where a normal biological signal can be acquired, and that the (3-1)th wiring electrode e1 and the (3-2)th wiring electrode e2, used to generate the first biological signal, have been disposed at positions where a normal biological signal cannot be acquired. The guide information may be generated to include a displacement amount for moving the (3-1)th wiring electrode e1 and the (3-2)th wiring electrode e2 in a direction in which the (3-3)th wiring electrode e3 is disposed.

According to FIG. 21C, when one biological signal among the first biological signal, the second biological signal, and the third biological signal is a normal biological signal and two biological signals thereof are noise biological signals, guide information for changing the noise biological signals to normal biological signals may be generated by changing the position of the biological signal measurement device 300. For example, when the first biological signal is a normal biological signal and the second biological signal and the third biological signal are noise biological signals, the biological signal measurement device 300 or the electronic device 104 may determine that each of the (3-1)th wiring electrode e1 and the (3-2)th wiring electrode e2, which are used to generate the first biological signal, have been disposed at a position where a normal biological signal can be acquired, and that the (3-3)th wiring electrode e3 used to generate the second biological signal and the third biological signal has been disposed at a position where a normal biological signal cannot be acquired. The guide information may be generated to include a displacement amount for moving the (3-3)th wiring electrode e3 toward the (3-4)th wiring electrode e4.

According to FIG. 21D, when the first biological signal, the second biological signal, and the third biological signal are all normal biological signals, the biological signal measurement device 300 or the electronic device 104 may generate guide information indicating the completion of attachment of the biological signal measurement device 300.

According to certain embodiments, the guide information may be generated, transmitted, or received in the form of data related the guide information.

Figure 22:
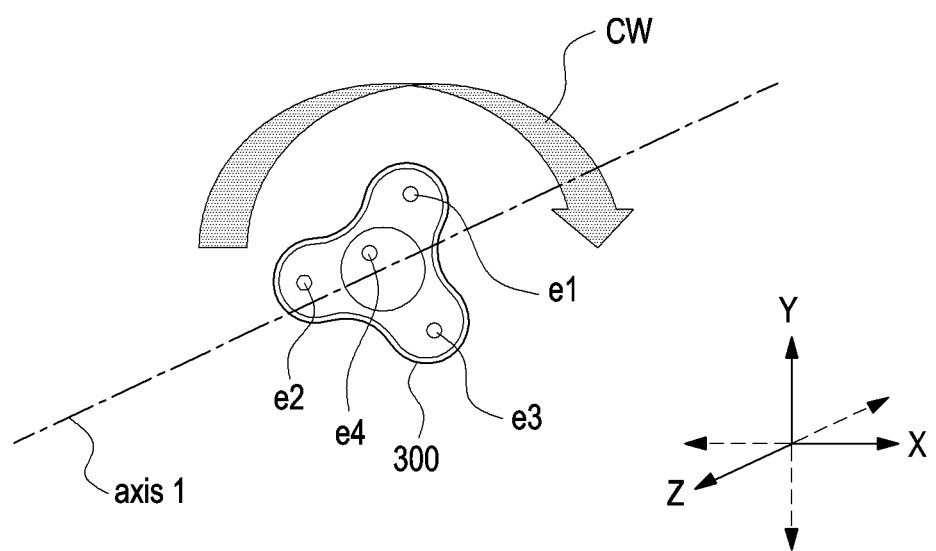
FIG. 22 is a view for describing angle information generated using an acceleration sensor according to certain embodiments.

FIG. 22 is a view for describing angle information generated using an acceleration sensor according to certain embodiments.

According to FIG. 22, the processor (e.g., the processor 120 in FIG. 1) of the biological signal measurement device 300 may generate angle information of the biological signal measurement device 300 by using an acceleration sensor (not shown). For example, the processor 120 may determine a position on a first plane (e.g., XY plane) where the (3-1)th wiring electrode e1, the (3-2)th wiring electrode e2, the (3-3)th wiring electrode e3, or the (3-4)th wiring electrode e4 is disposed, with reference to a first axis (axis 1) which is a virtual axis facing in the direction (+Z direction) perpendicular to the bottom surface of the biological signal measurement device 300. According to an embodiment, the processor 120 may generate, based on an angle of the biological signal measurement device 300 sensed by the acceleration sensor, angle information reflecting an angle at which the biological signal measurement device 300 has been rotated in the clockwise (CW) or counterclockwise direction from a position for acquiring a normal biological signal.

According to certain embodiments, the acceleration sensor may sense angle information reflecting an angle at which the biological signal measurement device 300 has been disposed. The configuration of the acceleration sensor (not shown) may be partially or totally identical to that of the accelerometer 239b in FIG. 2. According to an embodiment, the acceleration sensor may be an acceleration sensor (e.g., a three-axis acceleration sensor) capable of sensing tilting in three directions. When the acceleration sensor is a three-axis acceleration sensor, the size of a power source utilized for measuring angle information may be reduced. According to another embodiment, the acceleration sensor may further include a three-axis gyro sensor.

According to certain embodiments, the processor (e.g., the processor 120 in FIG. 1) of the biological signal measurement device 300 or another electronic device (e.g., the electronic device 102 or 104 in FIG. 1), connected to the biological signal measurement device 300 via a direct (e.g., wired) communication channel or a wireless communication channel, may generate guide information in additional consideration of angle information. For example, the processor 120 or the electronic device 104 may generate, based on angle information, guide information including an angle by which the biological signal measurement device 300 is to be rotated in order to acquire a normal biological signal.

Figure 23:
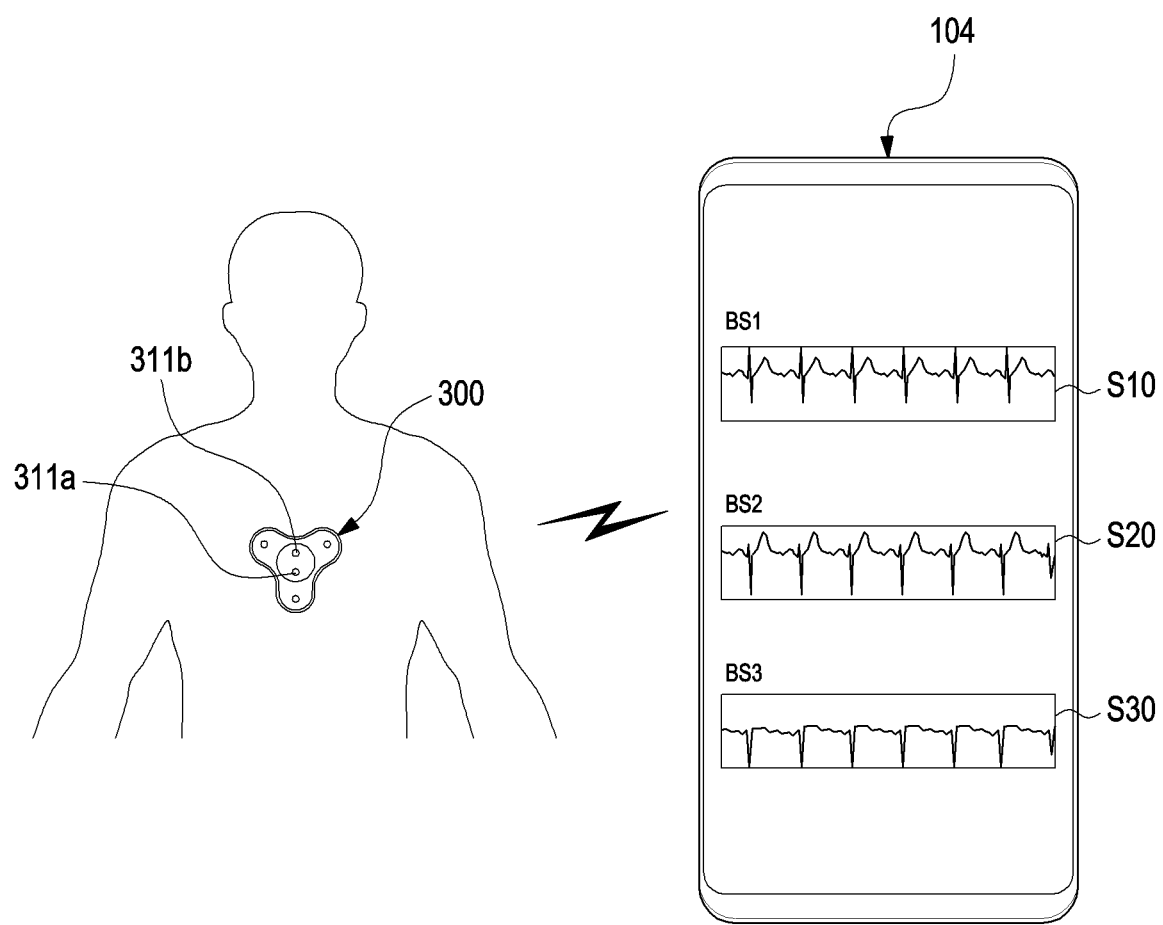
FIG. 23 illustrates a biological signal measurement device for outputting guide information, based on a biological signal according to certain embodiments.

FIG. 23 illustrates a biological signal measurement device for outputting guide information, based on a biological signal according to certain embodiments.

According to FIG. 23, the biological signal measurement device 300 may output guide information. For example, the output unit 311b may output light, an image, or sound, which has been configured to reflect guide information, to the outside. The output unit 311b may be configured to output at least one of the angle, direction, or distance by which the biological signal measurement device 300 is to be moved in order to measure a normal biological signal.

According to certain embodiments, the output unit 311b may provide guide information to a user through various methods. According to an embodiment, the output unit 311b may include a display (e.g., the display device 160 in FIG. 1), and the display may provide, based on the guide information, the user with at least one of the angle, direction, or distance by which the biological signal measurement device 300 is to be moved. According to another embodiment, the output unit 311b may include a light source (e.g., the LED 237b in FIG. 2), and, by using the color, shape, or blinking period of light output based on the guide information, the light source may provide the user with the at least one of the angle, direction, or distance by which the biological signal measurement device 300 is to be moved. According another embodiment, the output unit 311b may include a speaker (e.g., the sound output unit 155 in FIG. 1), and the speaker may provide, through sound output based on the guide information, the user with the at least one of the angle, direction, or distance by which the biological signal measurement device 300 is to be moved.

According to certain embodiments, the electronic device 104 connected to the biological signal measurement device 300 via a communication channel may output at least one of the first biological signal, the second biological signal, or the third biological signal. For example, the electronic device 104 may provide the user with the first biological signal, the second biological signal, and the third biological signal by a first graph S10, a second graph S20, and a third graph S30, respectively, through a display (e.g., the display 1301 in FIG. 15).

According to certain embodiments, the processor (e.g., the processor 120 in FIG. 1) of the biological signal measurement device 300 may be configured to: determine whether a measurement request has been made; and sense the first signal, the second signal, the third signal when the measurement request is made (e.g., in which the signals are not detected prior to the measurement request). According to an embodiment, the electronic device 104 may further include an attachment sensing sensor (e.g., the sensor module 176 in FIG. 1) for sensing whether a protective film (e.g., the low-adhesion protective film 822 in FIG. 12) detachably coupled to an attachment pad (e.g., the attachment pad 800 in FIG. 12) has been detached from the attachment pad. The processor 120 may determine, using the attachment sensing sensor, that there is a measurement request when the low-adhesion protective film 822 is separated from the attachment pad 800. According to another embodiment, the processor 120 may determine that there is a measurement request when a user input for the operation unit 311*a*, which is a switch device, is performed. Further, according to another embodiment, the processor 120 may include a packaging sensing sensor (e.g., the sensor module 176 in FIG. 1) for sensing whether the biological signal measurement device 300 has been packaged. For example, the packaging sensing sensor may include an illuminance sensor, and the processor 120 may determine that there is a measurement request when the illuminance of light using the illuminance sensor exceeds a predetermined range. In another example, when the illuminance of the light sensed using the illuminance sensor exceeds the predetermined range, the processor 120 may provide generated guide information to a user via the output unit 311*b*. The guide information may be pre-stored in a memory (e.g., the memory 130 in FIG. 1).

According to certain embodiments, the attachment sensing sensor may sense whether the low-adhesion protective film 822 has been attached or detached to or from the attachment pad 800 by using various methods. For example, the attachment sensing sensor may include at least one of an illuminance sensor, a piezo sensor, or a proximity sensor.

Figure 24:
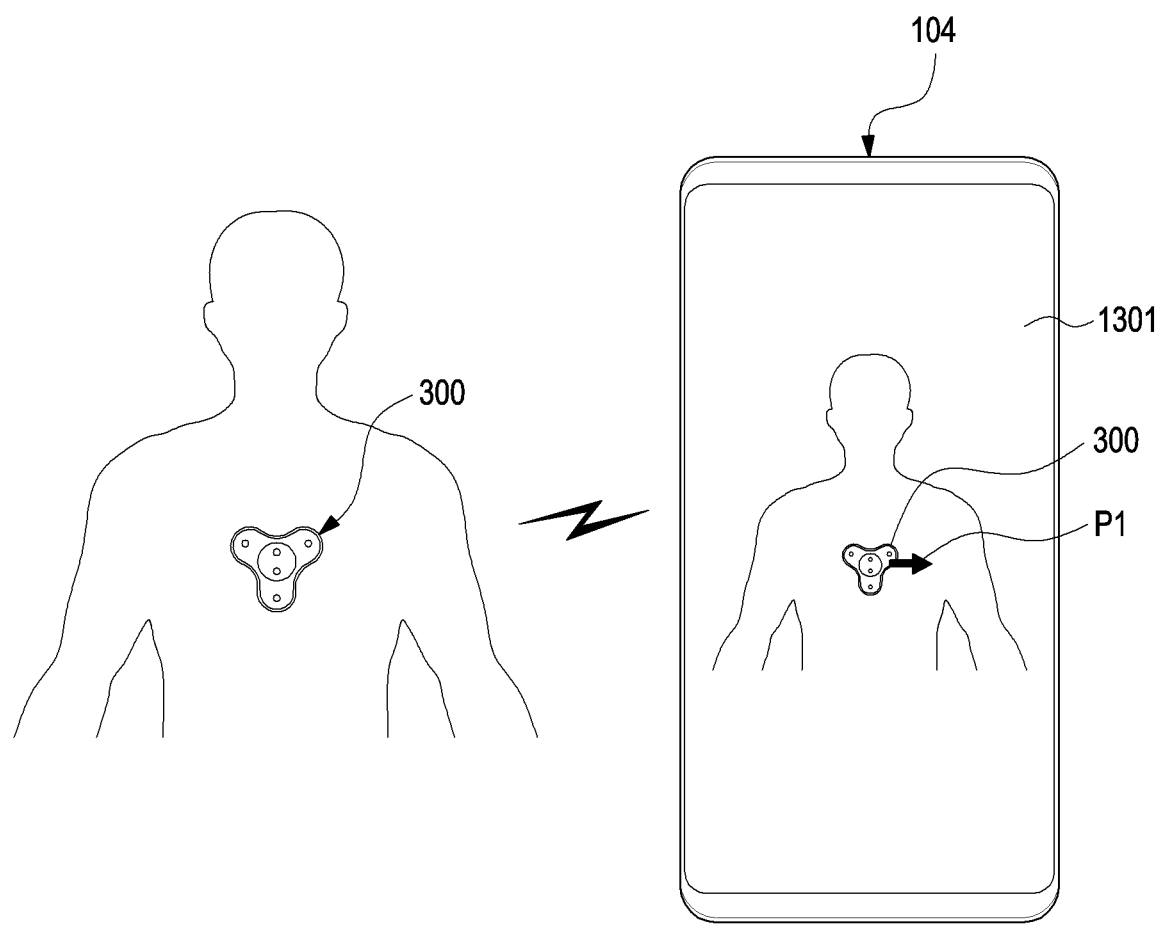
FIG. 24 illustrates an electronic device for outputting guide information of a biological signal measurement device according to certain embodiments.
Figure 25:
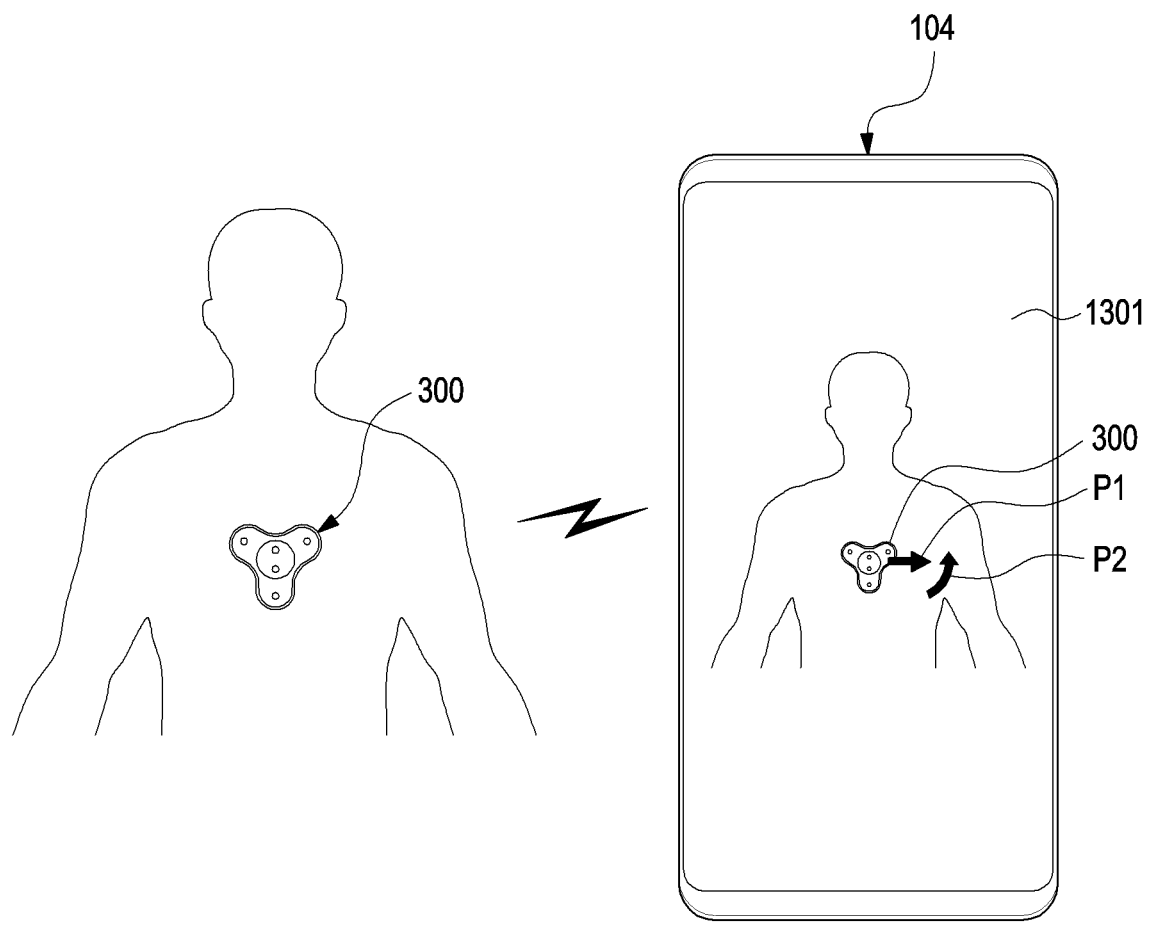
FIG. 25 illustrates an electronic device for outputting guide information of a biological signal measurement device according to certain embodiments.

FIG. 24 illustrates an electronic device for outputting guide information of a biological signal measurement device according to certain embodiments. FIG. 25 illustrates an electronic device for outputting guide information of a biological signal measurement device according to certain embodiments.

According to FIGS. 24 and 25, in order to acquire a normal biological signal, the electronic device 104 may output guide information for guiding the position of the biological signal measurement device 300. For example, the electronic device 104 may output light, an image, or sound, which is configured to reflect guide information, to the outside. The electronic device 104 may be configured to output at least one of the angle, direction, or distance by which the biological signal measurement device 300 is to be moved in order to measure the normal biological signal.

According to certain embodiments, the electronic device 104 may provide the guide information to a user by using various methods. According to an embodiment, the electronic device 104 may provide, via the display 1301, the user with the at least one of the angle, direction, or distance by which the biological signal measurement device 300 is to be moved. For example, electronic device 104 may output, based on guide information, a first pointer P1 of which at least one of the length, the size, or the direction changes, and may provide the guide information to the user. In another example, the electronic device 104 may output, based on guide information, a second pointer P2 of which at least one of the rotation direction or the angle changes, and may provide the guide information to the user. According to another embodiment, the electronic device 104 may provide, via the audio module 1303, 1307, or 1314, the user with at least one of the angle, direction, or distance by which the biological signal measurement device 300 is to be moved.

Figure 26:
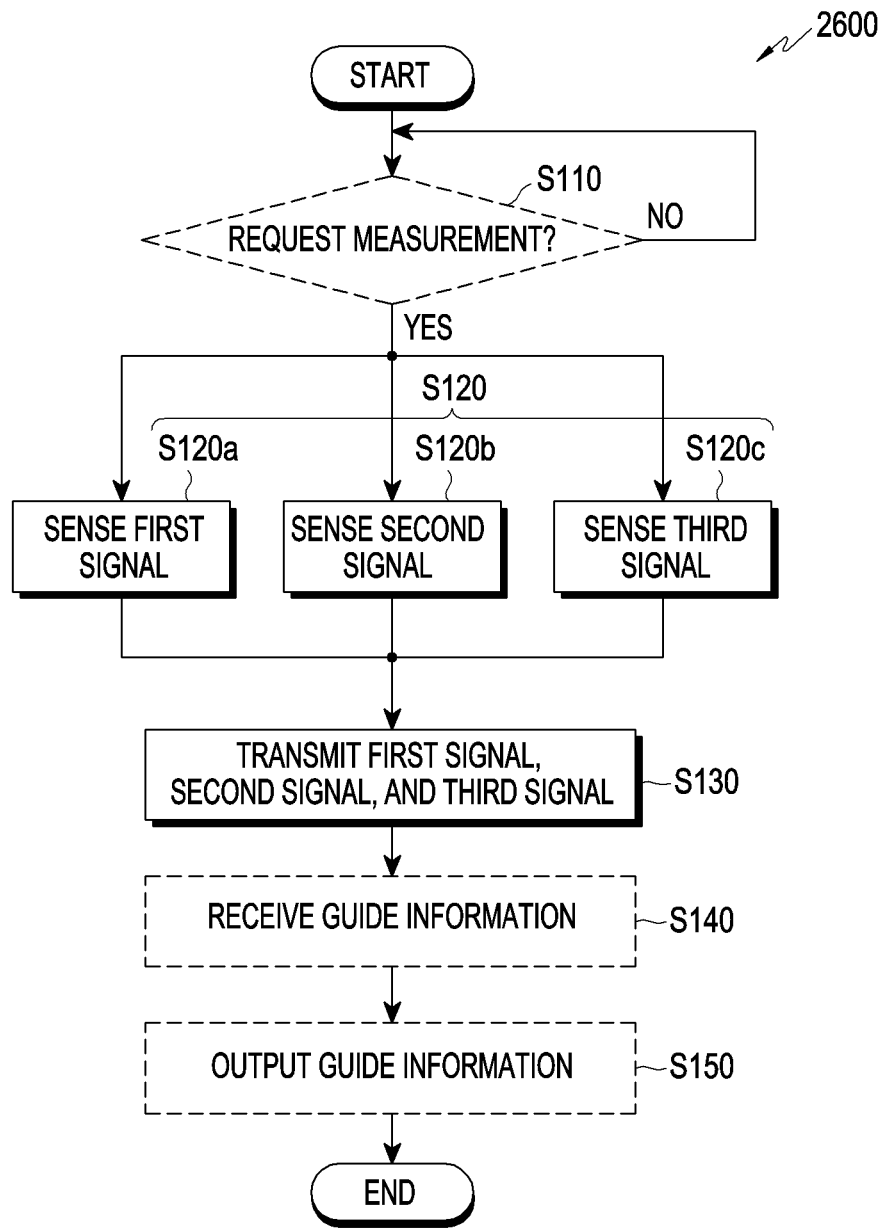
FIG. 26 is a flowchart for describing a method for transmitting a sensed signal and receiving guide information, by using an electronic device according to certain embodiments.
Figure 27:
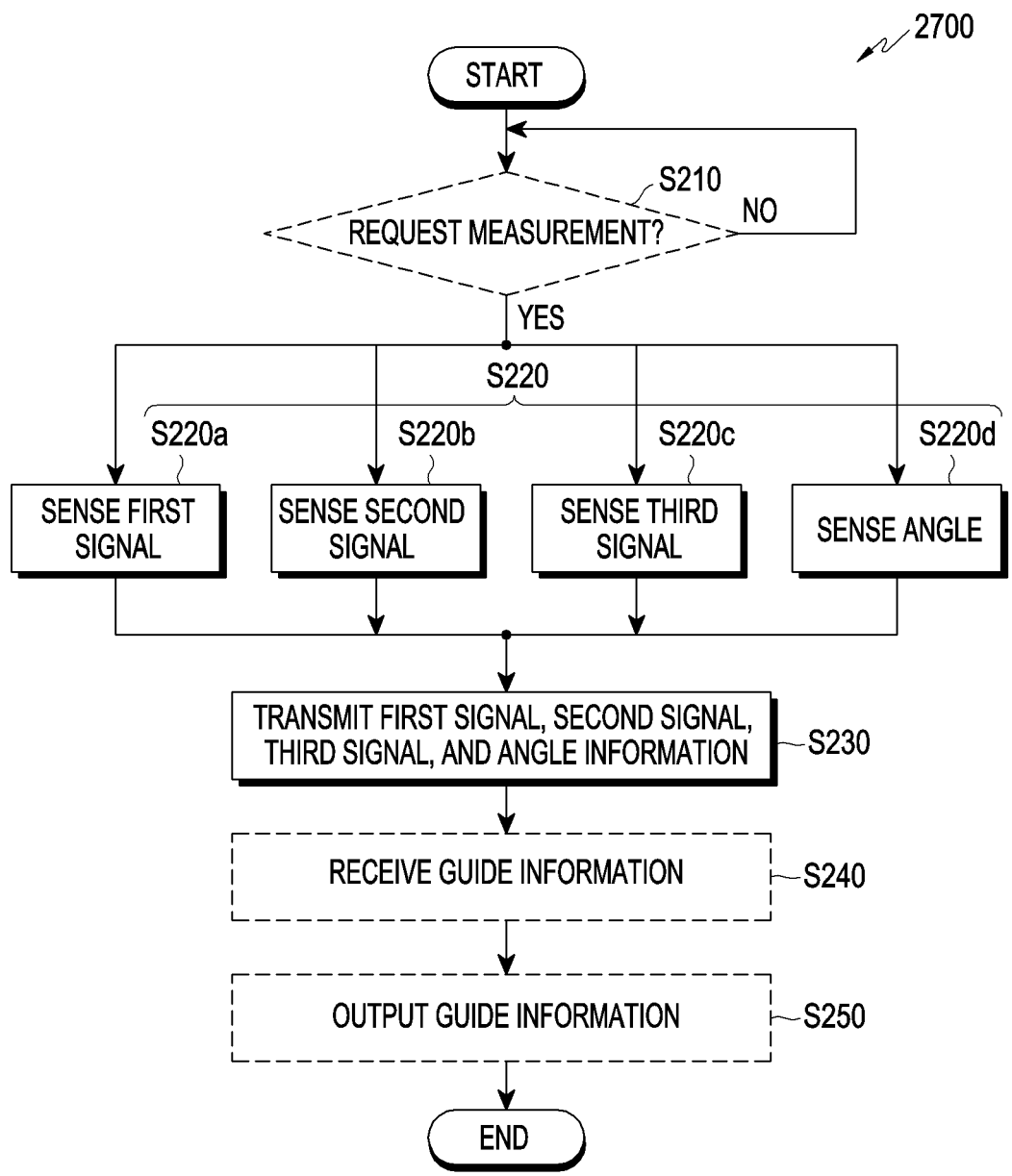
FIG. 27 is a flowchart for describing a method for transmitting a sensed signal and angle information and receiving guide information, by using an electronic device according to certain embodiments.

FIG. 26 is a flowchart for describing a method for transmitting a sensed signal and receiving guide information, by using an electronic device according to certain embodiments. FIG. 27 is a flowchart for describing a method for transmitting a sensed signal and angle information and receiving guide information, by using an electronic device according to certain embodiments.

Referring to FIG. 26, a first method 2600 may include: receiving (or identifying) an input or request regarding measurement (S110); sensing (or detecting) a signal, based on the received or identified request (S120); and transmitting the sensed signal (S130).

According to certain embodiments, the receiving (or identifying) of the input or request regarding the measurement (S110) may be an operation in which the processor (e.g., the processor 120 in FIG. 1 or the control unit 211 in FIG. 2) receives or identifies a signal corresponding to a measurement start or a measurement request (e.g., a request for measuring a biological signal such as an electrocardiogram). For example, the receiving (or identifying) of the input or request regarding the measurement (S110) may be at least one of an operation in which the processor receives a signal generated by operation of an operation unit (e.g., the operation unit 311*a* in FIG. 3) or an operation in which the attachment sensing sensor (e.g., the sensor module 176 in FIG. 1) detects separation of a protective film (e.g., the low-adhesion protective film 822 in FIG. 12) from an attachment pad (e.g., the attachment pad 800 in FIG. 8). According to an embodiment, in the case where an electronic device (e.g., the biological signal measurement device 300 in FIG. 3) has been attached to a user's body or a patient's body, when a signal received using the electrodes (e.g., the first electrode 631*a*, the second electrode 631*b*, the third electrode 631*c*, and the fourth electrode 631*d* in FIG. 7) is initially received, the processor may determine the initial signal to be "the input or request regarding the measurement".

According to certain embodiments, the sensing of a signal (S120) is an operation of sensing signals generated in the user's body or the patient's body, based at least partially on the measurement request, and the processor may sense the signals by using the first electrode (e.g., the first electrode 631*a* in FIG. 7), the second electrode (e.g., the second electrode 631*b* in FIG. 7), the third electrode (e.g., the third electrode 631*c* in FIG. 7), and the fourth electrode (e.g., the fourth electrode 631*d* in FIG. 7). According to an embodiment, the processor 120 may sense a first signal by using the first electrode 631a and the fourth electrode 631d (e.g., a reference electrode) (S120a), may sense a second signal by using the second electrode 631b and the fourth electrode 631d (S120b), and may sense a third signal by using the third electrode 631c and the fourth electrode 631d (S120c).

According to certain embodiments, the transmitting of the signal (S130) is an operation of transmitting at least some of the signals generated in the user's body or the patient's body to another electronic device (e.g., the electronic device 102 or 104 in FIG. 1) or a server (e.g., the server 108 in FIG. 1) via a communication module (e.g., the communication module 190 in FIG. 1 or the communication unit 235a in FIG. 2), and the communication module 190 may transmit at least one of the first signal, the second signal, and the third signal to the outside.

According to certain embodiments, the first method 2600 may further include receiving guide information (S140). The receiving of the guide information (S140) is an operation of receiving guide information generated based on a biological signal, and the communication module 190 may receive the guide information from another electronic device (e.g., the electronic device 102 or 104 in FIG. 1) or a server (e.g., the server 108 in FIG. 1).

According to certain embodiments, the first method 2600 may further include outputting guide information (S150). The outputting of the guide information (S150) is an operation of providing, based on the guide information, the user with a position to which a biological signal measurement device (e.g., the biological signal measurement device 300 in FIG. 23) is to be moved, and the biological signal measurement device 300 may provide, through at least one of an image, light, or sound output based on the guide information, the user with at least one of the angle, direction, or distance by which the biological signal measurement device 300 is to be moved.

Referring to FIG. 27, a second method 2700 may include: receiving (or identifying) an input or request regarding measurement (S210); sensing a signal, based on the received or identified request (S220); and transmitting the sensed signal (S230). The receiving (or identifying) of an input or request regarding measurement (S210), the sensing of a signal, based on the received or identified request (S220), and the transmitting of the sensed signal (S230) of the second method 2700 may be totally or partially identical to the receiving (or identifying) of an input or request regarding measurement (S110), the sensing of a signal, based on the received or identified request (S120), and the transmitting of the sensed signal (S130) of the first method 2600.

According to certain embodiments, the sensing of the signal (S220) may include sensing an angle by using an acceleration sensor (S220d). According to an embodiment, the processor 120 may determine the rotated angle of the biological signal measurement device 300 by using the acceleration sensor (e.g., the sensor module 176 in FIG. 1). For example, the processor 120 may sense an angle at which each of the first electrode 631a, the second electrode 631b, the third electrode 631c, and the fourth electrode 631d is disposed, and may generate angle information reflecting the angle at which each of the first electrode 631a, the second electrode 631b, the third electrode 631c, and the fourth electrode 631d is disposed.

According to certain embodiments, the transmitting of the signal (S230) may include transmitting the angle information to another electronic device (e.g., the electronic device 102 or 104 in FIG. 1) or a server (e.g., the server 108 in FIG. 1) via a communication module (e.g., the communication module 190 in FIG. 1 or the communication unit 235a in FIG. 2). For example, the communication module 190 may transmit a first signal, a second signal, a third signal, and the angle information to the outside.

According to certain embodiments, the second method 2700 may further include: receiving guide information (S240); and outputting guide information (S250). The receiving of guide information (S240) and the outputting of guide information (S250) of the second method 2700 may be totally or partially identical to the receiving of guide information (S140) and the outputting of guide information (S150) of the first method 2600.

Figure 28:
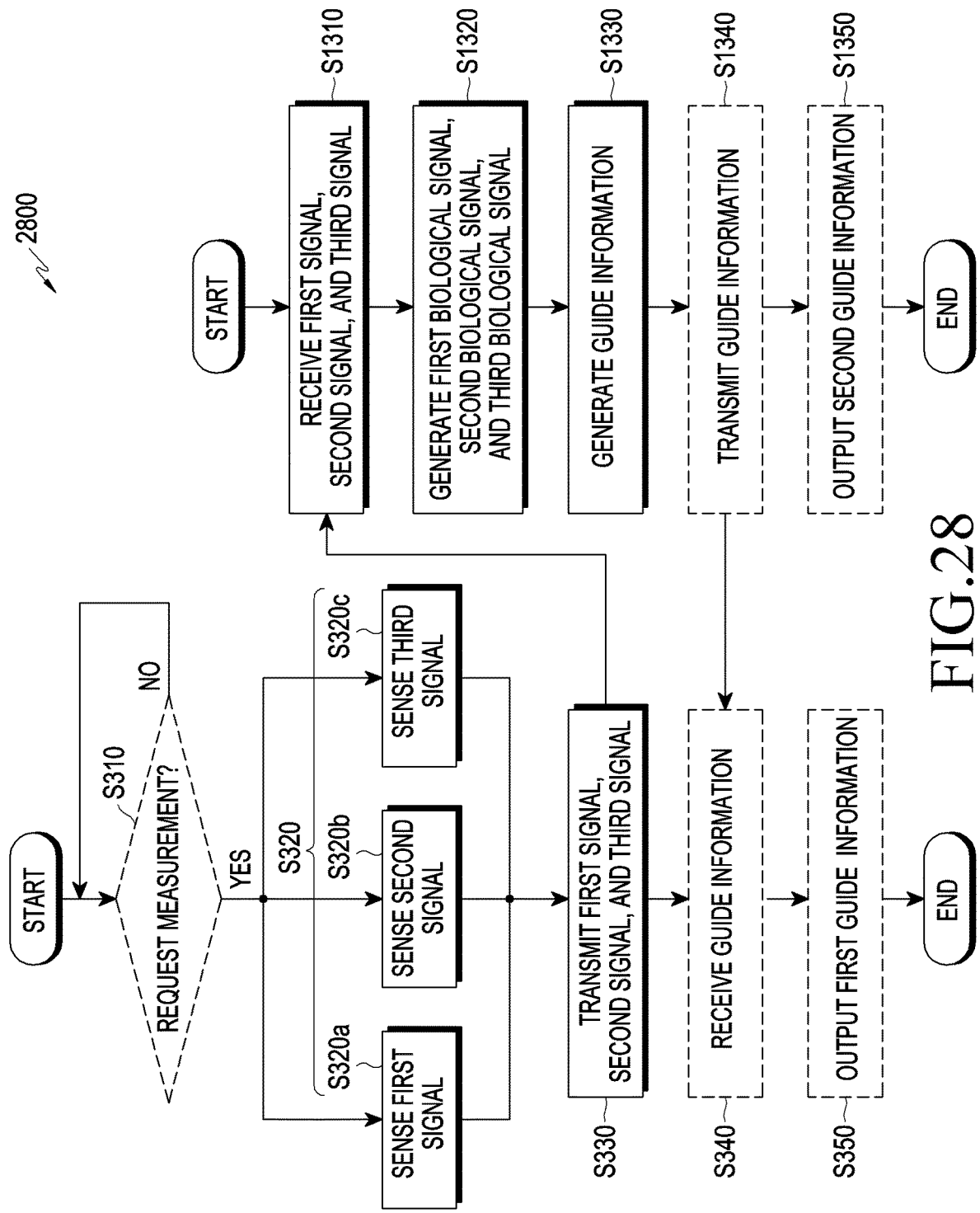
FIG. 28 is a flowchart for describing a method for outputting guide information by an electronic device for sensing a signal and by another electronic device for generating guide information, based on the sensed signal according to certain embodiments.
Figure 29:
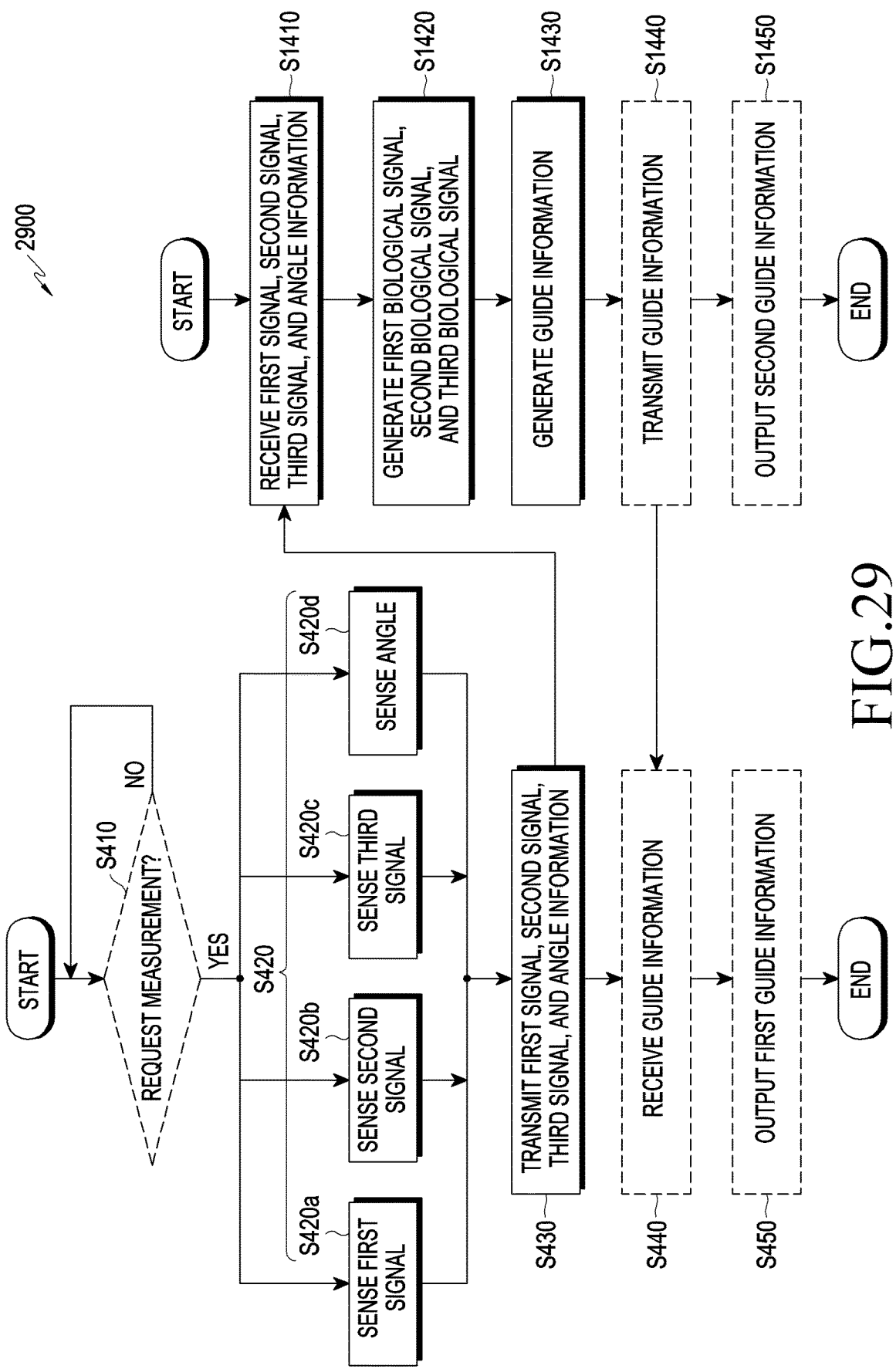
FIG. 29 is a flowchart for describing a method for outputting guide information by an electronic device for sensing an electrical signal and an angle and by another electronic device for generating guide information, based on the sensed signal and angle information.

FIG. 28 is a flowchart for describing a method for outputting guide information by an electronic device for sensing a signal and by another electronic device for generating guide information, based on the sensed signal according to certain embodiments. FIG. 29 is a flowchart for describing a method for outputting guide information by an electronic device for sensing an electrical signal and an angle and by another electronic device for generating guide information, based on the sensed signal and angle information.

Referring to FIG. 28, a third method 2800 may include: receiving (or identifying) an input or request regarding measurement (S310); sensing a signal, based on the received or identified request (S320); transmitting the sensed signal (S330); receiving the sensed signal (S1310); generating a biological signal based on the received signal (S1320); and generating guide information (S1330). The receiving (or identifying) of an input or request regarding measurement (S310), the sensing of a signal, based on the received or identified request (S320), and the transmitting of the sensed signal (S330) of the third method 2800 may be totally or partially identical to the receiving (or identifying) of an input or request regarding measurement (S110), the sensing of a signal, based on the received or identified request (S120), and the transmitting of the sensed signal (S130) of the first method 2600.

According to certain embodiments, the electronic device (e.g., the electronic device 102 or 104 in FIG. 1) or a server (e.g., the server 108 in FIG. 1) may receive a signal sensed by a biological signal measurement device (e.g., the biological signal measurement device 300 in FIG. 23) (S1310). For example, the electronic device 104 may receive a first signal, a second signal, and a third signal, which have been sensed by the biological signal measurement device 300, via a communication module (e.g., the communication module 190 in FIG. 1).

According to certain embodiments, the electronic device 102 or 104 or the server 108 may generate a biological signal, based on the received signal (S1320). For example, the electronic device 104 may: generate a first biological signal, based on the first signal and the second signal; generate a second biological signal, based on the second signal and the third signal; generate a third biological signal, based on the third signal and the first signal.

According to certain embodiments, the third method 2800 may further include generating guide information (S1330). For example, the electronic device 102 or 104 or the server 108 may generate guide information, based on the generated biological signal.

According to certain embodiments, the third method 2800 may further include: receiving the guide information (S340); and transmitting the guide information (S1340). The receiving of the guide information (S340) may be totally or partially identical to the receiving of the guide information (S140) of the first method 2600. The transmitting of the guide information (S1340) is an operation of transmitting the guide information generated based on the biological signal, and the electronic device (e.g., the electronic device 102 or 104 in FIG. 1) or a server (e.g., the server 108 in FIG. 1) may transmit the guide information to the biological signal measurement device 300 via a communication module.

According to certain embodiments, the third method 2800 may include at least one of outputting first guide information (S350) and outputting second guide information (S1350). According to an embodiment, the biological signal measurement device 300 may output guide information, but the electronic device 102 or 104 may not output guide information. For example, the outputting of the first guide information (S350) is an operation in which the biological signal measurement device 300 provides guide information to a user based on the received guide information. Through at least one of an image, light, or sound output based on the guide information, the biological signal measurement device 300 may provide the user with at least one of the angle, direction, or distance by which the biological signal measurement device 300 is to be moved. According to another embodiment, the electronic device 102 or 104 may output guide information, but the biological signal measurement device 300 may not output guide information. For example, the outputting of the second guide information (S1350) is an operation in which the electronic device 102 or 104 provides guide information to a user based on the received guide information. Through at least one of an image, light, or sound output based on the guide information, the electronic device 102 or 104 may provide the user with at least one of the angle, direction, or distance by which the biological signal measurement device 300 is to be moved. Further, according to another embodiment, the biological signal measurement device 300 and the electronic device 102 or 104 may output guide information. For example, the biological signal measurement device 300 may output the first guide information (S350), and the electronic device 102 or 104 may output the second guide information (S1350).

Referring to FIG. 29, a fourth method 2900 may include: receiving (or identifying) an input or request regarding measurement (S410); sensing a signal, based on the received or identified request (S420); transmitting of the sensed signal (S430); receiving the sensed signal (S1410); generating a biological signal based on the received signal (S1420); and generating guide information (S1430). The receiving (or identifying) of an input or request regarding measurement (S410), the sensing of a signal, based on the received or identified request (S420), the receiving of the sensed signal (S1410), the generating of a biological signal based on the received signal (S1420), and the generating guide information (S1430) of the fourth method 2900 may be totally or partially identical to the receiving (or identifying) of an input or request regarding measurement (S310), the sensing of a signal, based on the received or identified request (S320), the receiving of the sensed signal (S1310), the generating of a biological signal based on the received signal (S1320), and the generating guide information (S1330) of the third method 2800. The transmitting of the sensed signal (S430) of the fourth method 2900 may be totally or partially identical to the transmitting of the sensed signal of the second method 2700.

According to certain embodiments, the electronic device (e.g., the electronic device 102 or 104 in FIG. 1) or a server (e.g., the server 108 in FIG. 1 may receive angle information or an angle sensed by a biological signal measurement device (e.g., the biological signal measurement device 300 in FIG. 23). For example, the electronic device 104 may receive the angle information, sensed by the biological signal measurement device 300, via a communication module (e.g., the communication module 190 in FIG. 1).

According to certain embodiments, the fourth method 2900 may further include generating guide information (S1430). For example, the electronic device 102 or 104 or the server 108 may generate guide information, based on the generated biological signal or the angle information.

Figure 30:
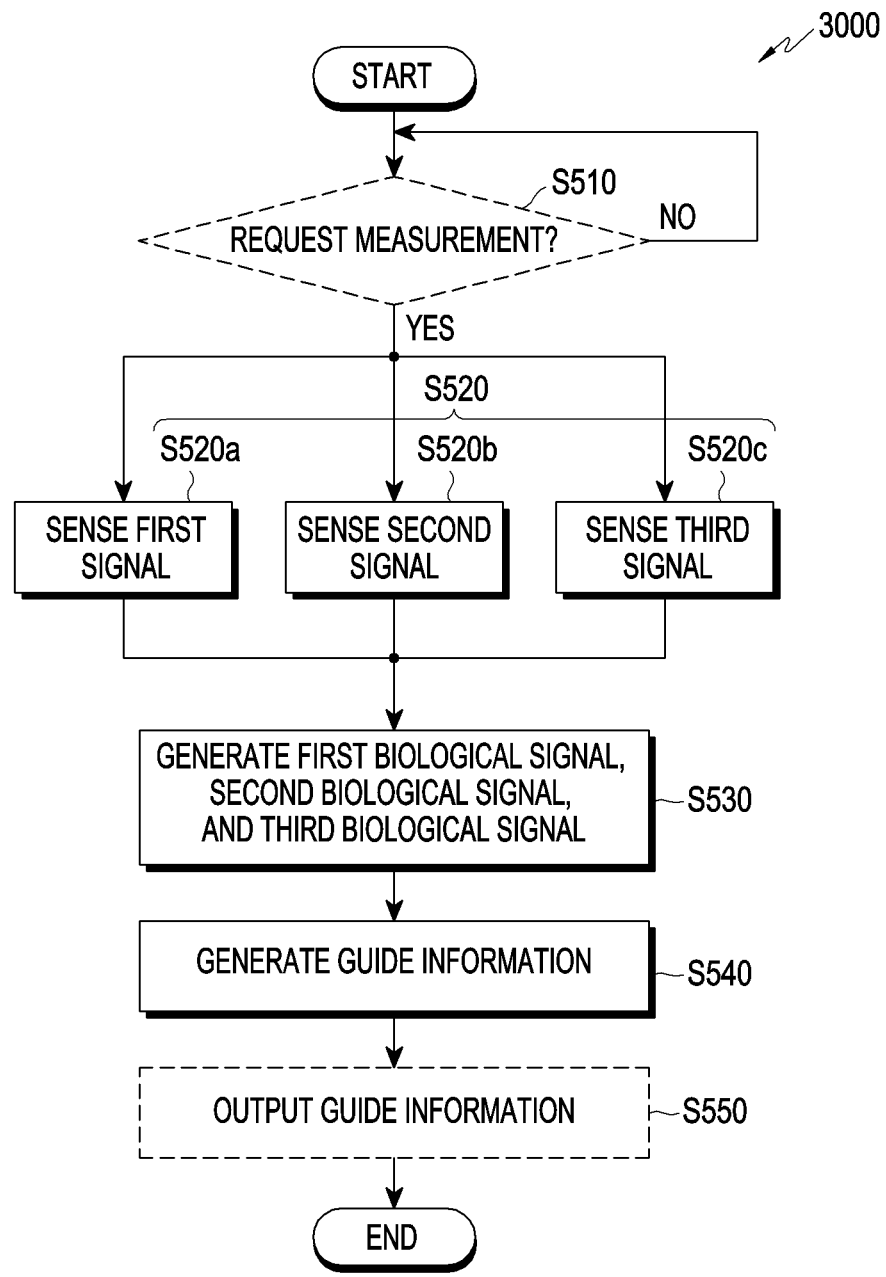
FIG. 30 is a flowchart for describing a method in which an electronic device generates guide information, based on multiple sensed signals according to certain embodiments.
Figure 31:
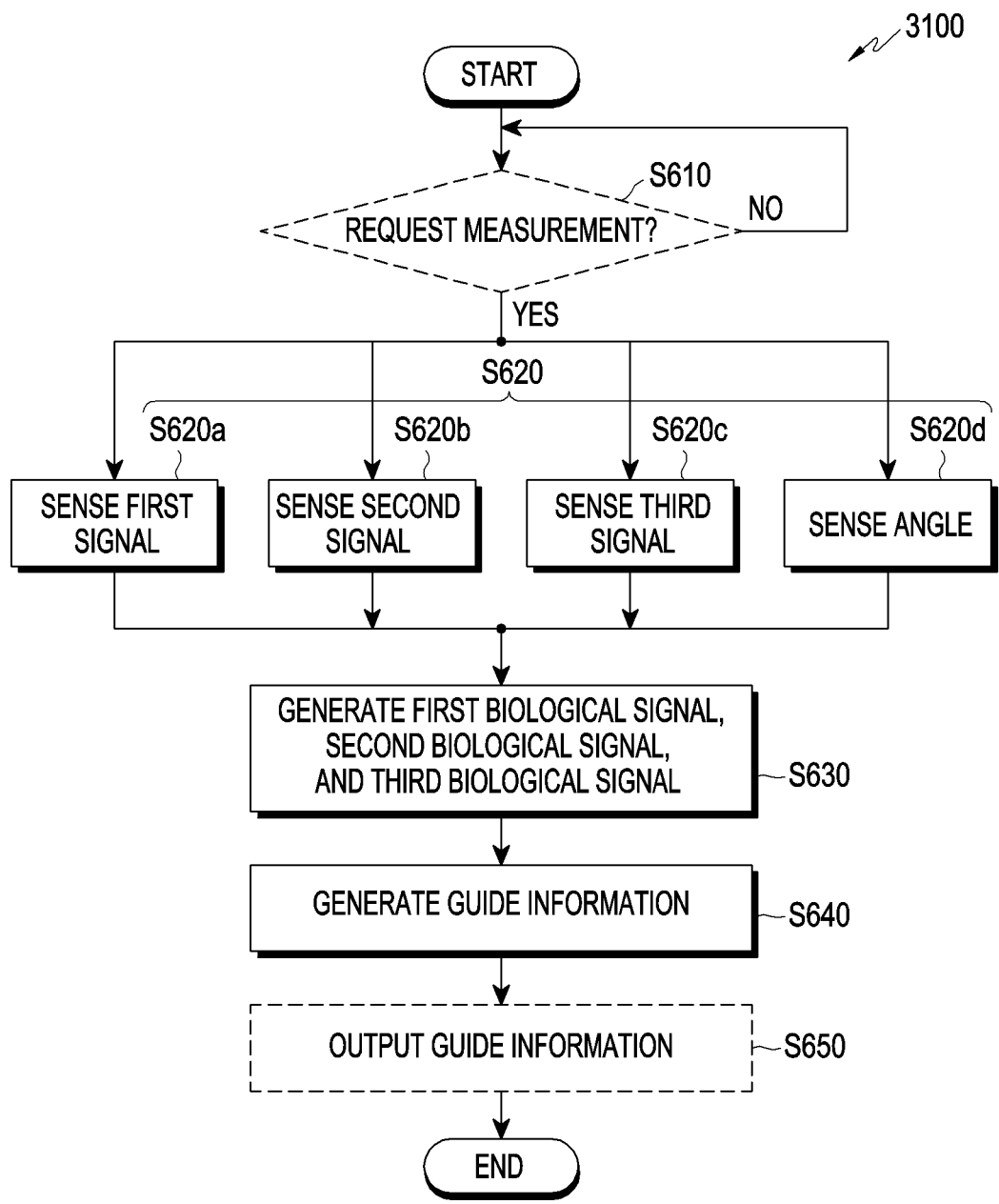
FIG. 31 is a flowchart for describing a method in which an electronic device generates guide information, based on multiple sensed signals and angle information according to certain embodiments.

FIG. 30 is a flowchart for describing a method in which an electronic device generates guide information, based on multiple sensed signals according to certain embodiments. FIG. 31 is a flowchart for describing a method in which an electronic device generates guide information, based on multiple sensed signals and angle information according to certain embodiments.

Referring to FIG. 30, a fifth method 3000 may include: receiving (or identifying) an input or request regarding measurement (S510); sensing a signal, based on the received or identified request (S520); generating a biological signal, based on the sensed signal (S530); and generating guide information (S540). The receiving (or identifying) of an input or request regarding measurement (S510) and the sensing a signal, based on the received or identified request (S520) of the fifth method 3000 may be totally or partially identical to the receiving (or identifying) of an input or request regarding measurement (S110) and the sensing a signal, based on the received or identified request (S120) of the first method 2600.

According to certain embodiments, the fifth method 3000 may further include generating a biological signal, based on the sensed signal (S530). For example, the biological signal measurement device (e.g., the biological signal measurement device 300 in FIG. 23) may: generate a first biological signal, based on the first signal and the second signal; generate a second biological signal, based on the second signal and the third signal; and generate a third biological signal, based on the third signal and the first signal.

According to certain embodiments, the fifth method 3000 may further include generating guide information (S540). For example, the biological signal measurement device 300 may generate guide information, based on the generated biological signal.

According to certain embodiments, the fifth method 3000 may further include outputting the guide information (S550). The outputting of the guide information (S550) is an operation in which the biological signal measurement device 300 provides guide information to a user, based on the generate guide information. Through at least one of an image, light, or sound output based on the guide information, the biological signal measurement device 300 may provide the user with at least one of the angle, direction, or distance by which the biological signal measurement device 300 is to be moved.

Referring to FIG. 31, a sixth method 3100 may include: receiving (or identifying) an input or request regarding measurement (S610); sensing of a signal, based on the received or identified request (S620); generating a biological signal, based on a sensed signal (S630); and generating guide information (S640). The receiving (or identifying) of an input or request regarding measurement (S610), the generating a biological signal, based on the sensed signal (S630), and the generating of guide information (S640) of the sixth method 3100 may be totally or partially identical to the receiving (or identifying) of an input or request regarding measurement (S510), the generating of a biological signal, based on the sensed signal (S530), and the generating of guide information (S540) of the fifth method 3000. The sensing of a signal (S620) may be totally or partially identical to the sensing of a signal (S220) of the second method 2700.

According to certain embodiments, in the generating of a biological signal, based on a sensed signal (S630), angle information may be further generated based on a sensed angle. For example, a processor (e.g., the processor 120 in FIG. 1) may generate angle information reflecting an angle at which the biological signal measurement device 300 is disposed.

According to certain embodiments, the sixth method 3100 may further include outputting guide information (S650). The outputting guide information (S650) may be totally or partially identical to the outputting guide information of the fifth method 3000.

An electronic device (e.g., the electronic device 101 in FIG. 1 or a biological signal measurement device (e.g., the biological signal measurement device 300 in FIG. 3) according to certain embodiments may include: a housing (e.g., the module housing 301 in FIG. 3 or the measurement module 400 in FIG. 5); a first electrode (e.g., the first electrode 631a in FIG. 7) disposed on one surface of the housing; a second electrode (e.g., the second electrode 631b in FIG. 7) disposed on one surface of the housing; a third electrode (e.g., the third electrode 631c in FIG. 7) disposed on one surface of the housing; a fourth electrode (e.g., the fourth electrode 631d in FIG. 7) disposed on one surface of the housing; a processor (e.g., the processor 120 in FIG. 1) disposed in the housing; and a communication module (e.g., the communication module 190 in FIG. 1) disposed in the housing, wherein the processor is configured to: sense a first signal by using the first electrode and the fourth electrode; sense a second signal by using the second electrode and the fourth electrode; and sense a third signal by using the third electrode and the fourth electrode, and wherein the communication module is configured to: transmit the first signal, the second signal, and the third signal to another electronic device (e.g., the electronic device 102 or 104); and receive, from the another electronic device, data which are related to guide information for guiding an attachment position of the electronic device and are generated based on a first biological signal (e.g., the first biological signal BS1 in FIG. 21D) generated based on the first signal and the second signal, a second biological signal (e.g., the second biological signal BS2 in FIG. 21D) generated based on the second signal and the third signal, and a third biological signal (e.g., the third biological signal BS3 in FIG. 21D) generated based on the third signal and the first signal.

According to certain embodiments, the electronic device may include an acceleration sensor (e.g., the accelerometer 239b in FIG. 2) disposed in the housing, the processor is configured to generate, using the acceleration sensor, angle information for reflecting the position of each of the first electrode, the second electrode, the third electrode, and the fourth electrode, and the communication module is configured to transmit the angle information to the another electronic device and receive, from the another electronic device, data related to the guide information generated in additional consideration of the angle information.

According to certain embodiments, the electronic device may include an attachment pad (e.g., the attachment pad 302 in FIG. 3) detachably disposed at the housing, wherein the attachment pad includes: a first terminal (e.g., the first terminal 731a in FIG. 9) electrically connectable to the first electrode; a second terminal (e.g., the second terminal 731b in FIG. 9) electrically connectable to the second electrode; a third terminal (e.g., the third terminal 731c in FIG. 9) electrically connectable to the third electrode; and a fourth terminal (e.g., the fourth terminal 731d in FIG. 9) electrically connectable to the fourth electrode.

According to certain embodiments, the attachment pad may further include: first wiring electrodes (e.g., the first wiring electrodes 831a in FIG. 12) electrically connected to the first terminal, the second terminal, the third terminal, or the fourth terminal, respectively; second wiring electrodes (e.g., the second wiring electrodes 831b in FIG. 12) extending from the first wiring electrode, respectively; and third wiring electrodes (e.g., the third wiring electrodes 831c in FIG. 12) provided at respective ends of the second wiring electrode, wherein the third wiring electrodes may be exposed in a direction different from that of the first terminal, the second terminal, the third terminal, or the fourth terminal.

According to certain embodiments, the electronic device may include an output unit (e.g., the output unit 311b in FIG. 3) configured to operate based on the guide information, wherein the output unit is configured to output at least one of the angle, direction, or distance by which the electronic device is to be moved.

According to certain embodiments, the electronic device may include an illuminance sensor (e.g., the sensor module 176 in FIG. 1) configured to sense the illuminance acquired by the electronic device, wherein the output unit is configured to output, when the illuminance exceeds a predetermined range, guide information for describing operation of the electronic device.

According to certain embodiments, the electronic device may further include: a protective film (e.g., the low-adhesion protective film 822 in FIG. 12) detachably coupled to the attachment pad; and an attachment sensing sensor (e.g., the sensor module 176 in FIG. 1) configured to sense whether the protective film is attached to or detached from the attachment pad. The processor may control supply of power to the communication module and the acceleration sensor, based on a signal sensed by the attachment sensing sensor.

According to certain embodiments, the processor may measure the impedance of the first electrode, the second electrode, the third electrode, or the fourth electrode.

An electronic device (e.g., the electronic device 102 or 104 in FIG. 1) according to certain embodiments may include: a housing (e.g., the housing 1310 in FIG. 15); a communication module (e.g., communication module 190 in FIG. 1) disposed in the housing; and a processor (e.g., the processor 120 in FIG. 1) disposed in the housing, wherein the processor is configured to: via the communication module, receive, from another electronic device (e.g., the electronic device 101 in FIG. 1 or a biological signal measurement device (e.g., the biological signal measurement device 300 in FIG. 3)), which includes a first electrode (e.g., the first electrode 631a in FIG. 7), a second electrode (e.g., the second electrode 631b in FIG. 7), a third electrode (e.g., the third electrode 631c in FIG. 7), and a fourth electrode (e.g., the fourth electrode 631d in FIG. 7), a first signal generated using the first electrode and the fourth electrode, a second signal generated using the second electrode and the fourth electrode, and a third signal generated using the third electrode and the fourth electrode; acquire a first biological signal (e.g., the first biological signal BS1 in FIG. 21D), based on the first signal and the second signal; acquire a second biological signal (e.g., the second biological signal BS2 in FIG. 21D), based on the second signal and the third signal; acquire a third biological signal (e.g., the third biological signal BS3 in FIG. 21D), based on the third signal and the first signal; acquire data related to guide information for guiding an attachment position of the another electronic device, based on the first biological signal, the second biological signal, and the third biological signal; and transmit the data related to the guide information to the another electronic device via the communication module.

According to certain embodiments, the communication module may be configured to further receive angle information for reflecting an angle of the another electronic device, and the processor may be configured to generate the data related to the guide information in additional consideration of the angle information.

According to certain embodiments, the processor may be configured to generate guide information including at least one of an angle, a direction, or a distance by which the another electronic device is to be moved.

According to certain embodiments, the processor may be configured to compare each of the first biological signal, the second biological signal, and the third biological signal with a preconfigured biological signal (e.g., the preconfigured biological signal (PBS) in FIG. 20) to generate the guide information for guiding a displacement amount of the another electronic device.

According to certain embodiments, the preconfigured biological signal may include information on at least one of a QRS wave (QRS-complex), a PR segment, an ST segment, a P-R interval, a QT interval, and an amplitude of a voltage (V).

According to certain embodiments, the electronic device may include an output unit (e.g., the display 1301 or the audio module 1303, 1307, or 1314 in FIG. 15) configured to operate based on the guide information, wherein the output unit may be configured to output at least one of an angle, a direction, and a distance by which the another electronic device is to be moved.

According to certain embodiments, the processor may compare each of the first biological signal, the second biological signal, and the biological signal with a preconfigured biological signal so as to determine whether the first electrode, the second electrode, the third electrode, and the fourth electrode are attached to a user's body.

An electronic device (e.g., the electronic device 101 in FIG. 1 or a biological signal measurement device (e.g., the biological signal measurement device 300 in FIG. 3) according to certain embodiments may include: a housing (e.g., the module housing 301 in FIG. 3 or the measurement module 400 in FIG. 5); a first electrode (e.g., the first electrode 631a in FIG. 7) disposed at the housing; a second electrode (e.g., the second electrode 631b in FIG. 7) disposed at the housing; a third electrode (e.g., the third electrode 631c in FIG. 7) disposed at the housing; a fourth electrode (e.g., the fourth electrode 631d in FIG. 7) disposed at the housing; and a processor (e.g., the processor 120 in FIG. 1) disposed in the housing, wherein the processor is configured to: sense a first signal by using the first electrode and the fourth electrode; sense a second signal by using the second electrode and the fourth electrode; sense a third signal by using the third electrode and the fourth electrode; generate a first biological signal (e.g., the first biological signal BS1 in FIG. 21D), based on the first signal and the second signal; generate a second biological signal (e.g., the second biological signal BS2 in FIG. 21D), based on the second signal and the third signal; generate a third biological signal (e.g., the third biological signal BS3 in FIG. 21D), based on the third signal and the first signal; and generate data related to guide information for guiding an attachment position of the electronic device, based on the first biological signal, the second biological signal, and the third biological signal.

According to certain embodiments, the electronic device may include an acceleration sensor (e.g., the accelerometer 239b in FIG. 2) disposed in the housing, wherein the processor is configured to: generate, based on the acceleration sensor, angle information reflecting a position of each of the first electrode, the second electrode, the third electrode, and the fourth electrode; and generate data related to the guide information in additional consideration of the angle information.

According to certain embodiments, the electronic device may include an output unit (e.g., the output unit 311b in FIG. 3) configured to operate based on the guide information, wherein the output unit is configured to output at least one of an angle, a direction, and a distance by which the electronic device is to be moved.

According to certain embodiments, the processor may be configured to compare each of the first biological signal, the second biological signal, and the third biological signal with a preconfigured biological signal (e.g., the preconfigured biological signal (PBS) in FIG. 20) to generate the guide information for guiding a displacement amount of the electronic device.

According to certain embodiments, the electronic device may include an attachment pad (e.g., the attachment pad 302 in FIG. 3) detachably disposed at the housing, wherein the attachment pad may include: a first terminal (e.g., the first terminal 731a in FIG. 9) electrically connectable to the first electrode; a second terminal (e.g., the second terminal 731b in FIG. 9) electrically connectable to the second electrode; a third terminal (e.g., the third terminal 731c in FIG. 9) electrically connectable to the third electrode; and a fourth terminal (e.g., the fourth terminal 731d in FIG. 9) electrically connectable to the fourth electrode.

According to certain embodiments, the electronic device may include: a protective film (e.g., the low-adhesion protective film 822 in FIG. 12) detachably coupled to the attachment pad; and an attachment sensing sensor (e.g., the sensor module 176 in FIG. 1) configured to sense whether the protective film is attached to or detached from the attachment pad, wherein the processor may control supply of power to the communication module and the acceleration sensor, based on a signal sensed by the attachment sensing sensor.

An electronic device (e.g., the electronic device 102 or 104 in FIG. 1) according to certain embodiments may include: a housing (e.g., the housing 1310 in FIG. 15); a communication module (e.g., the communication module 190 in FIG. 1) disposed in the housing; and a processor (e.g., the processor 120 in FIG. 1) disposed in the housing, wherein the processor is configured to: via the communication module, acquire, from another electronic device (e.g., the electronic device 101 in FIG. 1 or a biological signal measurement device (e.g., the biological signal measurement device 300 in FIG. 3)), which includes a first electrode (e.g., the first electrode 631a in FIG. 7), a second electrode (e.g., the second electrode 631b in FIG. 7), a third electrode (e.g., the third electrode 631c in FIG. 7), and a fourth electrode (e.g., the fourth electrode 631d in FIG. 7), a first signal generated using the first electrode and the fourth electrode, a second signal generated using the second electrode and the fourth electrode, and a third signal generated using the third electrode and the fourth electrode; generate a first biological signal (e.g., the first biological signal BS1 in FIG. 21D), based on the first signal and the second signal; generate a second biological signal (e.g., the second biological signal BS2 in FIG. 21D), based on the second signal and the third signal; generate a third biological signal (e.g., the third biological signal BS3 in FIG. 21D), based on the third signal and the first signal; generate data related to guide information for guiding an attachment position of the another electronic device, based on the first biological signal, the second biological signal, and the third biological signal; and transmit the data related to the guide information to the another electronic device via the communication module.

It will be obvious to a person skilled in the art to which the disclosure belongs that the electronic device including an input region of certain embodiments described above is not limited to the above described embodiments and the accompanying drawings and that various substitutions, modifications, and changes are possible within the technical range of the disclosure.

What is claimed is:

1. An electronic device comprising:
   a housing;
   a first, second, third and fourth electrode coupled to the housing;
   a communication module;
   an acceleration sensor disposed in the housing; and
   a processor, configured to:
   detect a first signal using the first electrode and the fourth electrode;
   detect a second signal using the second electrode and the fourth electrode;
   detect a third signal using the third electrode and the fourth electrode;
   acquire, using the acceleration sensor, angle information corresponding to respective positions of the first electrode, the second electrode, the third electrode, and the fourth electrode;
   transmit the first signal, the second signal, the third signal and the angle information to an external electronic device via the communication module; and
   receive, from the external electronic device, via the communication module, data for generating guidance information to correct an attachment position of the electronic device,
   wherein the guidance information is generated based on:
   a first biological signal generated based on the first signal and the second signal,
   a second biological signal generated based on the second signal and the third signal,
   a third biological signal generated based on the third signal and the first signal, and
   the guidance information is generated based on the data and the angle information.

2. The electronic device of claim 1, further comprising an attachment pad detachably coupled to the housing, wherein the attachment pad comprises:
   a first terminal electrically connectable to the first electrode;
   a second terminal electrically connectable to the second electrode;
   a third terminal electrically connectable to the third electrode; and
   a fourth terminal electrically connectable to the fourth electrode.

3. The electronic device of claim 2, further comprising:
   a protective film detachably coupled to the attachment pad; and
   an attachment sensor configured to detect whether the protective film is attached to or detached from the attachment pad,
   wherein the processor is further configured to control a supply of power to the communication module based on a signal generated by the attachment sensor.

4. The electronic device of claim 1, further comprising an output unit configured to output the guidance information, including at least one of an angle, a direction, or a distance by which the electronic device is to be moved.

5. The electronic device of claim 4, further comprising an illuminance sensor configured to detect environment illuminance,
   wherein the guidance information is output by the output unit when the illuminance exceeds a predetermined illuminance range.

6. The electronic device of claim 1, wherein the processor is configured to measure an impedance of at least one of the first electrode, the second electrode, the third electrode, and the fourth electrode.

7. An electronic device comprising:
   a housing;
   a communication module; and
   a processor disposed in the housing,
   wherein the processor is configured to:
   receive, via the communication module, a plurality of signals generated from a first, second, third and fourth electrode of an external electronic device, including: a first signal generated using the first electrode and the fourth electrode, a second signal generated using the second electrode and the fourth electrode, and a third signal generated using the third electrode and the fourth electrode;
   receive, via the communication module, angle information indicating an angle of the external electronic device;
   determine a first biological signal based on the first signal and the second signal;
   determine a second biological signal based on the second signal and the third signal;
   determine a third biological signal based on the third signal and the first signal;
   generate correction data indicating a correction to an attachment position of the external electronic device, based on the first biological signal, the second biological signal, the third biological signal, and the angle information; and
   transmit the correction data to the external electronic device via the communication module.

8. The electronic device of claim 7, wherein the processor is further configured to generate guidance information including at least one of an angle, a direction, and a distance by which the external electronic device is to be moved to correct positioning of the external electronic device.

9. The electronic device of claim 8, wherein the processor compares each of the first biological signal, the second biological signal, and the biological signal with preconfigured biological signals to determine whether the first electrode, the second electrode, the third electrode, and the fourth electrode are attached to a user's body.

10. The electronic device of claim 7, wherein generating the guidance information further includes comparing each of the first biological signal, the second biological signal, and the third biological signal with preconfigured biological signals, and
   wherein the generated guidance information indicates a displacement amount of the external electronic device to cause the first, second and third biological signals to approach one or more values of the preconfigured biological signals.

11. The electronic device of claim 10, wherein the preconfigured biological signal comprises information on at least one of a QRS wave (QRS-complex), a PR segment, an ST segment, a P-R interval, a QT interval, and an amplitude of a voltage.

12. The electronic device of claim 7,
further comprising an output unit is configured to output the guidance information, including at least one of an angle, a direction, or a distance by which the electronic device is to be moved.

13. An electronic device comprising:
a housing;
a communication module;
a first, second, third, and fourth electrode coupled to the housing;
an acceleration sensor disposed in the housing;
a processor, configured to:
detect a first signal using the first electrode and the fourth electrode;
detect a second signal using the second electrode and the fourth electrode;
detect a third signal using the third electrode and the fourth electrode;
acquire, using the acceleration sensor, angle information corresponding to respective positions of the first electrode, the second electrode, the third electrode, and the fourth electrode;
generate a first biological signal based on the first signal and the second signal;
generate a second biological signal based on the second signal and the third signal;
generate a third biological signal based on the third signal and the first signal;
transmit, via the communication module, the angle information to an external electronic device; and
generate correction data indicating a correction to an attachment position of the external electronic device, based on the first biological signal, the second biological signal, the third biological signal, and the angle information.

14. The electronic device of claim 13, further comprising an output unit configured to output the guidance information, including at least one of an angle, a direction, or a distance by which the electronic device is to be moved.

15. The electronic device of claim 13, wherein generating the guidance information further includes comparing each of the first biological signal, the second biological signal, and the third biological signal with preconfigured biological signals, and
wherein the generated guidance information indicates a displacement amount of the external electronic device to cause the first, second and third biological signals to approach one or more values of the preconfigured biological signals.

16. The electronic device of claim 13, further comprising an attachment pad detachably coupled to the housing, wherein the attachment pad comprises:
a first terminal electrically connectable to the first electrode;
a second terminal electrically connectable to the second electrode;
a third terminal electrically connectable to the third electrode; and
a fourth terminal electrically connectable to the fourth electrode.

17. The electronic device of claim 16, a protective film detachably coupled to the attachment pad; and
an attachment sensor configured to detect whether the protective film is attached to or detached from the attachment pad,
wherein the processor is further configured to control a supply of power to the communication module based on a signal generated by the attachment sensor.

* * * * *